United States Patent
Gibson et al.

(10) Patent No.: US 11,261,173 B2
(45) Date of Patent: *Mar. 1, 2022

(54) BRADYKININ B2 RECEPTOR ANTAGONISTS

(71) Applicant: Pharvaris Netherlands B.V., Leiden (NL)

(72) Inventors: Christoph Gibson, Berlin (DE); Joern Saupe, Potsdam (DE); Horst-Dieter Ambrosi, Berlin (DE); Lars Ole Haustedt, Falkensee (DE)

(73) Assignee: PHARVARIS NETHERLANDS B.V., Leiden (NL)

( * ) Notice: Subject to any disclaimer, the term of this patent is extended or adjusted under 35 U.S.C. 154(b) by 0 days.

This patent is subject to a terminal disclaimer.

(21) Appl. No.: 17/033,347

(22) Filed: Sep. 25, 2020

(65) Prior Publication Data

US 2021/0017158 A1   Jan. 21, 2021

Related U.S. Application Data

(63) Continuation of application No. 16/861,131, filed on Apr. 28, 2020, now Pat. No. 10,836,748, which is a continuation of application No. PCT/EP2018/082338, filed on Nov. 23, 2018.

(30) Foreign Application Priority Data

Nov. 24, 2017   (EP) ..................... 17203675

(51) Int. Cl.
| | |
|---|---|
| C07D 401/14 | (2006.01) |
| C07D 401/04 | (2006.01) |
| C07D 405/14 | (2006.01) |
| C07D 413/14 | (2006.01) |
| C07D 417/14 | (2006.01) |

(52) U.S. Cl.
CPC ......... *C07D 401/14* (2013.01); *C07D 401/04* (2013.01); *C07D 405/14* (2013.01); *C07D 413/14* (2013.01); *C07D 417/14* (2013.01)

(58) Field of Classification Search
CPC .................................... C07D 401/14
USPC ...................................... 546/159
See application file for complete search history.

(56) References Cited

U.S. PATENT DOCUMENTS

2020/0255405 A1   8/2020   Gibson et al.

FOREIGN PATENT DOCUMENTS

| EP | 0795547 B1 | 5/2000 |
|---|---|---|
| EP | 0622361 B1 | 10/2001 |
| EP | 0796848 B1 | 6/2003 |
| EP | 1213289 B1 | 11/2003 |
| EP | 0867432 B1 | 6/2004 |
| EP | 0797997 B1 | 6/2005 |
| WO | WO-9613485 A1 | 5/1996 |
| WO | WO-9707115 A1 | 2/1997 |
| WO | WO-9728153 A1 | 8/1997 |
| WO | WO-9741104 A1 | 11/1997 |
| WO | WO-9964039 A1 | 12/1999 |
| WO | WO-0023439 A1 | 4/2000 |
| WO | WO-0050418 A1 | 8/2000 |
| WO | WO-0075107 A2 | 12/2000 |
| WO | WO-0156995 A1 | 8/2001 |
| WO | WO-03087090 A2 | 10/2003 |
| WO | WO-03103671 A1 | 12/2003 |
| WO | WO-2006040004 A1 | 4/2006 |
| WO | WO-2007003411 A2 | 1/2007 |
| WO | WO-2008116620 A1 | 10/2008 |
| WO | WO-2010031589 A1 | 3/2010 |
| WO | WO-2014159637 A1 | 10/2014 |
| WO | WO-2019101906 A1 | 5/2019 |

OTHER PUBLICATIONS

Akbary et al. Efficacy and tolerability of Icatibant (Hoe 140) in patients with moderately severe chronic bronchial asthma. Immunopharmacology 33:238-42 (1996).

(Continued)

*Primary Examiner* — Taofiq A Solola

(74) *Attorney, Agent, or Firm* — Wilson Sonsini Goodrich & Rosati

(57) ABSTRACT

The invention relates to a compound according to general formula (I), which acts as a bradykinin (BK) B2 receptor antagonist; to a pharmaceutical composition containing one or more of the compound(s) of the invention; to a combination preparation containing at least one compound of the invention and at least one further active pharmaceutical ingredient; and to uses of said compound(s), including the use as a medicament.

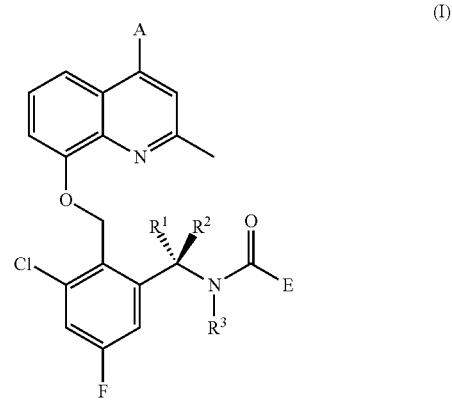

(I)

15 Claims, No Drawings

(56) References Cited

OTHER PUBLICATIONS

Bas et al. Novel pharmacotherapy of acute hereditary angioedema with bradykinin B2-receptor antagonist icatibant. Allergy 61:1490-2 (2006).
Bielory et al. Long-acting ACE inhibitor-induced angioedema. Allergy Proc. 13:85-7 (1992).
Birklein et al. The important role of neuropeptides in complex regional pain syndrome. Neurology 57:2179-84 (2001).
Bond et al. Generation of kinins in synovial fluid from patients with arthropathy. Immunopharmacology 36:209-16 (1997).
Calixto et al. Kinins in pain and inflammation. Pain 87:1-5 (2000).
CAMPBELL. The kallikrein-kinin system in humans. Clin. Exp. Pharmacal. Physial. 28:1060-5 (2001).
Cassim et al. Immunolocalization of bradykinin receptors on human synovial tissue. Immunopharmacology 36:121-5 (1997).
Cugno et al. Bradykinin in the ascitic fluid of patients with liver cirrhosis. Clin. Sci. (Lond) 101:651-7 (2001).
Davis et al. The pathogenesis of hereditary angioedema. Transfus. Apher. Sci. 29:195-203 (2001).
Ebersberger et al. Recordings from brain stem neurons responding to chemical stimulation of the subarachnoid space. J Neurophysiol. 77(6):3122-33 (1997).
Fernando et al. Assembly, activation, and signaling by kinin-forming proteins on human vascular smooth muscle cells. Am J Physiol Heart Circ Physiol 289(1):H251-7 (2005).
Finley et al. Angiotensin-converting enzyme inhibitor-induced angioedema: still unrecognized. Am. J Emerg. Med. 10:550-2 (1992).
Frigas et al. Idiopathic recurrent angioedema. Immunol. Allergy Clin. North Am. 26:739-51 (2006).
Gao et al. Extracellular carbonic anhydrase mediates hemorrhagic retinal and cerebral vascular permeability through prekallikrein activation. Nat Med 13(2):181-188 (2007).
JONKAM et al. Effects of the bradykinin B2 receptor antagonist icatibant on microvascular permeability after thermal injury in sheep. Shock 28(6):704-9 (2007).
Kaneyama et al. Prognostic factors in arthrocentesis of the temporomandibular joint: Comparison of bradykinin, leukotriene B4, prostaglandin E2, and substance P level in synovial fluid between successful and unsuccessful cases. Oral. Maxillofac. Surg. 65:242-7 (2007).
Kaplan et al. Angioedema. J Am. Acad. Dermatol. 53:373-88 (2005).
Marmarou et al. A single dose, three-arm, placebo-controlled, phase I study of the bradykinin B2 receptor antagonist Anatibant (LF16-0687Ms) in patients with severe traumatic brain injury. J Neurotrauma 22(12):1444-55 (2005).
MARX. Fluid therapy in sepsis with capillary leakage. Eur J Anaesthesia. 20(6):429-42 (2003).
Mathelier-Fusade. Drug-induced urticarias. Clin. Rev. Allergy Immunol. 30:19-23 (2006).
Meini et al. Characterization of bradykinin B(2) receptor antagonists in human and rat urinary bladder. Eur. J. Pharmacal. 388:177-82 (2000).
Nwariaku et al. Effect of a bradykinin antagonist on the local inflammatory response following thermal injury. Burns 22:324-7 (1996).
PCT/EP2018/082338 International Search Report and Written Opinion dated Feb. 11, 2019.
Petersen et al. Plasticity in the expression of bradykinin binding sites in sensory neurons after mechanical nerve injury. Neuroscience 83:949-59 (1998).
Pretorius et al. A pilot study indicating that bradykinin B2 receptor antagonism attenuates protamine-related hypotension after cardiopulmonary bypass. Clin Pharmacal Ther. 78(5):477-85 (2005).
Regoli et al. Pharmacology of bradykinin and related kinins. Pharmacol. Rev. 32:1-46 (1980).
Robillard et al. The syndrome of amniotic fluid embolism: a potential contribution of bradykinin. Am J Obstet Gynecol. 193(4):1508-12 (2005).
Rosamilia et al. Activation of the kallikrein kinin system in interstitial cystitis. J. Ural. 162:129-34 (1999).
Sainz et al. Fifty years of research on the plasma kallikrein-kinin system: from protein structure and function to cell biology and in-vivo pathophysiology. Thromb. Haemost 98:77-83 (2007).
Speicher et al. Pharmacologic therapy for diabetic retinopathy. Expert Opin. Emerg. Drugs 8:239-50 (2003).
Srinivasan et al. Pharmacological and functional characterization of bradykinin B2 receptor in human prostate. Eur J Pharmacal. 504(3):155-67 (2004).
Ujioka et al. Involvement of ovarian kinin-kallikrein system in the pathophysiology of ovarian hyperstimulation syndrome: studies in a rat model. Hum Reprod. 13(11):3009-15 (1998).
Wirth et al. The bradykinin B2 receptor antagonist Icatibant (HOE 140) corrects avid Na+ retention in rats with CCl4-induced liver cirrhosis: possible role of enhanced microvascular leakage. Eur. J. Pharmacol. 337:45-53 (1997).
Yamaguchi-Sase et al. Amelioration of hyperalgesia by kinin receptor antagonists or kininogen deficiency in chronic constriction nerve injury in rats. Inflamm Res. 52:164-9 (2003).
Zuraw. Novel therapies for hereditary angioedema. Immunol. Allergy Clin. North Am. 26:691-708 (2006).
Zuraw et al. Activation of urinary kallikrein in patients with interstitial cystitis. J Ural 152:874-8 (1994).

BRADYKININ B2 RECEPTOR ANTAGONISTS

CROSS-REFERENCE

This application is a continuation of U.S. patent application Ser. No. 16/861,131 filed Apr. 28, 2020, which is a continuation of International Application No. PCT/EP2018/082338 filed Nov. 23, 2018, which claims the benefit of EP 17203675.8 filed on Nov. 24, 2017, all of which are hereby incorporated by reference in their entireties.

FIELD OF THE INVENTION

This invention relates to a compound according to general formula (I), which acts as a bradykinin (BK) B2 receptor antagonist; to a pharmaceutical composition containing one or more of the compound(s) of the invention; to a combination preparation containing at least one compound of the invention and at least one further active pharmaceutical ingredient; and to uses of said compound(s), including the use as a medicament.

BACKGROUND OF THE INVENTION

BK is a peptide hormone that participates in inflammatory processes by activation of endothelial cells leading to vasodilation, increased vascular permeability, production of nitric oxide, and mobilization of arachidonic acid. BK also stimulates sensory nerve endings causing a burning dysaesthesia. Thus, the classical parameters of inflammation (e.g. redness, heat, swelling and pain) can all result from BK formation. BK is a short-lived component of the kallikrein-kinin system. The concentration of circulating BK is maintained at a low level under normal physiological conditions and may be rapidly increased under pathological situations by the enzymatic degradation of the circulating glycoprotein precursors called kininogens. The two most potent kininogen-metabolising enzymes are the trypsin-like serine proteases plasma kallikrein and tissue kallikrein. The precursors of these enzymes are normally present in all tissues and are ready to be activated by physiological or pathophysiological processes. (Sainz, I. M. et al *Thromb. Haemost.* 2007, 98, 77-83). The BK B2 receptor is constitutively expressed in most cell and tissue types and mediates most of the known effects of BK when this is produced in plasma or tissues. (Regoli, D. et al *Pharmacol. Rev.* 1980, 32, 1-46). A large number of in vivo studies have shown that agents that blockade the BK B2 receptor provide therapeutic benefits in pathological conditions such as asthma, allergic rhinitis, pancreatitis, osteoarthritis, traumatic brain injury, Alzheimer's disease, and angioedema.

Numerous peptide and non-peptide antagonists of BK B2 receptor have been described in the prior art. Quinoline derivatives having activity as BK B2 receptor antagonists are, for example, disclosed in WO 2014/159637, WO 2010/031589, WO 2008/116620, WO 2006/40004, WO 03/103671, WO 03/87090, WO 00/23439, WO 00/50418, WO 99/64039, WO 97/41104, WO 97/28153, WO 97/07115, WO 96/13485, EP 0 795 547, EP 0 796 848, EP 0 867 432, and EP 1 213 289. However, these compounds showed a number of deficiencies hampering their utility as a drug, including low metabolic stability, low bioavailability, formation of glutathione adducts and bioactivation (toxicity) as disclosed in WO 2014/159637.

In view of the deficits of the prior art compounds and the severe conditions associated with a pathophysiological level of BK, both acute and chronic, there is a need for novel BK B2 receptor antagonists.

SUMMARY AND DESCRIPTION OF THE INVENTION

The present invention was made in view of the prior art and the needs described above, and, therefore, the object of the present invention is to provide novel BK B2 receptor antagonists according to general formula (I), preferably BK B2 receptor antagonists having one or more improved properties, e.g. an improved pharmacokinetic and/or physiochemical property, including bioavailability, solubility, metabolic stability, and a LADME (liberation, absorption, distribution, metabolism, and excretion) property. Other objects of the present invention are to provide a pharmaceutical composition comprising at least one BK B2 receptor antagonist as described herein; a combination preparation containing at least one compound of the invention and at least one further active pharmaceutical ingredient; and uses of the compound(s) of the invention, including the use as a medicament.

These objects are solved by the subject matter of the attached claims as will become apparent upon reference to the following description and definitions.

The present invention relates to:
[1] a compound of the general formula (I):

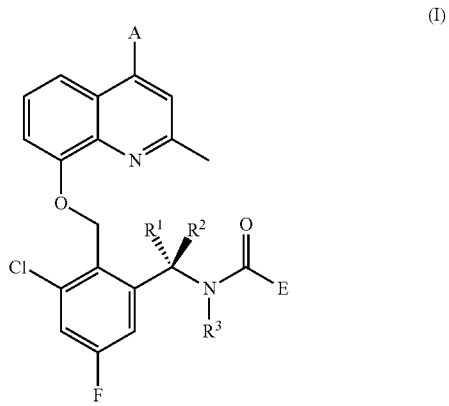

or a salt thereof, wherein
A represents a group:

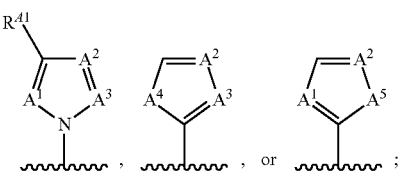

$A^1$ is N, or CH;
$A^2$ is N, or C—$R^{A2}$;
$A^3$ is N, or C—$R^{A3}$;
$A^4$ is NH, O, or S;
$A^5$ is N—$R^{A5}$;
$R^{A1}$ represents a hydrogen atom or a methyl group;
$R^{A2}$ and $R^{A3}$ each, independently of one another, represents a hydrogen atom, halogen atom, OH, CN, $NH_2$;

($C_1$-$C_3$)alkyl, which may be substituted by one or more, identical or different, group(s) selected from a halogen atom, OH, =O, and $NH_2$; ($C_1$-$C_3$)alkoxy, which may be substituted by one or more, identical or different, group(s) selected from a halogen atom, OH, =O, and $NH_2$; ($C_2$-$C_5$)alkoxyalkyl, which may be substituted by one or more, identical or different, group(s) selected from a halogen atom, OH, =O, and $NH_2$; $C(O)NR^{B1}R^{B2}$; or $NR^{B1}R^{B2}$;

$R^{B1}$, $R^{B2}$ and $R^{A5}$ each, independently of one another, represents a hydrogen atom or a ($C_1$-$C_3$)alkyl group, which may be substituted by one or more, identical or different, group(s) selected from a halogen atom, OH, =O, and $NH_2$;

$R^1$ represents a ($C_1$-$C_3$)alkyl or ($C_2$-$C_5$)alkoxyalkyl group, which alkyl group or alkoxyalkyl group may be substituted by one or more, identical or different, group(s) selected from a deuterium atom, halogen atom, OH, =O, and $NH_2$;

$R^2$ represents a hydrogen atom or a deuterium atom;

$R^3$ represents a hydrogen atom, ($C_1$-$C_3$)alkyl, or ($C_1$-$C_3$) haloalkyl group;

E represents $CR^{E1}R^{E2}R^{E3}$ or Hce;

Hce represents a mono- or bicyclic, partially unsaturated or aromatic heterocycle having 3 to 10 C atoms and 1 to 4 heteroatom(s) each, independently of one another, selected from N, O or S, which heterocycle is unsubstituted or may be mono-, di- or trisubstituted, at each occasion independently, by a halogen atom, OH, G, $NR^{C1}R^{C2}$ and/or =O;

$R^{C1}$ and $R^{C2}$ each, independently of one another, represents a hydrogen atom or a ($C_1$-$C_3$)alkyl group;

G represents a ($C_1$-$C_6$)alkyl group, in which 1 to 7H atoms may, at each occasion independently, be replaced by a halogen atom, $OR^{G1}$, CN, $NR^{G2}R^{G3}$ or ($C_3$-$C_6$)cycloalkyl, and/or in which one $CH_2$ group, or two non-adjacent $CH_2$ groups, may be replaced by O, C(O), OC(O), C(O)O, C(O)NH, NH, S, SO, $SO_2$ and/or by a CH=CH group;

$R^{G1}$, $R^{G2}$, and $R^{G3}$ each, independently of one another, represents a hydrogen atom, ($C_1$-$C_4$)alkyl, ($C_1$-$C_4$) haloalkyl, ($C_1$-$C_4$) hydroxyalkyl, ($C_1$-$C_4$) heteroalkyl, or ($C_3$-$C_6$) cycloalkyl group;

$R^{E1}$ and $R^{E2}$ each, independently of one another, represents a hydrogen atom, halogen atom, or G; or $R^{E1}$ and $R^{E2}$ taken together form =O or Cyc;

$R^{E3}$ represents a hydrogen atom, halogen atom, G, OG or OH; and

Cyc represents a mono- or bicyclic, saturated or partially unsaturated 3- to 10-membered cycloalkyl group or 4- to 10-membered heterocycloalkyl group having 1 to 3 heteroatom(s) each, independently of one another, selected from N, O or S, which cycloalkyl or heterocycloalkyl group is unsubstituted or may be mono-, di-, tri-, or tetrasubstituted, at each occasion independently, by a halogen atom, OH, G, $NR^{C1}R^{C2}$ and/or =O.

Compounds are usually described herein using standard nomenclature or the definitions presented below. For compounds having asymmetric centers, it should be understood that, unless otherwise specified, all of the optical isomers and mixtures thereof are encompassed. Compounds with two or more asymmetric elements can also be present as mixtures of diastereomers. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms. It will be apparent that the compound of the invention may, but need not, be present as a hydrate, solvate or non-covalent complex. In addition, the various crystal forms and polymorphs are within the scope of the present invention, as are prodrugs of the compound of the invention. Recited compounds are further intended to encompass compounds in which one or more atoms are replaced with an isotope, i.e., an atom having the same atomic number but a different mass number. By way of general example, and without limitation, isotopes of hydrogen include tritium and deuterium and isotopes of carbon include $^{11}C$, $^{13}C$, and $^{14}C$.

Compounds according to the formulas provided herein, which have one or more stereogenic center(s), have an enantiomeric excess of at least 50%. For example, such compounds may have an enantiomeric excess of at least 60%, 70%, 80%, 85%, 90%, 95%, or 98%. Some embodiments of the compounds have an enantiomeric excess of at least 99%. It will be apparent that single enantiomers (optically active forms) can be obtained by asymmetric synthesis, synthesis from optically pure precursors or by resolution of the racemates. Resolution of the racemates can be accomplished, for example, by conventional methods such as crystallization in the presence of a resolving agent, or chromatography, using, for example a chiral HPLC column.

The compound according to the invention is described herein using a general formula that includes variables such as, e.g. A, $A^1$-$A^5$, E, $R^1$-$R^3$, $R^{A1}$-$R^{A5}$, $R^{B1}R^{B2}$, $R^{C}R^{C2}$, $R^{E1}$-$R^{E3}$, and $R^{G1}$-$R^{G3}$. Unless otherwise specified, each variable within such a formula is defined independently of any other variable, and any variable that occurs more than one time in a formula is defined independently at each occurrence. Thus, for example, if a group is shown to be substituted with 0-2 R*, the group may be unsubstituted, or substituted with 1 or 2 group(s) R*, wherein R* at each occurrence is selected independently from the corresponding definition of R*. Also, combinations of substituents and/or variables are permissible only if such combinations result in stable compounds, i.e., compounds that can be isolated, characterized and tested for biological activity.

As used herein a wording defining the limits of a range of length such as, e. g., "from 1 to 5" means any integer from 1 to 5, i.e. 1, 2, 3, 4 and 5. In other words, any range defined by two integers explicitly mentioned is meant to comprise and disclose any integer defining said limits and any integer comprised in said range. For example, the term "$C_1$-$C_3$" refers to 1 to 3, i.e. 1, 2 or 3, carbon atoms; and the term "$C_1$-$C_6$" refers to 1 to 6, i.e. 1, 2, 3, 4, 5 or 6, carbon atoms. Further, the prefix "($C_{x-y}$)" as used herein means that the chain, ring or combination of chain and ring structure as a whole, indicated in direct association of the prefix, may consist of a minimum of x and a maximum of y carbon atoms (i.e. x<y), wherein x and y represent integers defining the limits of the length of the chain (number of carbon atoms) and/or the size of the ring (number of carbon ring atoms).

A "pharmacologically acceptable salt" of a compound disclosed herein is an acid or base salt that is generally considered in the art to be suitable for use in contact with the tissues of human beings or animals without excessive toxicity or carcinogenicity, and preferably without irritation, allergic response, or other problem or complication. Such pharmaceutical salts include mineral and organic acid salts of basic residues such as amines, as well as alkali or organic salts of acidic residues such as carboxylic acids.

Suitable pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—(CH$_2$)$_n$—COOH where n is any integer from 0 to 4 (i.e., 0, 1, 2, 3, or 4) and the like. Similarly, pharmaceutically acceptable cations include, but are not limited to sodium, potassium, calcium, aluminum, lithium and ammonium. Those of ordinary skill in the art will recognize further pharmacologically acceptable salts for the compounds provided herein. In general, a pharmacologically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two. Generally, the use of nonaqueous media, such as ether, ethyl acetate, ethanol, isopropanol or acetonitrile, is preferred.

A "substituent," as used herein, refers to a molecular moiety that is covalently bonded to an atom within a molecule of interest. For example, a substituent on a ring may be a moiety such as a halogen atom, an alkyl, haloalkyl, hydroxy, cyano, or amino group, or any other substituent described herein that is covalently bonded to an atom, preferably a carbon or nitrogen atom, that is a ring member.

The term "substituted," as used herein, means that any one or more hydrogen atom(s) on the designated atom or group (e.g. alkyl, alkoxy, alkoxyalkyl, cycloalkyl, heterocycloalkyl, heteroaryl) is replaced with a selection from the indicated substituents, provided that the designated atom's normal valence or the group's number of possible sites for substitution is not exceeded, and that the substitution results in a stable compound, i.e. a compound that can be isolated, characterized and tested for biological activity. When a substituent is oxo, i.e., =O, then 2 hydrogens on the atom are replaced. An oxo group that is a substituent of an aromatic carbon atom results in a conversion of —CH— to —C(=O)— and may lead to a loss of aromaticity. For example, a pyridyl group substituted by oxo is a pyridone. The indication mono-, di-, tri or tetrasubstituted denotes groups having one (mono), two (di), three (tri) or four substituents, provided that the substitution does not exceeded the number of possible sites for substitution and results in a stable compound. For example, a monosubstituted imidazolyl group may be an (imidazolidin-2-on)yl group and a disubstituted isoxazolyl group may be a ((3,5-dimethyl)isoxazolyl) group.

As used herein, "comprising", "including", "containing", "characterized by", and grammatical equivalents thereof are inclusive or open-ended terms that do not exclude additional, unrecited elements or method steps. Yet, "Comprising", etc. is also to be interpreted as including the more restrictive terms "consisting essentially of" and "consisting of", respectively.

As used herein, "consisting of" excludes any element, step, or ingredient not specified in the claim.

When trade names are used herein, it is intended to independently include the trade name product formulation, the generic drug, and the active pharmaceutical ingredient(s) of the trade name product.

In general, unless defined otherwise, technical and scientific terms used herein have the same meaning as commonly understood by one of ordinary skill in the art to which this invention belongs, and are consistent with general textbooks and dictionaries.

The expression alkyl or alkyl group denotes a saturated, straight-chain or branched hydrocarbon group that contains from 1 to 20 carbon atoms, preferably from 1 to 12 carbon atoms, more preferably from 1 to 6 carbon atoms, or the number of carbon atoms indicated in the prefix. If an alkyl is substituted, the substitution may take place, independently of one another, by mono-, di-, or tri-substitution of individual carbon atoms of the molecule, e.g. 1, 2, 3, 4, 5, 6, or 7 hydrogen atom(s) may, at each occasion independently, be replaced by a selection from the indicated substituents. The foregoing also applies if the alkyl group forms a part of a group, e.g. haloalkyl, hydroxyalkyl, alkylamino, alkoxy, or alkoxyalkyl. Examples of an alkyl group include methyl, ethyl, propyl, iso-propyl, n-butyl, iso-butyl, sec-butyl, tert-butyl, n-pentyl, iso-pentyl, n-hexyl, 2,2-dimethylbutyl, or n-octyl, and examples of a substituted alkyl group or a group where the alkyl forms a part of a group, include haloalkyl, e.g. a trifluoromethyl or a difluoromethyl group; hydroxyalkyl, e.g. hydroxymethyl or 2-hydroxyethyl group, and a methoxymethyl group. The term "(C$_{1-6}$) alkyl" includes, for example, H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)—, H$_3$C—CH$_2$—CH(CH$_2$CH$_3$)—, —CH$_2$CH$_2$CH$_2$CH$_2$CH$_2$CH$_3$, —CH(CH$_3$)CH$_2$CH$_2$CH$_2$CH$_3$, (H$_3$CH$_2$C)CH(CH$_2$CH$_2$CH$_3$)—, —C(CH$_3$)$_2$(CH$_2$CH$_2$CH$_3$), —CH(CH$_3$)CH(CH$_3$)CH$_2$CH$_3$, and —CH(CH$_3$)CH$_2$CH(CH$_3$)$_2$.

The expression alkoxy or alkoxy group refers to an alkyl group singular bonded to oxygen, i.e.—O-alkyl. The term "(C$_1$-C$_6$) alkoxy" includes, for example, methoxy, ethoxy, n-propoxy, isopropoxy, n-butoxy, sec-butoxy, isobutoxy, tert-butoxy, n-pentyloxy, tert-amyloxy- or n-hexyloxy, and accordingly (C$_1$-C$_3$)alkoxy includes methoxy, ethoxy, n-propoxy, or isopropoxy.

The expression alkoxyalkyl or alkoxyalkyl group refers to an alkyl group singular bonded to one or more alkoxy group(s), e.g. -alkyl-O-alkyl or -alkyl-O-alkyl-O-alkyl. The term "(C$_2$-C$_5$) alkoxyalkyl" includes, for example, methoxymethyl, methoxyethoxymethyl, and 1-ethoxyethyl.

The expression haloalkyl or haloalkyl group refers to an alkyl group in which one, two, three or more hydrogen atoms have been replaced independently of each other by a halogen atom. The term "(C$_1$-C$_3$) haloalkyl" includes, for example, fluoromethyl, difluoromethyl, trifluoromethyl, chloromethyl, dichloromethyl, bromomethyl, dibromomethyl, iodomethyl, (1- or 2-)haloethyl (e.g. (1- or 2-)fluoroethyl or (1- or 2-)chloroethyl), (2- or 3-) halopropyl (e.g. (2- or 3-) fluoropropyl or (2- or 3-) chloropropyl).

The expression hydroxyalkyl or hydroxyalkyl group refers to an alkyl group in which one, two, three or more hydrogen atoms have been replaced independently of each other by a hydroxy (OH) group. The term "(C$_1$-C$_4$) hydroxyalkyl" includes, for example, hydroxymethyl, hydroxyethyl, hydroxypropyl and hydroxybutyl.

As used herein, the expression heteroalkyl or heteroalkyl group refers to an alkyl group, straight chain or branched as defined above, in which one or more, preferably 1, 2, 3 or 4, carbon atom(s) has/have been replaced, each independently of one another, by an oxygen, nitrogen, selenium, silicon or sulphur atom, preferably by an oxygen, sulphur or nitrogen atom, C(O), OC(O), C(O)O, C(O)NH, NH, SO, SO$_2$ or by a CH=CH group, wherein said heteroalkyl group may be substituted. For example, a "($C_1$-$C_4$)heteroalkyl group" contains from 1 to 4, e.g. 1, 2, 3 or 4, carbon atoms and 1, 2, 3 or 4, preferably 1, 2 or 3, heteroatoms selected from oxygen, nitrogen and sulphur (especially oxygen and nitrogen). Examples of an heteroalkyl group include alkylamino, dialkylaminoalkyl, acyl, acylalkyl, alkoxycarbonyl, acyloxy, acyloxyalkyl, carboxyalkylamide, alkoxycarbonyloxy, alkylcarbamoyl, alkylamido, alkylcarbamoylalkyl, alkylamidoalkyl, alkylcarbamoyloxyalkyl, alkylureidoalkyl, alkoxy, alkoxyalkyl, or alkylthio group. The expression alkylthio or alkylthio group refers to an alkyl group, in which one or more non-adjacent $CH_2$ group(s) are replaced by sulfur, wherein the alkyl moiety of the alkylthio group may be substituted. Specific examples of a heteroalkyl group include acyl, methoxy, trifluoromethoxy, ethoxy, n-propyloxy, isopropyloxy, tert-butyloxy, methoxymethyl, ethoxymethyl, methoxyethyl, methylamino, ethylamino, dimethylamino, diethylamino, isopropylethylamino, methylaminomethyl, ethylaminomethyl, diisopropylaminoethyl, dimethylaminomethyl, dimethylaminoethyl, acetyl, propionyl, butyryloxy, acetyloxy, methoxycarbonyl, ethoxycarbonyl, isobutyrylaminomethyl, N-ethyl-N-methylcarbamoyl, N-methylcarbamoyl, cyano, nitrile, isonitrile, thiocyanate, isocyanate, isothiocyanate and alkylnitrile.

The expression cycloalkyl or cycloalkyl group refers to a saturated carbocyclic ring group comprising one or more rings (preferably 1 or 2) and containing from 3 to 14 ring carbon atoms, preferably from 3 to 10 (more preferably 3, 4, 5, 6 or 7) ring carbon atoms; the cycloalkyl group may be substituted and can be bonded as a substituent via every suitable position of the ring system.

Examples of cycloalkyl include monocyclic hydrocarbon rings, bicyclic hydrocarbon rings and spiro-hydrocarbon rings. In a bicyclic cycloalkyl group, two rings are joined together so that they have at least two carbon atoms in common. In a spiro-hydrocarbon ring, 2 or 3 rings are linked together by one common atom carbon atom (spiro-atom). If a cycloalkyl is substituted, the substitution may take place, independently of one another, by mono- or di-substitution of individual ring carbon atoms of the molecule, and the cycloalkyl group as a whole may carry 1, 2, 3, or 4 substituents from the indicated selection of substituents, i.e. 1, 2, 3, or 4 hydrogen atom(s) of the carbon ring atoms may, at each occasion independently, be replaced by a substituent selected from the indicated list of substituents thereby resulting in a mono-, di-, tri-, or tetrasubstituted cycloalkyl group. Examples of cycloalkyl include cyclopropyl, cyclobutyl, cyclopentyl, cyclohexyl, cycloheptyl, bicyclo[2.2.0]hexyl, bicyclo[3.2.0]heptyl, bicyclo[3.2.1]octyl, bicyclo[2.2.2]octyl, bicyclo[4.3.0]nonyl (octahydroindenyl), bicyclo[4.4.0]decyl (decahydronaphthyl), bicyclo[2.2.1]heptyl (norbornyl), bicyclo[4.1.0]heptyl (norcaranyl), bicyclo[3.1.1]heptyl (pinanyl), spiro[2.5]octyl, and spiro[3.3]heptyl. If a cycloalkyl is partially unsaturated, the group contains one, two or more double bonds, such as, for example, a cycloalkenyl group, including cyclopropenyl, cyclobutenyl, cyclopentenyl, cyclohexenyl, cycloheptenyl, cyclobutadienyl, cyclopentadienyl, cyclohexadienyl, bicyclo[2.2.1]heptadienyl, and spiro[4,5]decenyl.

The expression heterocycloalkyl or heterocycloalkyl group refers to a cycloalkyl group, saturated or partially unsaturated, as defined above, in which one or more, preferably 1, 2 or 3, ring carbon atom(s) has/have been replaced each independently of one another by an oxygen, nitrogen or sulphur atom, preferably oxygen or nitrogen, or by NO, SO or $SO_2$; the heterocycloalkyl may be substituted and can be bonded as a substituent via every suitable position of the ring system; at least one carbon atom must be present between two oxygen atoms and between two sulphur atoms or between an oxygen and a sulphur atom; and the ring as a whole must have chemical stability. A heterocycloalkyl group has preferably 1 or 2 ring(s) containing from 3 to 10 (more preferably 3, 4, 5, 6 or 7, and most preferably 5, 6 or 7) ring atoms. Examples of heterocycloalkyl include aziridinyl, oxiranyl, thiiranyl, oxaziridinyl, dioxiranyl, azetidinyl, oxetanyl, thietanyl, diazetidinyl, dioxetanyl, dithietanyl, pyrrolidinyl, tetrahydrofuranyl, thiolanyl, azolyl, thiazolyl, isothiazolyl, imidazolidinyl, pyrazolidinyl, oxazolidinyl, isoxazolidinyl, thiazolidinyl, isothiazolidinyl, dioxolanyl, dithiolanyl, piperazinyl, morpholinyl, thiomorpholinyl, trioxanyl, azepanyl, oxepanyl, thiepanyl, homopiperazinyl, urotropinyl, oxazolidinonyl, dihydropyrazolyl, dihydropyrrolyl, dihydropyrazinyl, dihydropyridyl, dihydropyrimidinyl, dihydrofuryl, dihydropyranyl, and examples of substituted heterocycloalkyl include lactam, lactone and cyclic imide ring systems.

The expressions aryl, Ar or aryl group refer to an aromatic group that contains one or more aromatic rings containing from 6 to 14 ring carbon atoms ($C_6$-$C_{14}$), preferably from 6 to 10 ($C_6$-$C_{10}$), more preferably 6 ring carbon atoms; the aryl may be substituted and can be bonded as a substituent via every suitable position of the ring system. Examples of aryl include phenyl, naphthyl, bi-phenyl, indanyl, indenyl, anthracenyl, phenanthrenyl, tetrahydronaphthyl and fluorenyl.

The expression heteroaryl or heteroaryl group refers to an aromatic group that contains one or more aromatic rings containing from 5 to 14 ring atoms, preferably from 5 to 10 (more preferably 5 or 6) ring atoms, and contains one or more (preferably 1, 2, 3 or 4) oxygen, nitrogen, phosphorus or sulphur ring atoms (preferably O, S or N); the heteroaryl may be substituted and can be bonded as a substituent via every suitable position of the ring system. Examples of an unsubstituted heteroaryl group include 2-pyridyl, 2-imidazolyl, 3-phenylpyrrolyl, thiazolyl, oxazolyl, triazolyl, tetrazolyl, isoxazolyl, indazolyl, indolyl, benzimidazolyl, pyridazinyl, quinolinyl, purinyl, carbazolyl, acridinyl, pyrimidyl, 2,3'-bifuryl, 3-pyrazolyl and isoquinolinyl.

The expression heterocycle denotes ring systems, which include the above defined heterocycloalkyl and heteroaryl ring systems, e.g. a partially unsaturated heterocycle is synonymous with a partially unsaturated heterocycloalkyl and an aromatic heterocycle is synonymous with a heteroaryl. The heterocycle may be substituted and can be bonded as a substituent via every suitable position of the ring system. Examples of a partially unsaturated or aromatic heterocycle include oxetenyl, thietenyl, azetinyl, 2,3-dihydrofuranyl, 2,5-dihydrofuranyl, 2,5-dihydrothiophenyl, 2,5-dihydro-1H-pyrrolyl, furanyl, thiophenyl, pyrrolyl, benzo[b]furanyl, benzo[b]thiophenyl, indolyl, benzo[c]pyrrolyl, benzo[a]pyrrolyl, imidazolyl, pyrazolyl, oxazolyl, isoxazolyl, thiazolyl, isothiazolyl, 1,2,3-triazolyl, 1,2,4-triazolyl, tetrazolyl, dihydropyridinyl, oxazinyl, pyridinyl, dihydropyranyl, azepinyl, tetrahydropyranyl, dihydrothiopyranyl, quinolinyl, isoquinolinyl, quinazolinyl, pyridazinyl, pyrimidinyl, pyrazinyl, purinyl, and pteridinyl.

The general term ring as used herein, unless defined otherwise, includes the cyclic groups defined herein above, e.g. a cycloalkyl group, heterocycloalkyl group, aryl group, heteroaryl group, and heterocycle.

The expression halogen or halogen atom as used herein means fluorine, chlorine, bromine, or iodine.

The expression heteroatom as used herein, preferably denotes an oxygen, nitrogen or sulphur atom, more preferably a nitrogen or oxygen atom.

The term "8-benzyloxy-quinoline", as used herein, refers to compounds of general formula (I) provided herein, as well as salts and preferably pharmaceutically acceptable salts thereof. It will be apparent that such compounds may be further substituted as indicated.

The present invention preferably relates to one or more of the following:

[2] the compound or salt according to [1] above, wherein A represents:

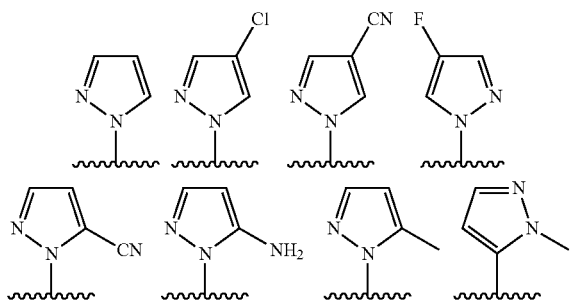
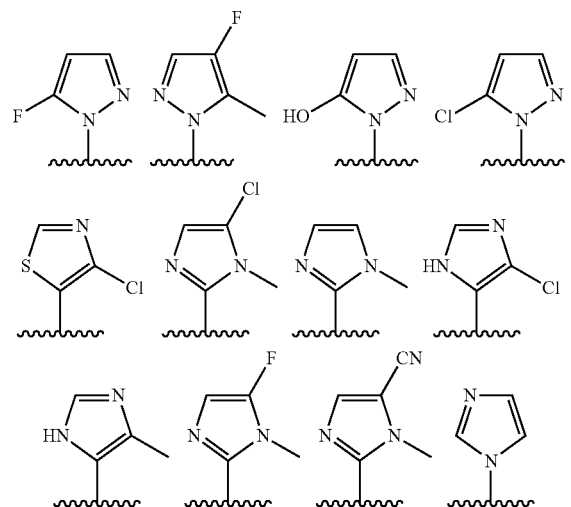
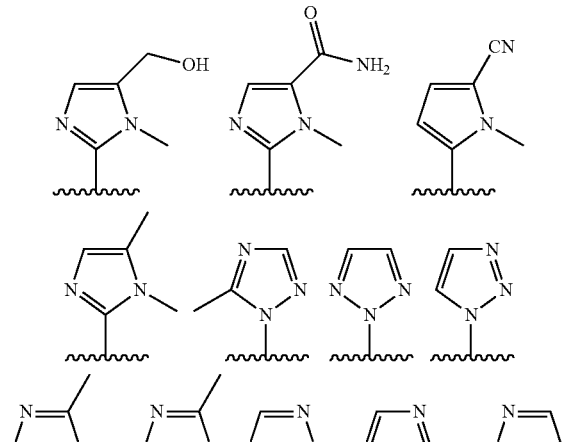
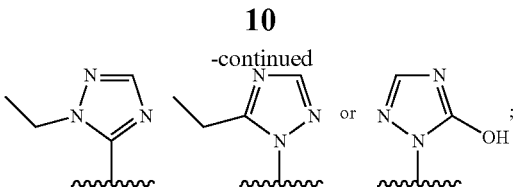

[3] the compound or salt according to [1] or [2], wherein A represents:

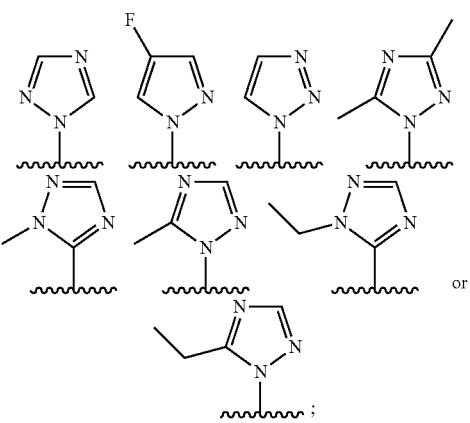

[4] the compound or salt according to any one of [1] to [3], wherein A represents:

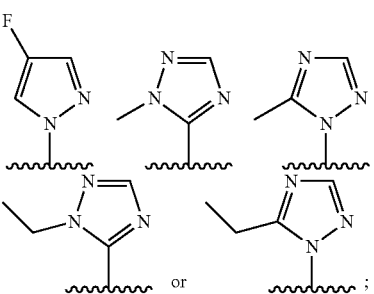

[5] the compound or salt according to any one of [1] to [4], wherein R represents a $(C_1-C_2)$alkyl or $(C_2-C_4)$alkoxyalkyl group, which alkyl group or alkoxyalkyl group may be substituted by one or more, identical or different, group(s) selected from a deuterium atom, halogen atom, and OH;

[6] the compound or salt according to any one of [1] to [5], wherein R represents a methyl, ethyl, methoxymethyl, methoxyethyl, or ethoxymethyl group, which may be substituted by one or more, identical or different, group(s) selected from a deuterium atom, halogen atom, and OH;

[7] the compound or salt according to any one of [1] to [6], wherein $R^1$ represents $CH_3$, $C_2H_5$, $CD_3$, $C_2D_5$, $CH_2OH$, $CH_2F$, $CHF_2$, $CF_3$, $CH_2CH_2OH$, $CH_2CH_2F$, $CH_2CF_3$, $CH_2OCH_3$, $CH_2OCHF_2$, or $CH_2OCF_3$;

[8] the compound or salt according to any one of [1] to [7], wherein $R^1$ represents $CH_3$, $C_2H_5$, $CD_3$, or $CH_2OH$;

[9] the compound or salt according to any one of [1] to [8], wherein $R^3$ represents a hydrogen atom or a methyl group;

[10] the compound or salt according to any one of [1] to [9], wherein $R^2$ represents a hydrogen atom;

[11] the compound or salt according to any one of [1] to [9], wherein $R^2$ represents a deuterium atom;

[12] the compound or salt according to any one of [1] to [11], wherein E is $CR^{E1}R^{E2}R^{E3}$ and each of $R^{E1}$, $R^{E2}$, and $R^{E3}$ is defined as in [1];
[13] the compound or salt according to any one of [1] to [12], wherein $R^{E1}$ represents a hydrogen atom, fluorine atom, methyl or ethyl;
[14] the compound or salt according to any one of [1] to [13], wherein $R^{E2}$ represents a hydrogen atom, fluorine atom, $(C_1-C_6)$alkyl group, preferably a $(C_1-C_3)$alkyl group, in which 1 to 4H atoms may, at each occasion independently, be replaced by a fluorine atom, OH, =O, or $NR^{C1}R^{C2}$; $(C_1-C_6)$alkoxy group, preferably a $(C_1-C_3)$alkoxy group, in which 1 to 4H atoms may, at each occasion independently, be replaced by a fluorine atom, OH, =O, $NR^{C1}R^{C2}$ or cyclopropyl; or a $(C_2-C_6)$alkoxyalkyl group, preferably a $(C_2-C_5)$ or $(C_2-C_4)$alkoxyalkyl group, in which 1 to 5H atoms may, at each occasion independently, be replaced by a fluorine atom, OH, =O, $NR^{C1}R^{C2}$ or cyclopropyl; and each of $R^{C1}$ and $R^{C2}$ is defined as in [1];
[15] the compound or salt according to any one of [1] to [14], wherein $R^{E3}$ represents a hydrogen atom, fluorine atom, OH, $(C_1-C_6)$alkyl group, preferably a $(C_1-C_3)$alkyl group, in which 1 to 5H atoms may, at each occasion independently, be replaced by a fluorine atom, OH, =O, or $NR^{C1}R^{C2}$; $(C_1-C_6)$alkoxy group, in which 1 to 5H atoms may, at each occasion independently, be replaced by a fluorine atom, OH, =O, $NR^{C1}R^{C2}$ or cyclopropyl; a $(C_2-C_6)$alkoxyalkyl group, preferably a $(C_2-C_5)$ or $(C_2-C_4)$ alkoxyalkyl group, in which 1 to 5H atoms may, at each occasion independently, be replaced by a fluorine atom, OH, =O, $NR^{C1}R^{C2}$ or cyclopropyl; and each of $R^{C1}$ and $R^{C2}$ is defined as in [1];
[16] the compound or salt according to [12], wherein $R^{E1}$ and $R^{E2}$ are taken together to form =O or Cyc, wherein the Cyc is selected from cyclopropyl, cyclobutyl, cyclopentyl, oxetanyl, tetrahydrofuranyl, tetrahydro-2H-pyranyl, 1,3-dioxolanyl, morpholinyl, azetidinyl pyrrolidinyl, piperidinyl, piperazinyl, (imidazolidin-2-on)yl and (oxazolidin-2-on)yl, and is unsubstituted or may be mono-, di- or trisubstituted, at each occasion independently, by a halogen atom, OH, G, $NR^{C1}R^{C2}$ and/or =O;
[17] the compound or salt according to [16], wherein the Cyc is unsubstituted or may be mono-, di- or trisubstituted, at each occasion independently, by a fluorine atom, OH, $(C_1-C_3)$alkyl, $(C_1-C_3)$alkoxy, $NR^{C1}R^{C2}$ and/or =O; and each of $R^{C1}$ and $R^{C2}$ is defined as in [1];
[18] the compound or salt according to [16] or [17], wherein the Cyc is an oxetanyl, tetrahydrofuranyl, 1,3-dioxolanyl, morpholinyl, azetidinyl, pyrrolidinyl, piperidinyl, piperazinyl, (imidazolidin-2-on)yl or (oxazolidin-2-on)yl, which is unsubstituted or may be mono-, di- or trisubstituted, at each occasion independently, by a fluorine atom, OH, $(C_1-C_3)$alkyl and/or $(C_1-C_3)$alkoxy;
[19] the compound or salt according to any one of [16] to [18], wherein $R^{E3}$ represents a hydrogen atom, fluorine atom, OH or a $(C_1-C_3)$alkyl group;
[20] the compound or salt according to any one of [1] to [11], wherein E represents Hce;
[21] the compound or salt according to [20], wherein Hce represents a monocyclic, partially unsaturated or aromatic heterocycle having 3 to 5 C atoms and 1 to 3 N atom(s); 3 to 5 C atoms, 1-2 N atom(s) and 1 O atom; or 3 to 5 C atoms, 1-2 N atom(s) and 1 S atom; which heterocycle is unsubstituted or may be mono-, di- or trisubstituted, at each occasion independently, by a halogen atom, OH, $(C_1-C_3)$alkyl, $(C_1-C_3)$haloalkyl, $(C_1-C_3)$alkoxy, $(C_1-C_3)$haloalkoxy and/or =O;

[22] the compound or salt according to [20] or [21], wherein E is selected from:

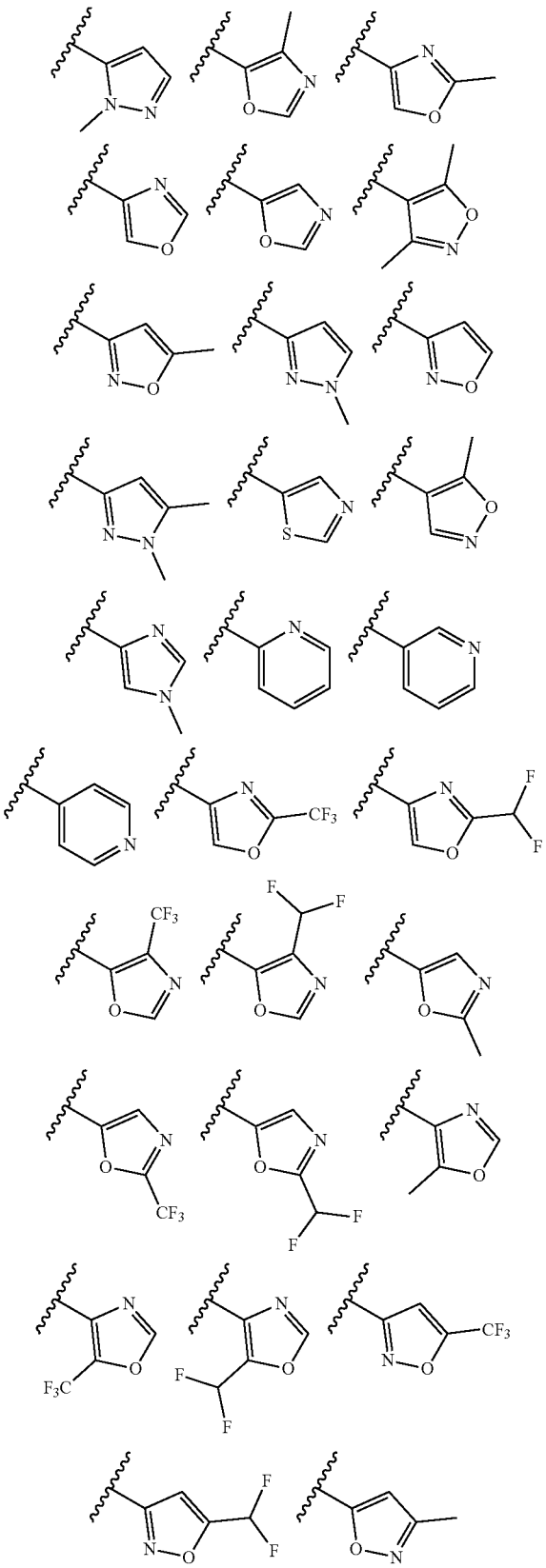

-continued
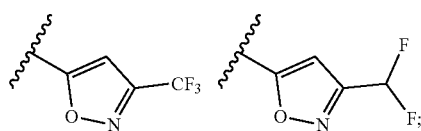
[23] the compound or salt according to any one of [1] to [15], and [20] to [22], wherein E represents a group:
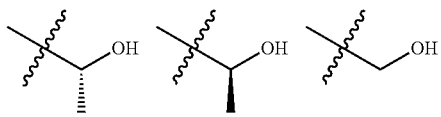
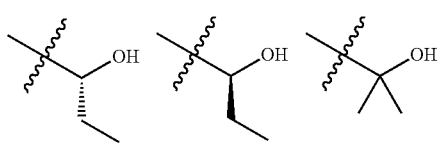
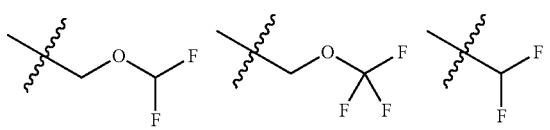
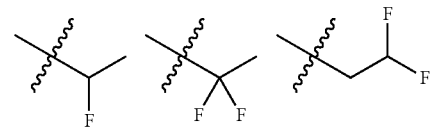
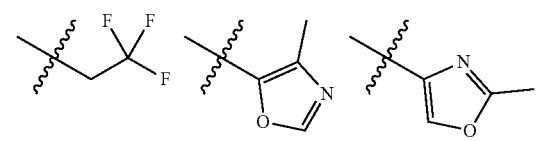
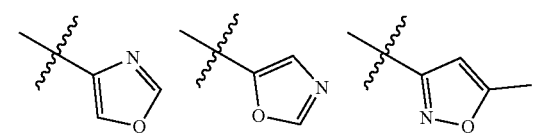
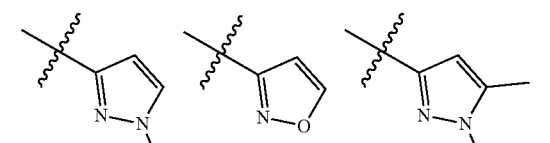
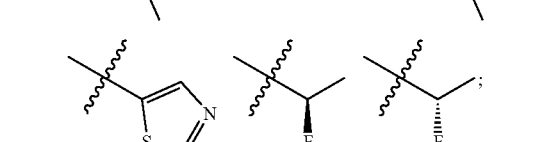
[24] the compound or salt according to any one of [1] to [23], wherein the compound is selected from the group:
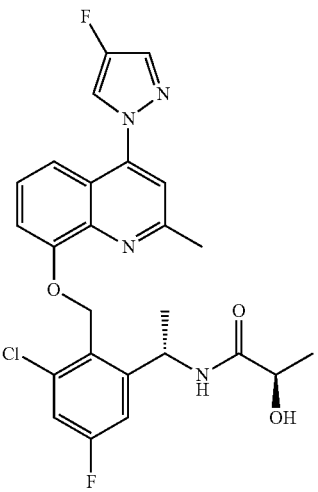
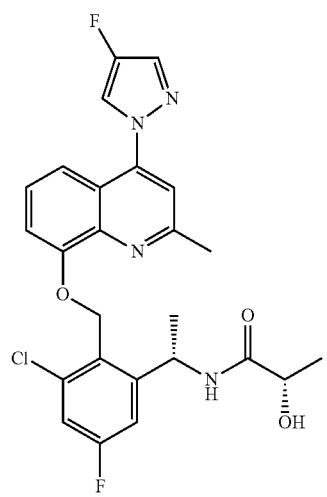
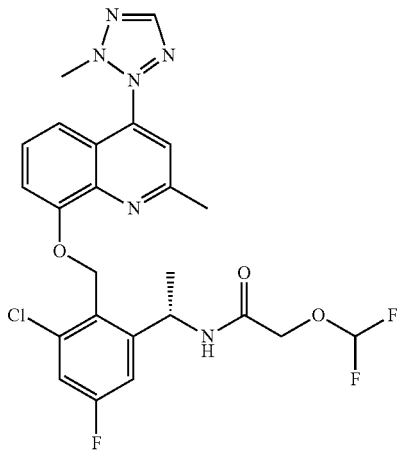

15
-continued
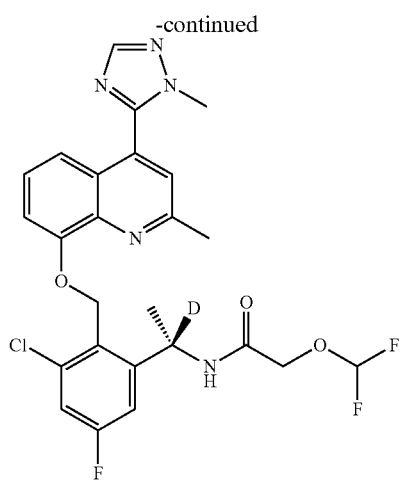
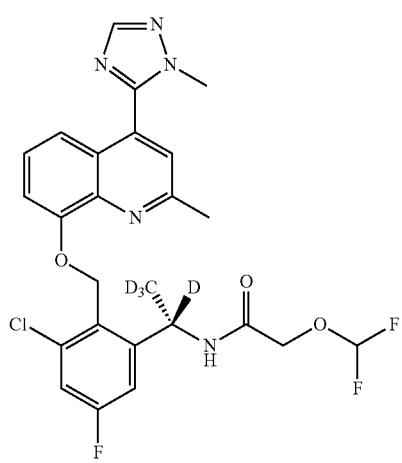
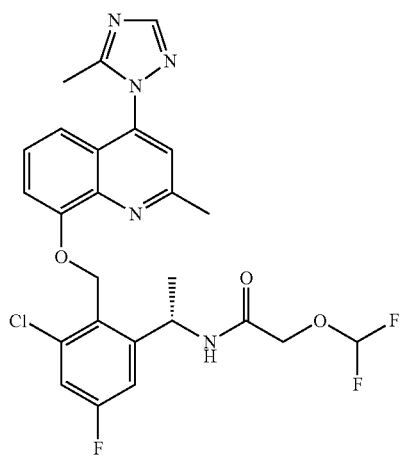
16
-continued
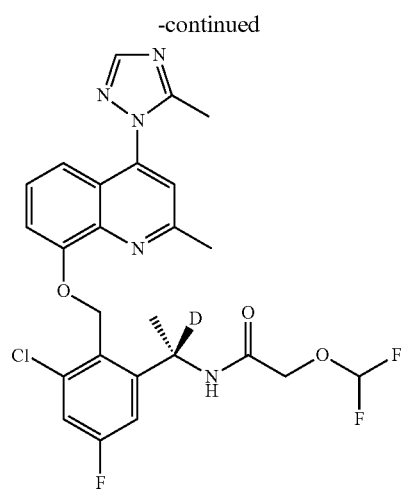
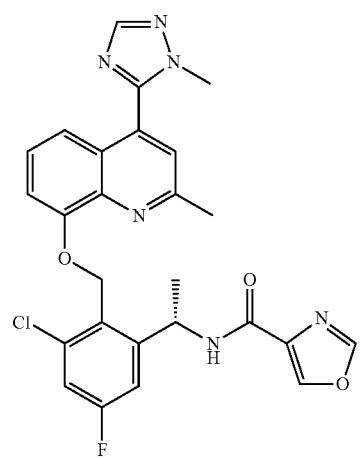
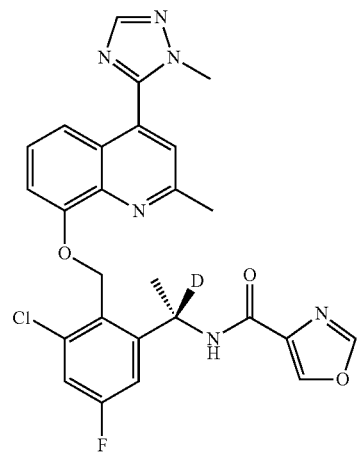

17
-continued
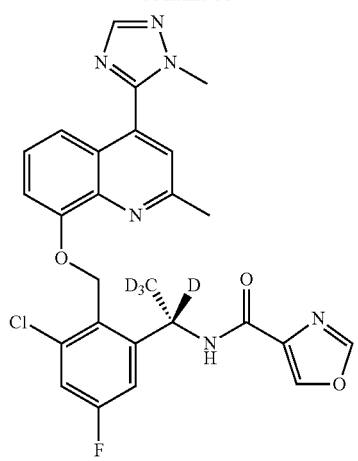
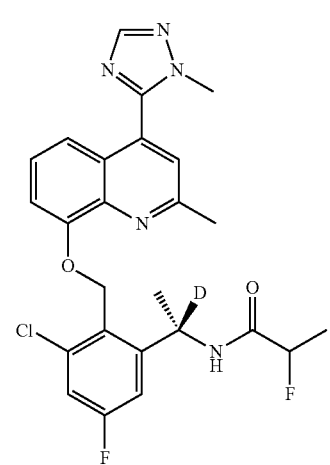
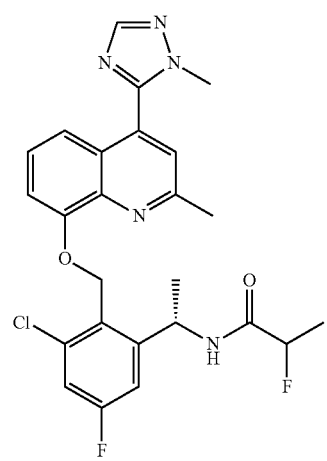
18
-continued
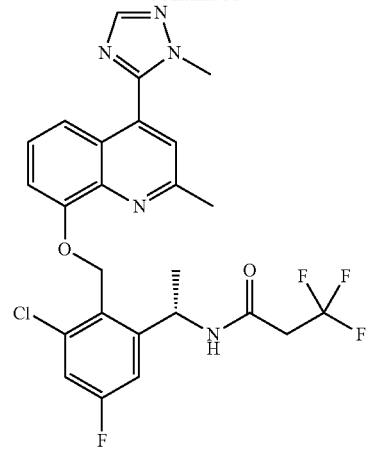
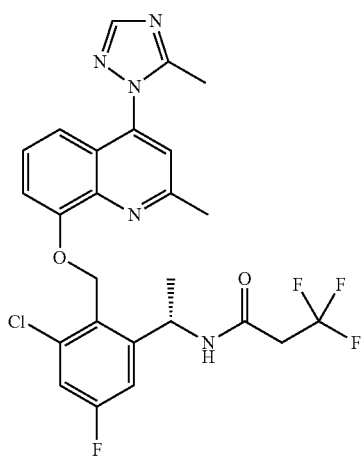
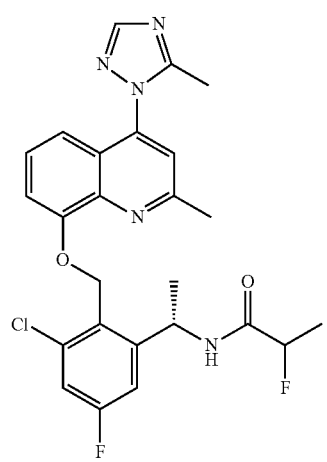

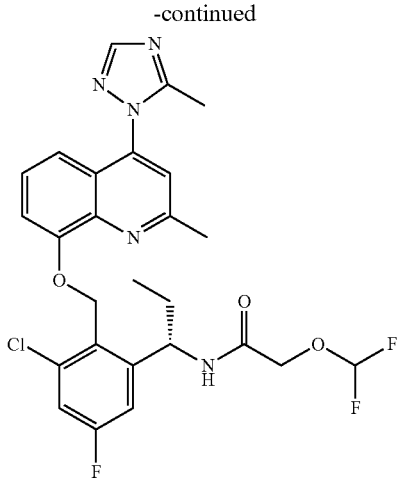
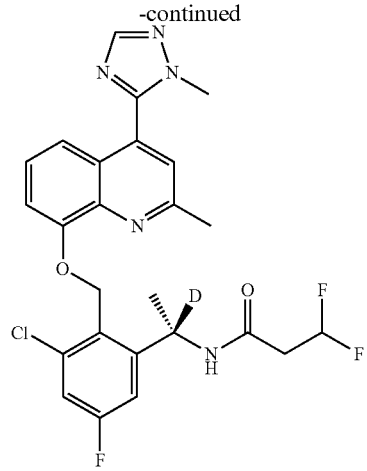
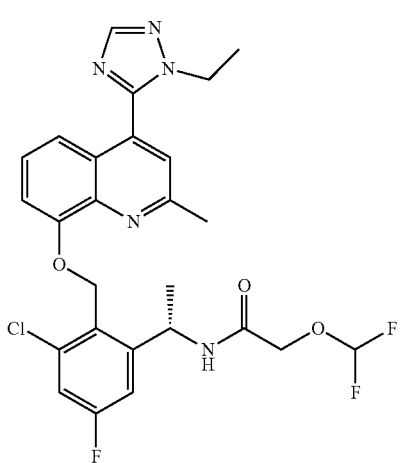
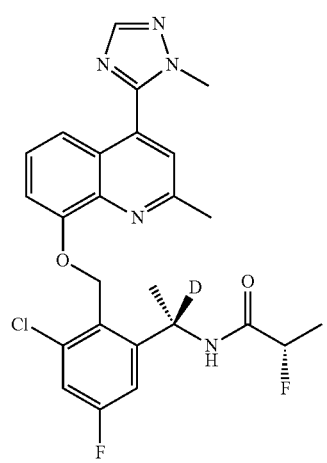
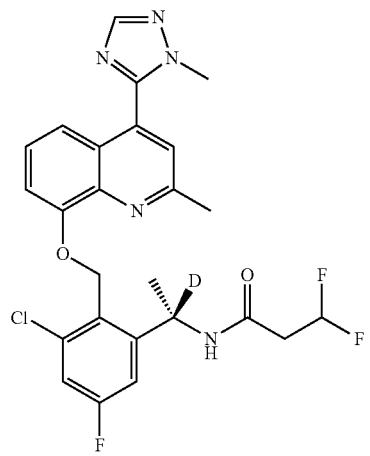
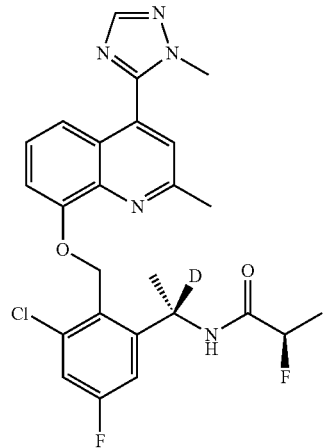

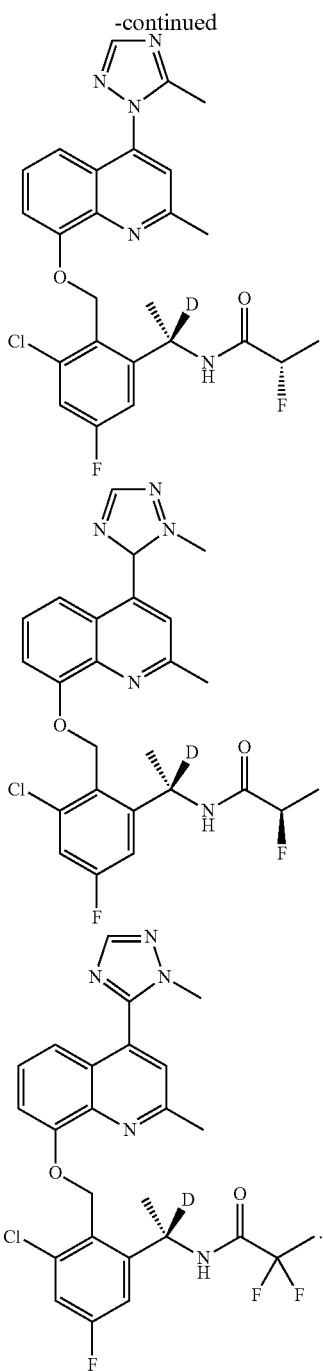

Compounds including suitable combinations of preferred embodiments, i.e. [2] to [23], of the compound according to general formula (I), or a salt thereof, are particularly preferred; e.g. a compound or salt thereof including a combination of [1], [3], [6] and [9] as disclosed herein. In other words, the present invention specifically encompasses all possible combinations of [1] to [23] as indicated above, which result in a stable compound.

The 8-benzyloxy-quinoline BK B2 receptor antagonist according to any one of [1] to [24] provided herein exhibits high activity on human BK B2 receptor, e. g. an inhibition constant $IC_{50}$ (half-maximal inhibitory concentration) for inhibition of BK-induced BK B2 receptor activity of 1 micromolar (μM) or less, e.g. of from 251 nanomolar (nM) to 1 μM; preferably an $IC_{50}$ of 250 nM or less, e.g. of from 51 nM to 250 nM; still more preferably an $IC_{50}$ of 50 nM or less; even more preferably an $IC_{50}$ of about 10 nM or less, or 1 nM or less in the assay mentioned below. The 8-benzyloxy-quinoline BK B2 receptor antagonists according to any one of [1] to [24] can exhibit a high activity on human BK B2 receptor, but also on BK B2 receptors of species other than human, e.g. rat, mouse, gerbil, guinea pig, rabbit, dog, cat, pig, or cynomolgus monkey.

The activity and more specifically the bioactivity of the compounds according to the present invention can be assessed using appropriate assays known to those skilled in the art, e.g. in vitro or in vivo assays. For instance, the inhibitory effect (expressed as $IC_{50}$ value) of a compound of the invention on the B2 receptor activity may be determined via intracellular calcium mobilization assay, such as the assay provided in Example 12, which is thus an embodiment of a standard in vitro B2 receptor-mediated assay. A particularly preferred compound or salt according to any one of [1] to [24] exhibits an $IC_{50}$ of 50 nM or less in a standard in vitro BK B2 receptor assay; e.g. the assay provided in Example 12.

The therapeutic use of a compound of general formula (I), its pharmacologically acceptable salt, solvate or hydrate; and also of a formulation or a pharmaceutical composition containing the same are within the scope of the present invention. The present invention also relates to the use of a compound of general formula (I) as active ingredient in the preparation or manufacture of a medicament.

A pharmaceutical composition according to the present invention comprises at least one compound of formula (I) or a pharmacologically acceptable salt thereof, preferably a compound according to any one of [1] to [24] or a salt thereof, and, optionally, at least one, i.e. one or more, carrier substance, excipient and/or adjuvant. In particular, a pharmaceutical composition of the invention can comprise one or more compound(s) according to the invention, e.g. a compound according to any one of [1] to [24], and, optionally, at least one carrier substance, excipient and/or adjuvant. The pharmaceutical composition may additionally comprise, for example, one or more of water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives.

Furthermore, one or more other active ingredient(s) may (but need not) be included in the pharmaceutical composition provided herein. For instance, one or more compound(s) of the invention may advantageously be contained in a combination preparation that contains at least one further active pharmaceutical ingredient. The further or supplemental active agent or active pharmaceutical ingredient is preferably an active agent or active pharmaceutical ingredient which has utility in the prevention or treatment of one or more condition(s) responsive to BK B2 receptor modulation, including a condition selected from the group comprising a skin disorder; eye disease; ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder;

cancer; hereditary disease; and edema. For instance, at least one compound or pharmaceutically acceptable salt of the invention may advantageously be contained in a combination preparation that includes an antibiotic, anti-fungal, or anti-viral agent, an anti histamine, a non-steroidal anti-inflammatory drug, a disease modifying anti-rheumatic drug, a cytostatic drug, a drug with smooth muscle activity modulatory activity, an antibody, or mixtures of the aforementioned as further or supplemental active agent or active pharmaceutical ingredient.

The pharmaceutical composition of the invention may be formulated for any appropriate manner of administration, including, for example, topical (e.g., transdermal or ocular), oral, buccal, nasal, vaginal, rectal or parenteral administration. The term parenteral as used herein includes subcutaneous, intradermal, intravascular (e.g., intravenous), intramuscular, spinal, intracranial, intrathecal, intraocular, periocular, intraorbital, intrasynovial and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions provided herein may be formulated as a lyophilizate. Formulation for topical administration may be preferred for certain conditions (e.g., in the treatment of skin conditions such as burns or itch). Briefly summarized, the pharmaceutical composition can, for example, be formulated as an aerosol, a cream, a gel, a pill, a capsule, a syrup, a solution, a transdermal patch or a pharmaceutical delivery device.

For the prevention and/or treatment of diseases mediated by BK or analogues thereof, the dose of the biologically active compound according to the invention may vary within wide limits and may be adjusted to individual requirements. Active compounds according to the present invention are generally administered in a therapeutically effective amount. Preferred doses range from about 0.1 mg to about 140 mg per kilogram of body weight per day (about 0.5 mg to about 7 g per patient per day). The daily dose may be administered as a single dose or in a plurality of doses. The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination (i.e. other drugs being used to treat the patient) and the severity of the particular disease undergoing therapy.

8-Benzyloxy-quinolines provided herein can also be used as antagonists of BK B2 receptors in a variety of applications, both in vitro and in vivo. BK B2 receptor antagonists according to the present invention may be used to inhibit the binding of BK B2 receptor ligands (e.g., BK) to BK B2 receptor in vitro or in vivo. This use includes, for example, a method of inhibiting binding of BK to BK B2 receptor in vitro or in vivo, wherein said method comprises contacting BK B2 receptor with at least one compound or salt according to the invention, e.g. according to any one of [1] to [39], under conditions and in an amount sufficient to detectably inhibit binding of BK or any other substance to BK B2 receptor. BK B2 receptor antagonists provided herein are preferably administered to a patient (e.g., a human) orally or topically, and are present within at least one body fluid or tissue of the patient while modulating BK B2 receptor activity.

BK B2 receptor antagonists according to any one of [1] to [24], the pharmaceutical composition, or the combination preparation according to the present invention are useful as a medicament. In particular, the BK B2 receptor antagonists, the pharmaceutical composition, or the combination preparation according to the present invention are useful in the treatment and/or prevention and/or prophylaxis of a condition or disease that is responsive to BK B2 receptor modulation. The condition or disease that is responsive to BK B2 receptor modulation may be a skin disorder; eye disease, ear disease; mouth, throat and respiratory disease; gastrointestinal disease; liver, gallbladder and pancreatic disease; urinary tract and kidney disease; disease of male genitale organs and female genitale organs; disease of the hormone system; metabolic disease; cardiovascular disease; blood disease; lymphatic disease; disorder of the central nervous system; brain disorder; musculoskeletal system disease; allergy disorder; pain; infectious disease; inflammatory disorder; injury; immunology disorder; cancer; hereditary disease; edema or capillary leak syndrome(s). In the following the above indicated diseases and conditions that are responsive to BK B2 receptor modulation are further specified.

Skin Disorders:

Within the present application the term "skin disorders" encompasses, but is not limited to, disorders such as skin aging, skin efflorescences including pressure sores, decubital ulcers, irritated, sensitive and dysaesthetic skin, erythema, rash, skin edema, psoriasis, eczema, lichen, bacterial, viral, fungal and parasites induced skin infections including furuncle, abscess, phlegmon, erysipelas, folliculitis and impetigo, lice, scabies and herpes simplex, acne, exanthema, dermatitis including atopic dermatitis, allergic contact dermatitis (Scholzen, T. E.; Luger, T. A. *Exp Dermatol.* 2004; 13 Suppl 4:22-6) neurodermatitis, radiation damage, sunburn, pruritus, itching, urticaria (EP0622361; Frigas, E.; Park, M. *Immunol. Allergy Cin. North Am.* 2006, 26, 739-51; Luquin, E.; Kaplan, A. P.; Ferrer, M. *Cin. Exp. Allergy* 2005, 35, 456-60; Kaplan, A. P.; Greaves, M. W. *J. Am. Acad. Dermatol.* 2005, 53, 373-88; quiz 389-92), psoriasis, mycosis, tissue ulceration, epidermolysis bullosa, wounds including abnormal wound healing, burns (Nwariaku, F. E.; Sikes, P. J.; Lightfoot, E.; Mileski, W. J.; Baxter, C. *Burns* 1996, 22, 324-7; Neely, A. N.; Imwalle, A. R.; Holder, I. A. *Burns* 1996, 22, 520-3), frostbite, skin inflammation and edema caused by venoms, alopecia, hair squama, corn, wart and panaris.

Eye Diseases:

Within the present application the term "eye diseases" encompasses, but is not limited to, inflammatory disorders such as scleritis, conjunctivitis, chemosis, iritis, iridocyclitis, uveitis, chorioretinitis, as well as disorders such as retinochoroidal circulatory disorders, bacterial eye infections, unspecific conjunctivitis and eye irritations, retinopathy of prematurity, proliferative vitreoretinopathy, macular degeneration (including age related macular degeneration and including both wet and dry forms), corneal diseases including corneal graft rejection, corneal injury, corneal scarring, corneal ulceration, corneal haze, keratoconus, glaucoma (preferably open angle glaucoma), myopia, ocular hypertension, ocular vessel damage, angiogenesis, eye fibrosis (e.g. anterior subcapsular fibrosis, posterior subcapsular opacities, posterior capsular opacities, corneal haze after laser surgery, subconjunctival scarring after glaucoma surgery), proliferative vitreoretinopathy (PVR), bacterial ocular infections including hordeolum and ptilosis.

Ear Diseases:

Within the present application the term "ear diseases" encompasses, but is not limited to, disorders such as Meniere's disease, inflammation of the middle ear, inflammation of the external auditory canal and acute hearing loss.

Mouth, Throat and Respiratory Diseases:

Within the present application the term "mouth, throat and respiratory diseases" encompasses, but is not limited to, disorders such as inflammation of the oral mucosa and gums including aphta and stomatitis, parodontitis, epiglottitis, pharyngitis, laryngotracheitis, tonsillitis, common cold, angina, rhinitis including seasonal allergic rhinitis or perennial allergic rhinitis, rhinorrea, sinusitis of whatever type, etiology or pathogenesis or sinusitis that is a member selected from the group consisting of purulent or nonpurulent sinusitis, acute and chronic sinusitis and ethmoid, frontal, maxillary or sphenoid sinusitis, expectoration, pneumoconiosis of whatever type or genesis, including for example aluminosis, anthracosis, asbestosis, chalicosis, siderosis, silicosis, tabacosis and, in particular, byssinosis, bronchitis, cough, trachitis, congestion, pneumonia, eosinophilc lung infiltrate, chronic eosinophilic pneumonia, idiopathic pulmonary fibrosis and other fibrotic lung diseases, treatment related fibrotic lung disease e.g. related to radiation, methotrexate, chemotherapy, amiodarone or nitrofurantoin, sarcoidosis, acute respiratory distress syndrome (ARDS), bronchoconstriction, asthma of whatever type (Akbary, A. M.; Wirth, K. J.; Scholkens, B. A. *Immunopharmacology* 1996, 33, 238-42; WO 00/75107 A2), etiology, or pathogenesis, or asthma that is a member selected from the group of atopic asthma, non-atopic asthma, allergic and non-allergic asthma, extrinsic asthma caused by environmental factors, intrinsic asthma caused by pathophysiologic disturbances, bronchial asthma, IgE-mediated asthma, essential asthma and essential asthma of unknown or inapparent cause, true asthma, emphysematous asthma, exercise-induced asthma, occupational asthma, infective asthma caused by bacterial, fungal, protozoal or viral infection, incipient asthma, wheezy infant syndrome, bronchial hyperreactivity, chronic obstructive pulmonary disease (COPD), COPD that is characterized by irreversible, progressive airways obstruction, acute respiratory distress syndrome (ARDS) and exacerbation of airways hyperreactivity consequent to other drug therapy, dyspnea, hyperoxic alveolar injury, pulmonary emphysema, pleurisy, tuberculosis, exposure to high altitude i.e. acute mountain sickness and preferably high altitude pulmonary edema (HAPE), resistant cough, bronchial hyporeactivity.

Gastrointestinal Diseases:

Within the present application the term "gastrointestinal diseases" encompasses, but is not limited to, disorders including esophagitis, gastritis, irritable stomach, gastric and duodenal ulcer, ileus, colon irritable, inflammatory bowel diseases including Crohn's disease and ulcerative colitis, enteritis, hypertensive gastro- and colopathy, colitis, peritonitis, appendicitis, rectitis, gastrointestinal hemorrhage caused by a portal hypertension, collateral circulation or hyperemia, postgastrectomy dumping-syndrome, digestion discomfort, diarrhea, hemorrhoids, worm diseases, abdominal colic and colic of parts of the gastrointestinal system.

Liver, gallbladder and pancreatic diseases (Cugno, M.; Salerno, F.: Nussberger, J.; Bottasso, B.; Lorenzano, E.: Agostoni, A. *Clin. Sci.* (*Lond*) 2001, 101, 651-7; WO 01/56995 A1; EP0797997 B1: Wirth, K. J.: Bickel, M.; Hropot, M.: Gunzler, V.; Heitsch, H.; Ruppert, D.; Scholkens, B. A. *Eur. J. Pharmacol.* 1997, 337, 45-53): Within the present application the term "liver and gallbladder diseases" encompasses, but is not limited to, disorders such as hepatitis, cirrhosis of the liver, liver fibrosis (e.g. due to viral (HBV/HCV) infections, toxins (alcohol), fatty liver, bile stasis, hypoxia), portal hypertension, hepatorenal syndrome, hepatogenic edema, cholangitis, cholecystitis, acute and chronic pancreatitis, and biliary colic.

Urinary Tract and Kidney Diseases:

Within the present application the term "Urinary tract and kidney diseases" encompasses, but is not limited to, urinary tract infections such as acute and chronic cystitis, interstitial cystitis (Campbell, D. *J. Clin. Exp. Pharmacol. Physiol.* 2001, 28, 1060-5; Meini, S.; Patacchini, R.; Giuliani, S.; Lazzeri, M.; Turini, D.; Maggi, C. A.; Lecci, A. *Eur. J. Pharmacol.* 2000, 388, 177-82; Zuraw, B. L.; Sugimoto, S.; Parsons, C. L.; Hugh, T.; Lotz, M.; Koziol, J. *J. Urol.* 1994, 152, 874-8; Rosamilia, A.; Clements, J. A.; Dwyer, P. L.; Kende, M.; Campbell, D. J. *J. Urol.* 1999, 162, 129-34), irritable bladder, overactive bladder (WO 2007003411 A2), incontinence including but not limited to stress-, urge and reflex incontinence, benign prostate hyperplasia (Srinivasan, D.; Kosaka, A. H.; Daniels, D. V.; Ford, A. P.; Bhattacharya, A. *Eur J Pharmacol.* 2004, 504(3):155-67), chronic renal disease, urethritis, inflammatory kidney diseases including glomerulonephritis, glomerular disease of the kidney, interstitial nephritis, pyelonephritis, diuresis, proteinuria, natriuresis, calciuresis, disorders of water balance, disorders of electrolyte balance, disorders of acid-base balance and renal colic, renal fibrosis, chronic renal allograft dysfunction, contrast-induced nephropathy.

Diseases of Male Genitale Organs and Female Genitale Organs:

Within the present application the term "diseases of male genitale organs and female genitale organs" encompasses, but is not limited, to altered sperm mobility, male infertility, orchitis, prostatitis, prostate enhancement, mastitis, inflammatory pelvis diseases, vaginal infections and pain, adnexitis, colpitis, soft ulcus, syphilis, clap and ovarian hyperstimulation syndrome (Ujioka, T.; Matsuura, K.; Tanaka, N.; Okamura, H. *Hum Reprod.* 1998 November; 13(11):3009-15.).

Diseases of the Hormone System:

Within the present application the term "diseases of the hormone system" encompasses, but is not limited to, menstrual disorders and pain, climacteric disturbance, emesis, premature uterine contractions, premature labor, endometriosis, endometritis, myoma, pre-eclampsia.

Metabolic Diseases:

Within the present application the term "metabolic diseases" encompasses, but is not limited to, disorders such as diabetes, including non-insulin dependent diabetes mellitus, diabetic retinopathy, diabetic macular edema (Speicher, M. A.; Danis, R. P.; Criswell, M.; Pratt, L. *Expert Opin. Emerg. Drugs* 2003, 8, 239-50; Gao, B. B.; Clermont, A.; Rook, S.; Fonda, S. J.; Srinivasan, V. J.; Wojtkowski, M.; Fujimoto, J. G.; Avery, R. L.; Arrigg, P. G.; Bursell, S. E.; Aiello, L. P.; Feener, E. P. *Nat. Med.* 2007, 13, 181-8; Tranos, P. G.; Wickremasinghe, S. S.; Stangos, N. T.; Topouzis, F.; Tsinopoulos, I.; Pavesio, C. E. *Surv. Ophthalmol* 2004, 49, 470-90), diabetic nephropathy and diabetic neuropathy, insulin resistance and diabetic ulceration, diseases of the proteo- and purine metabolism such as gout and disorder of lipometabolism, hypoglycemia.

Cardiovascular Diseases:

Within the present application the term "cardiovascular diseases" encompasses, but is not limited to, disorders including vascular permeability, vasodilation, peripheral circulatory disorders, arterial circulatory disorders including aortic aneurysm, abdominal aortic aneurysm, brain aortic aneurysm, hypertension and hypotension associated with sepsis, restenosis after percutaneous transluminal coronary angioplasty, atherosclerosis including atherosclerotic plaque rupture (Fernando, A. N.; Fernando, L. P.; Fukuda, Y.; Kaplan, A. P. *Am J Physiol Heart Circ Physiol.* 2005 July; 289(1):H251-7) hemangioma, angiofibroma, venous disorders such as thrombosis, varicosity, phlebitis, thrombophlebitis, phlebothrombosis, cardiopathy, congestive heart failure, coronary heart disease, carcinoid syndrome, angina pectoris, cardiac dysrhythmias, inflammatory heart diseases including endocarditis, pericarditis and constrictive pericarditis, myocarditis, myocardial infarct, postmyocardial infarction syndrome, left ventricular dilation, post ischemic reperfusion injury, shock and collapse including septic, allergic, post traumatic and hemodynamic shock, amniotic fluid embolism (Robillard, J.; Gauvin, F.; Molinaro, G.; Leduc, L.; Adam, A.; Rivard, G. E. *Am J Obstet Gynecol.* 2005 October; 193(4):1508-12.). systemic inflammatory response syndrome (SIRS) including SIRS caused by heart-lung bypass during surgery, sepsis and internal and external complications during cardiopulmonal bypass surgery (including but not limited to adverse hemodynamic effects following protamine sulfate reversal of heparine (Pretorius, M.; Scholl, F. G.; McFarlane, J. A.; Murphey, L. J.; Brown, N. J. *Clin Pharmacol Ther.* 2005 November; 78(5):477-85).

Blood Diseases:

Within the present application the term "blood diseases" encompasses, but is not limited to, disorders such as coagulation, disseminated intravascular coagulopathy, hemorrhage, hemorrhagic diathesis, hypercholesterolemia and hyperlipemia, hypovolemic shock, paroxysmal nocturnal haemoglobinuria.

Lymphatic Diseases:

Within the present application the term "Lymphatic diseases" as used herein encompasses, but is not limited to, splenomegaly, lymphangitis, lymphadenitis and hyperplastic adenoids.

Disorders of the Central Nervous System:

Within the present application the term "disorders of the central nervous system" encompasses, but is not limited to, disorders such as inflammatory diseases of the central nervous system including encephalitis, meningitis, encephalomyelitis, meningoencephalitis, hydrocephalus, amyotrophic lateral sclerosis, spinal cord trauma, spinal cord edema, demyelinating diseases of the nervous system, multiple sclerosis, acute and chronic neuro-degenerative disorders including aging, Alzheimer's disease and Parkinson's disease, neuritis, and peripheral neuropathy, depressions, anorexia, anxiety and schizophrenia, sleep disorders.

Brain Disorders:

Within the present application the term "brain disorders" encompasses, but is not limited to, disorders including nootropic or cognition enhancement, cerebral amyloid angiopathy, stroke, head and brain trauma, traumatic brain injury (Marmarou, A.; Guy, M.; Murphey, L.; Roy, F.; Layani, L.; Combal, J. P.; Marquer, C.; American Brain Injury Consortium *J Neurotrauma* 2005 December; 22(12):1444-55), brain tumor, cerebral heat damage, cerebral ischemia, cerebral hemorrhage, post traumatic and post ischemic cerebral edema, general brain edema, acute mountain sickness and preferably high altitude cerebral edema (HACE), cytotoxic brain edema, vasogenic brain edema, post-surgical brain edema, brain edema associated with metabolic diseases, increase of permeability of blood-brain barrier or blood-brain tumor barrier.

Musculoskeletal System Diseases:

Within the present application the term "musculoskeletal system diseases" encompasses, but is not limited to, disorders such as inflammatory musculoskeletal disorders, arthrosis, osteoarthrosis, osteoarthritis, chondroporosis after joint trauma or relatively long immobilization of a joint after meniscus or patella injuries or torn ligaments, rheumatoid arthritis of whatever type, etiology, or pathogenesis including acute arthritis, acute gouty arthritis, chronic inflammatory arthritis, degenerative arthritis, infectious arthtritis, Lyme arthritis, proliferative arthritis, vertebral arthritis, septic arthritis, psoriatic arthritis, chronic polyarthritis, rheumatism, Sjogren's syndrome, lumbago, spondylitis, spondylarthritis, ankylosing spondylitis, osteomyelitis, sprain, teno-synovitis, inflammation-induced bone resorption, fracture or the like, osteoporosis, musculoskeletal pain and hardening, spinal disk syndrome.

Allergy Disorders:

Within the present application the term "allergy disorders" encompasses, but is not limited to, disorders such as general allergic reactions, food allergy, anaphylactic shock, allergic contact hypersensitivity, allergic skin reactions, allergic asthma, vernal conjunctivitis and seasonal or perennial allergic rhinitis (Summers, C. W.; Pumphrey, R. S.; Woods, C. N.; McDowell, G.; Pemberton, P. W.; Arkwright, P. D. *J Allergy Cin Immunol.* 2008, 121(3), 632-638)

Pain:

Within the present application the term "pain" encompasses, but is not limited to, centrally and peripherally mediated pain, vascular pain, visceral pain, inflammatory mediated pain, neuralgic pain, referred pain, nociceptive pain, reflectory pain, psychosomatic pain, acute pain such as caused by acute injury, trauma or surgery of bones, muscle, tissue, soft tissue, organs, pain after insectbites, post-stroke pain syndrome, post-surgery pain, progressive disease related pain, chronic pain such as caused by neuropathic pain conditions (including but not limited to complex regional pain syndrome (WO00/75107 A2; Yamaguchi-Sase, S.; Hayashi, I.; Okamoto, H.; Nara, Y.; Matsuzaki, S.; Hoka, S.; Majima, M. *Inflamm. Res.* 2003, 52, 164-9; Petersen, M.; Eckert, A. S.; Segond von Banchet, G.; Heppelmann, B.; Klusch, A.; Kniffki, K. D. *Neuroscience* 1998, 83, 949-59; Birklein, F.; Schmelz, M.; Schifter, S.; Weber, M. *Neurology* 2001, 57, 2179-84; Weber, M.; Birklein, F.; Neundorfer, B.; Schmelz, M. *Pain* 2001, 91, 251-7), causalgia, morbus sudeck, reflex sympathetic dystrophy), diabetic peripheral neuropathy, post-herpetic neuralgia, trigeminal neuralgia, cancer-related pain, pain associated with rheumatoid arthritis, osteoarthritis (Bond, A. P.; Lemon, M.; Dieppe, P. A.; Bhoola, K. D. *Immunopharmacology* 1997, 36, 209-16; Cassim, B.; Naidoo, S.; Ramsaroop, R.; Bhoola, K. D. *Immunopharmacology* 1997, 36, 121-5; Calixto, J. B.; Cabrini, D. A.; Ferreira, J.; Campos, M. M. *Pain* 2000, 87, 1-5; Kaneyama, K.; Segami, N.; Sato, J.; Fujimura, K.; Nagao, T.; Yoshimura, H. *J. Oral. Maxillofac. Surg.* 2007, 65, 242-7), teno-synovitis, gout, menstruation and angina, fibromyalgia, ocular pain, back pain, headache, cluster headache, migraine (Ebersberger, A.; Ringkamp, M.; Reeh, P. W.; Handwerker, H. O. *J Neurophysiol.* 1997 June; 77(6):3122-33.), inflammatory pain, which may be associated with acute inflammation or chronic inflammation. Inflammatory pain includes but is not limited to neuropathic pain, ischemic pain, pain induced by arthritis, muscle pain induced by acute or chronic inflammation, neuralgia caused by acute or chronic inflammation, hyperalgesia. Also chemotherapy-induced peripheral neuropathy, hyperalgesia, opioid-induced hyperalgesia and fever. Furthermore, compounds of the invention are useful as analgesic agent for use during general and monitored anesthesia.

Infectious Diseases:

Within the present application the term "infectious diseases" encompasses, but is not limited to, diseases including those mediated by bacteria, viruses, fungi, parasites, protozoa, prions or mycobacterial infections. Particularly, the present invention is useful for the treatment of bacterial infections caused by *Streptococcus, Escherichia, Salmonella, Staphylococcus, Klebsiella, Moracella, Haemophilus* and *Yersinia*. Examples of bacterial infections intended to be within the scope of the present invention include, but are not limited to diseases such as *pestis*, sepsis, epidemic typhus, food poisoning, tetanus, scarlet red, whooping cough, diphtheria. Examples of viral infections intended to be within the scope of the present invention include, but are not limited to diseases such chickenpox and herpes zoster, AIDS, influenza, small pox, and children diseases such as measles, rubella, mumps, acute anterior poliomyelitis. The present invention is useful for the treatment of protozoa and parasites infections caused by *Schistosoma mansoni*, Dermatofagoidesfarinae and *Plasmodium* inducing Malaria. Examples of prion infections intended to be within the scope of the present invention include, but are not limited to diseases such bovine spongiform encephalopathy (BSE), Creutzfeldt Jacob disease and kuru, dengue fever, hemorrhagic fever.

Inflammatory Disorders:

Within the present application the term "inflammatory disorders" encompasses, but is not limited to, disorders such as acute-phase reaction, local and systemic inflammation and inflammation caused by other diseases whatever type, etiology or pathogenesis and caused by those inflammatory diseases specified within this application.

Injuries:

Within the present application the term "injuries" encompasses, but is not limited to, multiple trauma, head trauma, lung injuries, external, internal and surgery wounds.

Immunology Disorders:

Within the present application the term "immunology disorders" encompasses, but is not limited to, disorders such as hyperesthesia, autoimmune disorders, graft rejection in transplantation, transplant toxicity, granulomatous inflammation/tissue remodelling, myasthenia gravis, immunosuppression, immune-complex diseases, over- and underproduction of antibodies, vasculitis, delayed graft function, lupus.

Cancers:

Within the present application the term "cancers" encompasses, but is not limited to, disorders such as solid tumor cancer including breast cancer, lung cancer (non-small-cell lung cancer and small-cell lung cancer), prostate cancer, cancers of the oral cavity and pharynx (lip, tongue, mouth, pharynx), esophagus, stomach, small intestine, large intestine, colon, rectum, gallbladder and biliary passages, pancreas, larynx, lung, bone, osteosarcoma, connective tissue, skin cancer including Kaposi's syndrome, melanoma and skin metastasis, epidermoid cancer, basal cell carcinoma, cervix uteri, corpus endometrium, cancer of ovary, testis, bladder, ureter and urethra, kidney, eye, brain and central nervous system, pseudotumor cerebri, sarcoma, sarcoid, thyroid and other endocrine glands (including but not limited to carcinoid tumors), Hodgkin's disease, non-Hodkin's lymphomas, multiple myeloma, hematopoetic malignancies including leukemias and lymphomas including lymphocytic, granulocytic and monocytic lymphomas, tumor invasion, metastasis, ascites, tumor growth and angiogenesis.

Hereditary Diseases:

Within the present application the term "hereditary diseases" encompasses, but is not limited to, disorders such as hereditary angioedema (Davis, A. E. et al., 3rd *Transfus. Apher. Sci.* 2003, 29, 195-203; Zuraw, B. L. *Immunol. Allergy Clin. North Am.* 2006, 26, 691-708; Bas, M. et al. *Allergy* 2006, 61, 1490-2) and angioneurotic edema, chondrocalcinosis, Huntington's disease, mucoviscidosis.

Edema:

Within the present application the term "edema" encompasses, but is not limited to, general edema and edema caused by inflammation, Factor XII deficiency-induced edema, other drugs, e.g. drug induced angioedema, including but not limited to angiotensin-converting enzyme inhibitor-induced angioedema (Mathelier-Fusade, P. *Clin. Rev. Allergy Immunol.* 2006, 30, 19-23; Finley, C. J. et al. *Am. J. Emerg. Med.* 1992, 10, 550-2; Bielory, L. et al. *Allergy Proc.* 1992, 13, 85-7), infection, burns, injuries, trauma, frostbite, surgery, distorsions, fractures, exposure to high altitude (e.g. high altitude pulmonary edema (HAPE) and high altitude cerebral edema (HACE)), hereditary, autoimmune and other diseases and disorders, particularly but not limited to those disorders specified in this application, stress-induced edema (pronounced swelling) of gut.

Capillary Leak Syndrome(s):

Within the present application the term "capillary leak syndrome(s)" encompasses, but is not limited to, systemic capillary leak syndrome in sepsis (Marx, G. *Eur J Anaesthesiol.* 2003 20(6):429-42; Traber, D. L. *Crit Care Med.* 2000, 28(3):882-3), burn (Jonkam, C. C.; Enkhbaatar, P.; Nakano, Y.; Boehm, T.; Wang, J.; Nussberger, J. Esechie, A.; Traber, L. D.; Herndon, D.; Traber, D. L. *Shock.* 2007 December; 28(6):704-9), allergy, drug/toxin-induced conditions, organ transplantation and IL-2 cytokine therapy.

The compound according to the present invention can also be used as or for the manufacture of a diagnostic agent. Such a diagnostic agent is particularly useful in the diagnosis of the diseases and conditions disclosed herein, which can be addressed by the compound of the present invention for therapeutic and or prophylactic purposes. The compound according to the present invention has also utility in specific methodology and diagnostics as disclosed herein below.

Methodology and Diagnostics:

Compounds of the invention can be labelled by isotopes, fluorescence or luminescence markers, antibodies or antibody fragments, any other affinity label like nanobodies, aptamers, peptides etc., enzymes or enzyme substrates. These labelled compounds of this invention are useful for mapping the location of bradykinin receptors in vivo, ex vivo, in vitro and in situ (e.g. in tissue sections via autoradiography) and as radiotracers for positron emission tomography (PET) imaging, single photon emission computerized tomography (SPECT) and the like to characterize those receptors in living subjects or other materials.

The present invention also pertains to methods for altering the signal-transducing activity of bradykinin receptors in vitro and in vivo. For instance, compounds of the present invention and labelled derivatives thereof can be used as standard and reagent in determining the ability of a potential pharmaceutical to bind to the BK B2 receptor.

The present invention also provides methods for localizing or detecting a BK B2 receptor in a tissue, preferably a tissue section, which methods involve contacting the tissue sample containing BK B2 receptor with a detectably labelled compound according to the present invention under conditions that permit binding of the compound to the BK B2 receptor and detecting the bound compound. Such methods and their respective conditions are known to those skilled in the art and include, for example, the binding assay disclosed in Example 12.

The present invention further provides a method for treating a patient suffering from a condition or disease responsive to BK B2 receptor modulation as mentioned above. The method for the treatment of a subject which is in need of such treatment comprises the administration of a compound according to the invention, e.g. according to any of [1] to [24], a pharmaceutically acceptable salt thereof, a pharmaceutical composition as disclosed herein, or a combination preparation as disclosed herein. As used herein, the term "treatment" encompasses both disease-modifying treatment and symptomatic treatment, either of which may be prophylactic (i.e., before the onset of symptoms, in order to prevent, delay or reduce the severity of symptoms) or therapeutic (i.e., after the onset of symptoms, in order to reduce the severity and/or duration of symptoms). A condition is "responsive to BK B2 receptor modulation" if modulation of BK B2 receptor activity results in alleviation of the condition or a symptom thereof. Patients may include but are not limited to primates (especially humans), domesticated companion animals (such as dogs, cats, horses) and livestock (such as cattle, pigs, sheep), with dosages as described herein.

The compounds of general formula (I) according to the present invention have improved properties when compared to BK B2 receptor antagonists known in the state of the art, especially, one or more improved pharmacokinetic and/or physiochemical properties, including, for example, bioavailability, metabolic stability, improved activity/selectivity, low toxicity, and low drug drug interaction. Accordingly, the compound (or pharmaceutically acceptable salt thereof), the pharmaceutical composition, or the combination preparation disclosed herein can be used as medicament. For instance, the compound (or pharmaceutically acceptable salt thereof), the pharmaceutical composition, or the combination preparation disclosed herein can be used in the treatment and/or prevention of a condition responsive to BK B2 receptor modulation, including, for example, the conditions listed above.

The present invention is now further illustrated by the following examples from which further features, embodiments and advantages of the present invention may be taken. However, the invention should not be construed to be limited to the examples, but encompasses the subject-matter defined in the claims.

EXAMPLES

Abbreviations used in the following examples are as follows:
ACN is acetonitrile
BuLi is n-butyllithium
conc. is concentrated
DCM is dichloromethane
DIPEA is ethyl-diisopropyl-amine
DMF is dimethylformamide
EA is ethyl acetate
HPLC is high performance liquid chromatography
MeOH is methanol
NBS is N-bromosuccinimide
NMP is N-methylpyrrolidone
PyAOP is 7-azabenzotriazol-1-yloxy)tripyrrolidinophosphonium hexafluorophosphate
PyBOP is (benzotriazol-1-yloxy)tripyrrolidinophosphonium hexafluorophosphate
RT is room temperature
THF is tetrahydrofurane
TLC is thin layer chromatography
TFA is trifluoroacetic acid
sat. is saturated Specific examples for the preparation of compounds of formula (I) are provided in the following examples. Unless otherwise specified all starting materials and reagents are of standard commercial grade, and are used without further purification, or are readily prepared from such materials by routine methods. Those skilled in the art of organic synthesis will recognize that starting materials and reaction conditions may be varied including additional steps employed to produce compounds encompassed by the present invention.

Example 1: Preparation of Compound No. 1

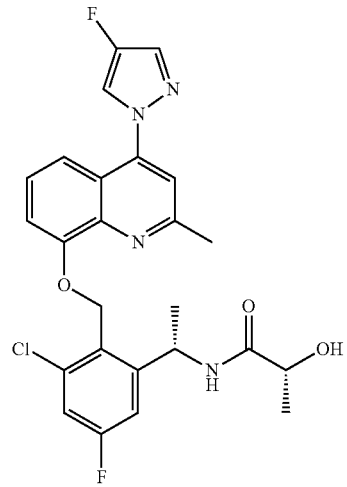 [SMILES: Cc1cc(-n2cc(F)cn2)c2cccc(OCc3c(Cl)cc(F)cc3[C@H](C)NC(=O)[C@@H](C)O)c2n1]

(R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide Step A. Synthesis of methyl 3-amino-5-fluoro-2-methylbenzoate Methyl 5-fluoro-2-methyl-3-nitrobenzoate [Gillmore, A. T. et al. *Org. Process Res. Dev.* 2012, 16, 1897-1904] (4.69 g, 22 mmol) was dissolved in MeOH (100 mL) and palladium on activated charcoal—10% Pd (200 mg) was added. The solution was flushed and evacuated three times with nitrogen before it was flushed with hydrogen. The reaction mixture was vigorously stirred under 1 atm of hydrogen. After completion of the reaction as indicated by TLC (21 h) the solution was filtered over silica gel. The filter cake was washed with methanol (5×20 mL). The filtrate was concentrated under reduced pressure and the residue was purified by flash chromatography to yield the title compound. MS (m/z): 184.0 [M+H$^+$].

Step B. Synthesis of methyl 3-chloro-5-fluoro-2-methylbenzoate

NaNO$_2$ (1.68 g, 24.4 mmol) was added to a solution of methyl 3-amino-5-fluoro-2-methylbenzoate (4.00 g, 18.8 mmol) in half-concentrated aqueous HCl (400 mL) at 0° C. After stirring for 5 min at 0° C., CuCl (3.72 g, 37.5 mmol) was added to the reaction mixture. After stirring for 2 h at 0° C., the reaction mixture was extracted with DCM (2×100 mL). The combined organic layers were washed with concentrated aqueous $NaHCO_3$-solution (1×), dried over $Na_2SO_4$, filtered, and concentrated in vacuo. The residue was purified by flash chromatography on silica gel (elution with DCM/heptane) to give the title compound.

Step C. Synthesis of methyl 2-(bromomethyl)-3-chloro-5-fluorobenzoate

Benzoyl peroxide (26 mg, 0.11 mmol) and N-bromosuccinimide (210 mg, 1.18 mmol) were added to a stirred solution of methyl 3-chloro-5-fluoro-2-methylbenzoate (200 mg, 0.99 mmol) in benzene (7.0 mL). After stirring at reflux for 1.5 h, the reaction mixture was diluted with EA (20 mL) and washed with 10% aqueous $Na_2S_2O_3$ (1×5 mL) solution. The organic layer was dried over $Na_2SO_4$, filtered, and concentrated in vacuo to give the title compound.

Step D. Synthesis of methyl 3-chloro-5-fluoro-2-((4-methoxyphenoxy)methyl)benzoate $Cs_2CO_3$ (617 mg, 3.20 mmol) was added to a stirred solution of 2-(bromomethyl)-3-chloro-5-fluorobenzoate (300 mg, 1.07 mmol) and 4-methoxyphenol (172 mg, 1.39 mmol) in ACN (7.0 mL). After stirring overnight at RT, the reaction mixture was filtered and concentrated in vacuo. The residue was purified by flash chromatography on silica gel (elution with EA/heptane) to give the title compound. MS (m/z): 342.1 [M+$NH_4$].

Step E. Synthesis of 3-chloro-5-fluoro-2-((4-methoxyphenoxy)methyl)benzoic acid A solution of LiOH (2.37 g, 57 mmol) in water (50 mL) was added to a stirred solution of methyl 3-chloro-5-fluoro-2-((4-methoxyphenoxy)methyl)benzoate (9.16 g, 28 mmol) in dioxane (100 mL) at 0° C. After stirring for 2 h at RT the reaction mixture was concentrated in vacuo and the pH value adjusted to 1-2 by the addition of conc. aqueous HCl. The mixture was extracted with DCM (3×100 mL)), the combined organic layers were dried over $Na_2SO_4$, filtered, and concentrated in vacuo to give the title compound.

Step F. Synthesis of 1-(3-chloro-5-fluoro-2-((4-methoxyphenoxy)methyl)phenyl)ethanone A solution of methyllithium (1.6 M, 30.2 mL) in diethylether was added dropwise to a solution of 3-chloro-5-fluoro-2-((4-methoxyphenoxy)methyl)benzoic acid (5.00 g, 16 mmol) in anhydrous diethylether (110 mL) at 0° C. After stirring for 30 min at 0° C., the reaction was quenched by the addition of sat. aqueous $NH_4Cl$ (15 mL) at 0° C. The reaction mixture was diluted with water (15 mL), the organic layer was separated and the aqueous layer extracted with diethylether (3×50 mL). The combined organic layers were dried over $Na_2SO_4$, filtered, and concentrated in vacuo. The residue was purified by flash chromatography on silica gel (elution with EA/heptane) to give the title compound.

Step G. Synthesis of (R)—N—((S)-1-(3-chloro-5-fluoro-2-((4-methoxyphenoxy)methyl)phenyl)ethyl)-2-methylpropane-2-sulfinamide Titan(IV)ethoxide (2.53 mL, 12.05 mmol) was added dropwise under an Argon atmosphere to a solution of 1-(3-chloro-5-fluoro-2-((4-methoxyphenoxy)methyl)phenyl)ethanone (1.24 g, 4.02 mmol) and (R)-(+)-2-methyl-2-propanesulfinamide (535.5 mg, 4.42 mmol) in anhydrous THF (10 mL). The mixture was heated under reflux until complete conversion (TLC). Subsequently, the mixture was cooled to 0° C. and L-Selectride (1 M solution, 12.05 mL, 12.05 mmol) was added dropwise. The mixture was stirred at this temperature until complete conversion (TLC). Subsequently, methanol (~10 mL) was added until evolution of gas stopped. The solution was poured into sat. aqueous NaCl solution (30 mL). Then, the mixture was filtrated over a pad of Celite and carefully rinsed with DCM. The filtrate was washed with sat. aqueous NaCl solution. The aqueous layer was extracted with DCM. The combined organic layers were dried over $Na_2SO_4$, filtrated, and evaporated to dryness. The remaining residue was purified by flash chromatography on silica gel (elution with EA/heptane) to give the title compound. MS (m/z): 458.2 [M+$HCO_2^-$].

Step H. Synthesis of (S)-1-(3-chloro-5-fluoro-2-((4-methoxyphenoxy)methyl)phenyl)ethanamine A solution of (R)—N—((S)-1-(3-chloro-5-fluoro-2-((4-methoxyphenoxy)methyl)phenyl)ethyl)-2-methylpropane-2-sulfinamide (2.19 g, 5.29 mmol) in 3 M methanolic HCl (3.53 mL, 10.6 mmol) was stirred at room temperature until complete conversion (TLC). The solution was concentrated in vacuo. The remaining residue was dissolved in DCM (5 mL) and washed with sat. aqueous $NaHCO_3$ solution (6 mL) and water (6 mL). The organic layer was dried over $Na_2SO_4$, filtered and concentrated in vacuo to give the title compound. MS (m/z): 354.4 [M+$HCO_2^-$].

Step I. Synthesis of (S)-2-(1-(3-chloro-5-fluoro-2-((4-methoxyphenoxy)methyl)phenyl)ethyl)isoindoline-1,3-dione Phthalic anhydride (862 mg, 5.82 mmol) was added to a solution of (S)-1-(3-chloro-5-fluoro-2-((4-methoxyphenoxy)methyl)phenyl)ethanamine (1.64 g, 5.26 mmol) in DCM (20 mL). The mixture was stirred for 15 min and then concentrated in vacuo. The remaining residue was heated in about 10 min to 175° C. in an open vessel. After 45 min at this temperature the reaction mixture was cooled to room temperature and purified by flash chromatography on silica gel (elution with heptane/EA) to give the title compound. MS (m/z): 484.3 [M+$HCO_2^-$].

Step J. Synthesis of (S)-2-(1-(3-chloro-5-fluoro-2-(hydroxymethyl)phenyl)ethyl)isoindoline-1,3-dione A solution of ammonium cerium(IV) nitrate (3.36 g, 6.12 mmol) in $H_2O$ (4 mL) was added to a stirred solution (S)-2-(1-(3-chloro-5-fluoro-2-((4-methoxyphenoxy)methyl)phenyl)ethyl)isoindoline-1,3-dione (1.07 g, 2.45 mmol) in ACN (20 mL) at 0° C. After stirring for 5 h at 0° C., the reaction was quenched by the addition of brine (20 mL) and $H_2O$ (5 mL). The mixture was extracted with EA (3×100 mL), the combined organic layers were dried over $Na_2SO_4$, filtered, and concentrated in vacuo. The residue was purified by flash chromatography on silica gel (elution with EA/heptane) to give the title compound.

Step K. Synthesis of (S)-2-(1-(3-chloro-2-(chloromethyl)-5-fluorophenyl)ethyl)isoindoline-1,3-dione $SOCl_2$ (288 µL, 3.96 mmol) and water (4 µL) were added to a stirred solution of (S)-2-(1-(3-chloro-5-fluoro-2-(hydroxymethyl)phenyl)ethyl)isoindoline-1,3-dione (662 mg, 1.98 mmol) in DCM (10 mL) at RT. The solution was stirred until complete conversion (TLC). Then, the solvent was removed in vacuo and the residue was purified by flash chromatography on silica gel (elution with EA/heptane) to give the title compound. MS (m/z): 396.1 [M+HCO$_2^-$].

Step L. Synthesis of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione Cs$_2$CO$_3$ (1.94 g, 5.95 mmol) was added to a stirred solution of (S)-2-(1-(3-chloro-2-(chloromethyl)-5-fluorophenyl)ethyl)isoindoline-1,3-dione (698 mg, 1.98 mmol) and 4-(4-fluoro-1H-pyrazol-1-yl)-2-methylquinolin-8-ol (482 mg, 1.98 mmol) in ACN (20 mL). After stirring overnight at RT, the reaction mixture was filtered and concentrated in vacuo. The residue was purified by flash chromatography on silica gel (elution with EA/heptane) to give the title compound. MS (m/z): 559.3 [M+H$^+$].

Step M. Synthesis of (S)-1-(3-chloro-5-fluoro-2-((4-(4-fluoro-1H-pyrazol-1-yl)-2-methylquinolin-8-yloxy)methyl)phenyl)ethanamine Hydrazine hydrate (371 µL) was added to a solution of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione (1.07 g, 1.91 mmol) in EtOH (30 mL). After stirring for 2 h at 85° C., the reaction mixture was cooled to RT and filtered. The filtrate was concentrated in vacuo and the residue was purified by flash chromatography (elution with DCM/MeOH/conc. aqueous NH$_3$) to yield the title compound. MS (m/z): 429.4 [M+H$^+$].

Step N. Synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide PyAOP (90.7 mg, 174 µmol) and DIPEA (29.4 mg, 227 µmol) were subsequently added to a stirred solution of (S)-1-(3-chloro-5-fluoro-2-((4-(4-fluoro-1H-pyrazol-1-yl)-2-methylquinolin-8-yloxy)methyl)phenyl)ethanamine (55.1 mg, 137 µmol) and (R)-2-hydroxypropanoic acid (13.9 mg, 154 µmol) in DMF (4.5 mL) at 0° C. After stirring for 2 h at RT, the reaction mixture was concentrated in vacuo. Purification of the remaining residue by reverse phase HPLC afforded the title compound. MS (m/z): 501.2 [M+H$^+$].

Step O. Synthesis 4-(4-fluoro-1H-pyrazol-1-yl)-8-methoxy-2-methylquinoline

K$_2$CO$_3$ (4.99 g, 36.1 mmol) was added to a stirred mixture of 4-chloro-8-methoxy-2-methylquinoline (5.00 g, 24.0 mmol) and 4-fluoro-1H-pyrazole (3.85 g, 28.8 mmol) in anhydrous NMP (12 mL). After stirring for 48 h at 140° C. the reaction mixture was cooled to RT and filtered.

The residue was rinsed with DMF (13 mL). Then water (90 mL) was then added to the combined filtrates. The precipitate was filtered off and purified by flash chromatography on silica gel (elution with DCM/methanol) to give the title compound. MS (m/z): 258.0 [M+H$^+$].

Step P. Synthesis of 4-(4-fluoro-1H-pyrazol-1-yl)-2-methylquinolin-8-ol

A solution of 4-(4-fluoro-1H-pyrazol-1-yl)-8-methoxy-2-methylquinoline (5.51 g, 21.4 mmol) in anhydrous toluene (37.8 mL) was warmed to 80° C. and added dropwise to a vigorously stirred mixture of AlCl$_3$ (8.58 g, 64.3 mmol) in anhydrous toluene (32.4 mL). After stirring for 8 h at 80° C. the reaction mixture was cooled to 0° C. and quenched by the addition of water (106 mL) and conc. aqueous NH$_3$ (27 mL). After stirring overnight at RT, the mixture was centrifuged. The supernatant was extracted with EA (3×200 mL) and the combined organic layers were dried over Na$_2$SO$_4$, filtered, and concentrated in vacuo. The residue was purified by flash chromatography on silica gel (elution with DCM/methanol) to give the title compound.

Example 2: Preparation of Compound No. 2

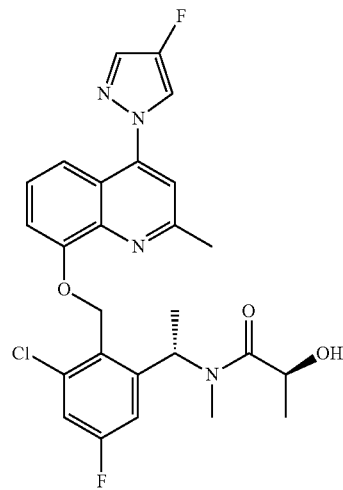 [SMILES: Cc1cc(-n2cc(F)cn2)c2cccc(OCc3c(Cl)cc(F)cc3[C@H](C)N(C)C(=O)[C@H](C)O)c2n1]

(S)—N—((S)-1-(3-chloro-5-fluoro-2-((4-(4-fluoro-1H-pyrazol-1-yl)-2-methylquinolin-8-yloxy)methyl)phenyl)ethyl)-2-hydroxy-N-methylpropanamide

Step A. Synthesis of (2S)—N—((S)-1-(3-chloro-5-fluoro-2-((4-methoxyphenoxy)methyl)phenyl)ethyl)-2-(tetrahydro-2H-pyran-2-yloxy)propanamide (S)-1-(3-chloro-5-fluoro-2-((4-methoxyphenoxy)methyl)phenyl)ethanamine (100 mg, 323 µmol) was reacted with (2S)-2-(tetrahydro-2H-pyran-2-yloxy)propanoic acid [Garner P. et al. *J. Org. Chem.* (2002), 67(17), 6195-6209] (84.3 mg, 484 µmol) according to the synthesis of N-(1-(3-chloro-5-fluoro-2-((4-(4-fluoro-1H-pyrazol-1-yl)-2-methylquinolin-8-yloxy)methyl)phenyl)ethyl)-3-hydroxy-2-methylpropanamide. The crude product was purified by flash chromatography on silica gel (elution with EA/heptane) to give the title compound. MS (m/z): 488.5 [M+Na].

Step B. Synthesis of (2S)—N—((S)-1-(3-chloro-5-fluoro-2-((4-methoxyphenoxy)methyl)phenyl)ethyl)-N-methyl-2-(tetrahydro-2H-pyran-2-yloxy)propanamide (2S)—N—((S)-1-(3-chloro-5-fluoro-2-((4-methoxyphenoxy)methyl)phenyl)ethyl)-2-(tetrahydro-2H-pyran-2-yloxy)propanamide (50 mg, 107 µmol) was dissolved in anhydrous DMF (ca. 5 ml/mmol). Under an argon atmosphere sodium hydride [60% in paraffin] (4.7 mg, 118 µmol) was added and the mixture was stirred for 20 min. Then, iodomethane (33.3 µl, 535 µmol) was added and stirring was continued until full conversion (TLC). Water was added and extraction with EA was performed several times. The combined organic layers were dried over Na$_2$SO$_4$, filtered and evaporated to dryness under reduced pressure. The crude product was purified by flash chromatography on silica gel (elution with EA/heptane) to give the title compound. MS (m/z): 502.3 [M+Na].

Step C. Synthesis of (S)—N—((S)-1-(3-chloro-5-fluoro-2-(hydroxymethyl)phenyl)ethyl)-2-hydroxy-N-methylpropanamide (2S)—N—((S)-1-(3-chloro-5-fluoro-2-((4-methoxyphenoxy)methyl)phenyl)ethyl)-N-methyl-2-(tetrahydro-2H-pyran-2-yloxy)propanamide (41.0 mg, 85 µmol) was reacted with ammonium cerium(IV) nitrate (117.1 mg, 214 µmol) according to the synthesis of (S)-2-(1-(3-chloro-5-fluoro-2-(hydroxymethyl)phenyl)ethyl)isoindoline-1,3-dione. The crude product was dissolved in methanol, 3 M methanolic HCl-solution was added and stirring at RT was continued until complete reaction (TLC). Evaporation under reduced pressure gave the title compound. MS (m/z): 312.4 [M+Na].

Step D. Synthesis of (S)—N—((S)-1-(3-chloro-2-(chloromethyl)-5-fluorophenyl)ethyl)-2-hydroxy-N-methylpropanamide (S)—N—((S)-1-(3-chloro-5-fluoro-2-(hydroxymethyl)phenyl)ethyl)-2-hydroxy-N-methylpropanamide (13.70 mg, 47 µmol) was reacted with SOCl$_2$ (6.82 µl, 11.18 mg, 156 µmol) according to the synthesis of (S)-2-(1-(3-chloro-2-(chloromethyl)-5-fluorophenyl)ethyl)isoindoline-1,3-dione to give the title compound. MS (m/z): 330.4 [M+Na].

Step E. Synthesis of (S)—N—((S)-1-(3-chloro-5-fluoro-2-((4-(4-fluoro-1H-pyrazol-1-yl)-2-methylquinolin-8-yloxy)methyl)phenyl)ethyl)-2-hydroxy-N-methylpropanamide (S)—N—((S)-1-(3-chloro-2-(chloromethyl)-5-fluorophenyl)ethyl)-2-hydroxy-N-methylpropanamide (14.6 mg, 47 µmol) was reacted with 4-(4-fluoro-1H-pyrazol-1-yl)-2-methylquinolin-8-ol (12 mg, 47 µmol) according to the synthesis of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione to give the title compound. MS (m/z): 515.5 [M+H$^+$].

Example 3: Preparation of Compound No. 3

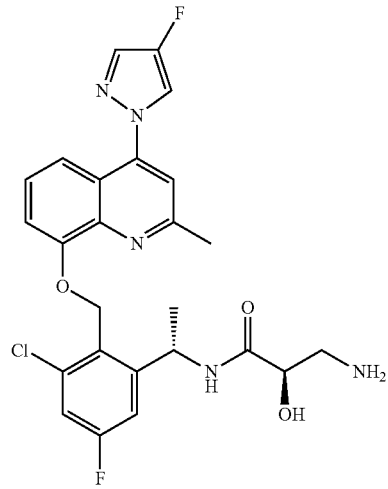 [SMILES: Cc1cc(-n2cc(F)cn2)c2cccc(OCc3c(Cl)cc(F)cc3[C@H](C)NC(=O)[C@H](O)CN)c2n1]

(R)-3-amino-N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide Step A. Synthesis of (R)-3-(tert-butoxycarbonylamino)-2-hydroxypropanoic acid K$_2$CO$_3$ (107. mg, 0.78 mmol) and NaHCO$_3$ (107 mg, 1.27 mmol) were added to a mixtures of (R)-3-amino-2-hydroxypropanoic acid (668 mg, 6.36 mmol) in dioxane and water (3:1, v/v, 10 mL). Di-tert-butyl dicarbonate (998 mg, 6.99 mmol) was added and stirring was continued over night at RT. Then, the mixture was acidified to pH 2 using 1 M HCl. Subsequently, the mixture was extracted several times with EA. The combined organic layers were dried with Na$_2$SO$_4$, filtrated, and concentrated in vacuo to give the title compound. MS (m/z): 206.2 [M+H$^+$].

Step B. Synthesis of tert-butyl (R)-3-((S)-1-(3-chloro-5-fluoro-2-((4-(4-fluoro-1H-pyrazol-1-yl)-2-methylquinolin-8-yloxy)methyl)phenyl)ethylamino)-2-hydroxy-3-oxopropylcarbamate (S)-1-(3-chloro-5-fluoro-2-((4-(4-fluoro-1H-pyrazol-1-yl)-2-methylquinolin-8-yloxy)methyl)phenyl)ethanamine (25 mg, 0.06 mmol) was reacted with (R)-3-(tert-butoxycarbonylamino)-2-hydroxypropanoic acid (18.0 mg, 0.09 mmol) according to the synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide to give the title compound. The crude product was used without further purification.

Step C. Synthesis of (R)-3-amino-N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide Crude tert-butyl (R)-3-((S)-1-(3-chloro-5-fluoro-2-((4-(4-fluoro-1H-pyrazol-1-yl)-2-methylquinolin-8-yloxy)methyl)phenyl)ethylamino)-2-hydroxy-3-oxopropylcarbamate was dissolved in DCM (1.5 mL) and TFA (200 µL) was added.

The mixture was stirred for 1 h. Then, the mixture was diluted with toluene (1.5 mL) and concentrated in vacuo. Purification of the residue by reverse phase HPLC afforded the title compound. MS (m/z): 516.5 [M+H⁺].

Example 4: Preparation of Compound No. 4

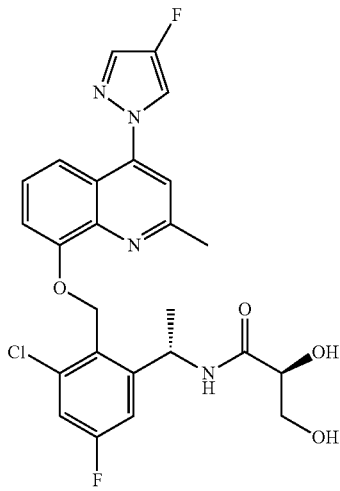 [SMILES: Cc1cc(-n2cc(F)cn2)c2cccc(OCc3c(Cl)cc(F)cc3[C@H](C)NC(=O)[C@@H](O)CO)c2n1]

(S)—N—((S)-1-(3-chloro-5-fluoro-2-((4-(4-fluoro-1H-pyrazol-1-yl)-2-methylquinolin-8-yloxy)methyl)phenyl)ethyl)-2,3-dihydroxypropanamide Step A. Synthesis of (S)—N—((S)-1-(3-chloro-5-fluoro-2-((4-(4-fluoro-1H-pyrazol-1-yl)-2-methylquinolin-8-yloxy)methyl)phenyl)ethyl)-2,2-dimethyl-1,3-dioxolane-4-carboxamide (S)-1-(3-chloro-5-fluoro-2-((4-(4-fluoro-1H-pyrazol-1-yl)-2-methylquinolin-8-yloxy)methyl)phenyl)ethanamine (25.0 mg, 0.06 mmol) was reacted with (S)-2,2-dimethyl-1,3-dioxolane-4-carboxylic acid (12.8 mg, 0.09 mmol) according to the synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide to give the crude title compound. The crude product was used without further purification.

Step B. Synthesis of (S)—N—((S)-1-(3-chloro-5-fluoro-2-((4-(4-fluoro-1H-pyrazol-1-yl)-2-methylquinolin-8-yloxy)methyl)phenyl)ethyl)-2,3-dihydroxypropanamide Crude (S)—N—((S)-1-(3-chloro-5-fluoro-2-((4-(4-fluoro-1H-pyrazol-1-yl)-2-methylquinolin-8-yloxy)methyl)phenyl)ethyl)-2,2-dimethyl-1,3-dioxolane-4-carboxamide was dissolved in MeOH (1.0 mL) and concentrated HCl (5 drops) was added. The mixture was stirred for 20 h. Then, the mixture was concentrated in vacuo. Purification of the residue by reverse phase HPLC afforded the title compound. MS (m/z): 517.1 [M+H⁺].

Example 5: Preparation of Compound No. 5

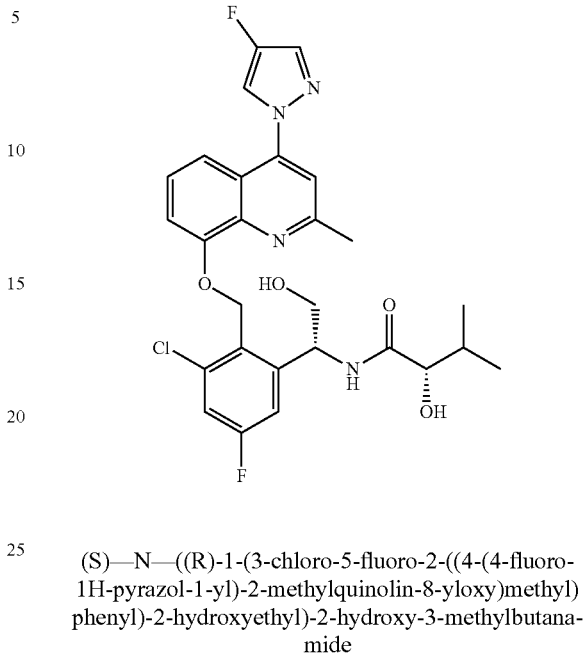

(S)—N—((R)-1-(3-chloro-5-fluoro-2-((4-(4-fluoro-1H-pyrazol-1-yl)-2-methylquinolin-8-yloxy)methyl)phenyl)-2-hydroxyethyl)-2-hydroxy-3-methylbutanamide Step A. Synthesis of 3-bromo-5-fluoro-2-methylaniline 1-Bromo-5-fluoro-2-methyl-3-nitrobenzene (3.04 mL, 22.0 mmol) was dissolved in a 4:1 mixture of dioxan and water (110 mL). The solution was cooled to 0° C. and Zn dust (14.4 g, 220 mmol) and NH₄Cl (11.8 g, 220 mmol) were added. The reaction mixture was stirred at RT for 3 h. After complete conversion, the mixture was filtered over a pad of Celite. It was carefully rinsed with EA and the filtrate was washed with water. The organic phase was dried over Na₂SO₄, filtered and concentrated in vacuo to give the title compound.

Step B. Synthesis of 1-bromo-3-chloro-5-fluoro-2-methylbenzene

NaNO₂ (1.93 g, 28.0 mmol) was added to a solution of 3-bromo-5-fluoro-2-methylaniline (4.40 g, 21.6 mmol) in acetic acid (100 mL) and half-concentrated aqueous HCl (400 mL) at 0° C. After stirring for 5 min at 0° C., CuCl (3.72 g, 37.5 mmol) was added to the reaction mixture. After stirring for 2 h at 0° C., the reaction mixture was warmed to RT and stirring was continued for additional 3 h. Subsequently, the mixture was extracted with Et₂O. The combined organic layers were washed with concentrated aqueous NaHCO₃-solution (1×), dried over Na₂SO₄, filtered, and concentrated in vacuo (bath temperature max. 30° C., vacuum >150 mbar) to give the title compound.

Step C. Synthesis of 1-bromo-2-(bromomethyl)-3-chloro-5-fluorobenzene

NBS (4.61 g, 25.9 mmol) and AIBN (531 mg, 3.23 mmol) were added to a stirred solution of 1-bromo-3-chloro-5-fluoro-2-methylbenzene (5.43 g, 21.6 mmol) in ACN (150 mL). After stirring for 8 h at reflux the mixture was concentrated in vacuo. The residue was purified by flash chromatography on silica gel (elution with heptane/EA) to give the title compound.

Step D. Synthesis of 1-bromo-3-chloro-5-fluoro-2-((4-methoxyphenoxy)methyl)benzene $Cs_2CO_3$ (14.5 g, 44.5 mmol) was added to a stirred solution of 1-bromo-2-(bromomethyl)-3-chloro-5-fluorobenzene (4.48 g, 14.8 mmol) and 4-methoxyphenol (2.39 g, 19.3 mmol) in ACN (250 mL). After stirring overnight at RT, the reaction mixture was filtered and concentrated in vacuo. The residue was dissolved in DCM and washed with water (1×). The organic phase was dried over $Na_2SO_4$, filtered and concentrated in vacuo. The crude product was purified by flash chromatography on silica gel (elution with EA/heptane) to give the title compound.

Step E. Synthesis of (R)—N—((R)-2-(tert-butyldimethylsilyloxy)-1-(3-chloro-5-fluoro-2-((4-methoxyphenoxy)methyl)phenyl)ethyl)-2-methylpropane-2-sulfinamide $AlMe_3$ (2 M in toluene, 741 µL, 1.48 mmol) was added to a solution of (R,E)-N-(2-(tert-butyldimethylsilyloxy)ethylidene)-2-methylpropane-2-sulfinamide (325 mg, 1.17 mmol) in anhydrous toluene (1 mL) at −78° C. Then, in a second vial, BuLi (2.5 M in hexanes, 544 µL, 1.36 mmol) was added to a solution of 1-bromo-3-chloro-5-fluoro-2-((4-methoxyphenoxy)methyl)benzene (427 mg, 1.24 mmol) in dry toluene at −78° C. The solution was stirred for 15 min at this temperature. The 1-bromo-3-chloro-5-fluoro-2-((4-methoxyphenoxy)methyl)benzene-containing solution was slowly added to the (R,E)-N-(2-(tert-butyldimethylsilyloxy)ethylidene)-2-methylpropane-2-sulfinamide-containing solution at −78° C. The mixture was stirred for 22 h and allowed to reach RT. After complete conversion the reaction mixture was quenched with saturated aqueous $NH_4Cl$ solution. The mixture was extracted with EA and the combined organic phases were dried over $Na_2SO_4$, filtered and concentrated in vacuo. The crude product was purified by flash chromatography on silica gel (elution with EA/heptane) to yield the title compound. MS (m/z): 544.6 [M+H$^+$].

Step F. Synthesis of (R)-2-amino-2-(3-chloro-5-fluoro-2-((4-methoxyphenoxy)methyl)phenyl)ethanol (R)—N—((R)-2-(tert-butyldimethylsilyloxy)-1-(3-chloro-5-fluoro-2-((4-methoxyphenoxy)methyl)phenyl)ethyl)-2-methylpropane-2-sulfinamide (149 mg, 0.27 mmol) was reacted with 3 M methanolic HCl (274 µL, 0.82 mmol) according to the synthesis of (S)-1-(3-chloro-5-fluoro-2-((4-methoxyphenoxy)methyl)phenyl)ethanamine to give the title compound. MS (m/z): 370.3 [M+HCO$_2^-$].

Step G. Synthesis of (S)—N—((R)-1-(3-chloro-5-fluoro-2-((4-methoxyphenoxy)methyl)phenyl)-2-hydroxyethyl)-2-hydroxy-3-methylbutanamide PyBOP (279 mg, 0.53 mmol) and DIPEA (114 µL mg, 0.67 mmol) were subsequently added to a stirred solution of (R)-2-amino-2-(3-chloro-5-fluoro-2-((4-methoxyphenoxy)methyl)phenyl)ethanol (87.0 mg, 0.27 mmol) and (S)-(+)-2-hydroxy-3-methylbutyric acid (47.3 mg, 0.40 mmol) in DMF (1 mL) at 0° C. After stirring for 16 h at RT, the reaction mixture was concentrated in vacuo. The residue was re-dissolved in saturated methanolic ammonia solution, stirred at RT for 3 h and concentrated in vacuo. Purification of the remaining residue by flash chromatography on silica gel (elution with EA/heptane) afforded the title compound. MS (m/z): 426.4 [M+H$^+$].

Step H. Synthesis of (S)-1-((R)-2-(benzoyloxy)-1-(3-chloro-5-fluoro-2-((4-methoxyphenoxy)methyl)phenyl)ethylamino)-3-methyl-1-oxobutan-2-yl benzoate Pyridine (300 µL) and benzoyl chloride (89.3 µL, 0.77 mmol) were subsequently added to a stirred solution of (S)—N—((R)-1-(3-chloro-5-fluoro-2-((4-methoxyphenoxy)methyl)phenyl)-2-hydroxyethyl)-2-hydroxy-3-methylbutanamide (131 mg, 0.31 mmol) in DCM (1 mL). After stirring for 23 h at RT, the reaction mixture was concentrated in vacuo. The remaining residue was re-dissolved in toluene (2 mL) and concentrated in vacuo. The crude product was purified by flash chromatography on silica gel (elution with EA/heptane) to give the title compound. MS (m/z): 634.3 [M+H$^+$].

Step I. Synthesis of (S)-1-((R)-2-(benzoyloxy)-1-(3-chloro-5-fluoro-2-(hydroxymethyl)phenyl)ethylamino)-3-methyl-1-oxobutan-2-yl benzoate (S)-1-((R)-2-(benzoyloxy)-1-(3-chloro-5-fluoro-2-((4-methoxyphenoxy)methyl)phenyl)ethylamino)-3-methyl-1-oxobutan-2-yl benzoate (141 mg, 0.22 mmol) in ACN (2 mL) was reacted with ammonium cerium(IV) nitrate (304 mg. 0.56 mmol) in water (400 µL) according to the synthesis of (S)-2-(1-(3-chloro-5-fluoro-2-(hydroxymethyl)phenyl)ethyl)isoindoline-1,3-dione. The crude product was purified by flash chromatography on silica gel (elution with EA/heptane) to give the title compound. MS (m/z): 528.5 [M+H$^+$].

Step J. Synthesis of (S)-1-((R)-2-(benzoyloxy)-1-(3-chloro-2-(chloromethyl)-5-fluorophenyl)ethylamino)-3-methyl-1-oxobutan-2-yl benzoate (S)-1-((R)-2-(benzoyloxy)-1-(3-chloro-5-fluoro-2-(hydroxymethyl)phenyl)ethylamino)-3-methyl-1-oxobutan-2-yl benzoate (48.3 mg, 0.09 mmol) was reacted with $SOCl_2$ (13.3 µL, 0.18 mmol) according to the synthesis of (S)-2-(1-(3-chloro-2-(chloromethyl)-5-fluorophenyl)ethyl)isoindoline-1,3-dione to give the title compound. MS (m/z): 546.6 [M+H$^+$].

Step K. Synthesis of (S)-1-((R)-2-(benzoyloxy)-1-(3-chloro-5-fluoro-2-((4-(4-fluoro-1H-pyrazol-1-yl)-2-methylquinolin-8-yloxy)methyl)phenyl)ethylamino)-3-methyl-1-oxobutan-2-yl benzoate $Cs_2CO_3$ (89.4 mg, 0.28 mmol) was added to a stirred solution of (S)-1-((R)-2-(benzoyloxy)-1-(3-chloro-2-(chloromethyl)-5-fluorophenyl)ethylamino)-3-methyl-1-oxobutan-2-yl benzoate (46.8 mg, 0.09 mmol) and 4-(4-fluoro-1H-pyrazol-1-yl)-2-methylquinolin-8-ol (24.5 mg, 0.10 mmol) in dry ACN (1 mL). After stirring over night, water (3 mL) was added and the mixture was extracted with DCM. The combined organic layers were washed with brine, dried over $Na_2SO_4$, filtered and concentrated in vacuo. The residue was purified by flash chromatography on silica gel (elution with EA/heptane) to give the title compound. MS (m/z): 753.4 [M+H$^+$].

Step L. Synthesis of (S)—N—((R)-1-(3-chloro-5-fluoro-2-((4-(4-fluoro-1H-pyrazol-1-yl)-2-methylquinolin-8-yloxy)methyl)phenyl)-2-hydroxyethyl)-2-hydroxy-3-methylbutanamide A solution of (S)-1-((R)-2-(benzoyloxy)-1-(3-chloro-5-fluoro-2-((4-(4-fluoro-1H-pyrazol-1-yl)-2-methylquinolin-8-yloxy)methyl)phenyl)ethylamino)-3-methyl-1-oxobutan-2-yl benzoate (46.2 mg, 0.06 mmol) in concentrated methanolic ammonia was stirred over night at RT. After complete conversion (TLC), the reaction mixture was concentrated in vacuo. Purification of the residue by reverse phase HPLC afforded the title compound. MS (m/z): 545.2 [M+H⁺].

Step M. Synthesis of (R,E)-N-(2-(tert-butyldimethylsilyloxy)ethylidene)-2-methylpropane-2-sulfinamide A solution of titan(IV)ethoxide (363 μL, 1.73 mmol), (R)-(+)-2-methyl-2-propanesulfinamide (210 mg, 1.73 mmol) and (tert-butyldimethylsilyloxy)acetaldehyde (300 μL, 1.58 mmol) in dry DCM (15 mL) under an atmosphere of Nitrogen was stirred at RT for 22 h. After complete conversion (TLC) the reaction was quenched with water (15 mL) and filtered over a pad of celite. Subsequently, the filter was carefully rinsed with DCM (2×15 mL). The aqueous phase was extracted with DCM (10 mL) and the combined organic layers were dried over Na₂SO₄, filtered and concentrated in vacuo to yield the title compound.

Example 6: Preparation of Compound No. 6

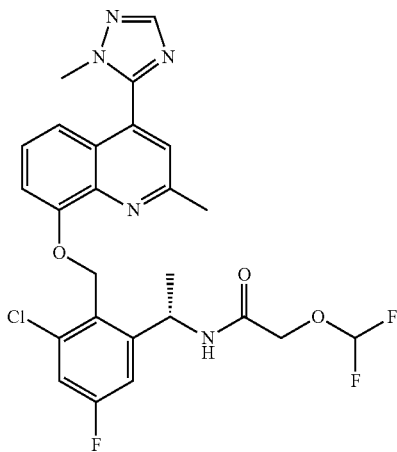 [SMILES: Cc1cc(-c2ncnn2C)c2cccc(OCc3c(Cl)cc(F)cc3[C@H](C)NC(=O)COC(F)F)c2n1]

(S)—N-(1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide

Step A. Synthesis of 8-methoxy-2-methyl-4-(1-methyl-1H-1,2,4-triazol-5-yl)quinoline 4-Chloro-8-methoxy-2-methylquinoline (5.00 g, 24.15 mmol), 1-methyl-1,2,4-triazole (42.74 mL, 48.30 mmol), K₂CO₃ (6.67 g, 48.30 mmol), Pd(OAc)₂ (0.54 g, 2.41 mmol), tricyclohexylphosphine tetrafluoroborate (1.87 g, 5.07 mmol), and trimethylacetic acid (2.47 g, 24.15 mmol) were suspended in dry xylene (20 mL). The flask was evacuated and subsequently ventilated with nitrogen. The degassing procedure was repeated twice. The mixture was heated to 140° C. for 18 h. After complete conversion, the mixture was evaporated and purified by flash chromatography on silica gel (elution with DCM/methanol) to give the title compound. MS (m/z): 255.4 [M+H⁺].

Step B. Synthesis of 2-methyl-4-(1-methyl-1H-1,2,4-triazol-5-yl)quinolin-8-ol A solution of 8-methoxy-2-methyl-4-(1-methyl-1H-1,2,4-triazol-5-yl)quinoline (3.14 g, 12.35 mmol) in anhydrous toluene (25 mL) was warmed to 80° C. and added dropwise to a vigorously stirred mixture of AlCl₃ (4.94 g, 37.06 mmol) in anhydrous toluene (25 mL). After stirring for 8 h at 80° C. the reaction mixture was cooled to 0° C. and quenched by the addition of water (68 mL) and subsequently conc. aqueous NH₃ until pH 10 (~1.7 mL). The mixture was centrifuged. The supernatant was extracted with EA and the combined organic layers were dried over Na₂SO₄, filtered, and concentrated in vacuo. The residue was purified by flash chromatography on silica gel (elution with DCM/methanol) to give the title compound. MS (m/z): 239.2 [M–H⁺].

Step C. Synthesis of (S)-2-(1-(3-chloro-5-fluoro-2-((2-methyl-4-(1-methyl-1H-1,2,4-triazol-5-yl)quinolin-8-yloxy)methyl)phenyl)ethyl)isoindoline-1,3-dione (S)-2-(1-(3-chloro-2-(chloromethyl)-5-fluorophenyl)ethyl)isoindoline-1,3-dione (34.3 mg, 97 μmol) was reacted with 2-methyl-4-(1-methyl-1H-1,2,4-triazol-5-yl)quinolin-8-ol (23.4 mg, 97 μmol) according to the synthesis of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione to give the title compound. MS (m/z): 556.3 [M–H⁺].

Step D. Synthesis of (S)-1-(3-chloro-5-fluoro-2-((2-methyl-4-(1-methyl-1H-1,2,4-triazol-5-yl)quinolin-8-yloxy)methyl)phenyl)ethanamine (S)-2-(1-(3-chloro-5-fluoro-2-((2-methyl-4-(1-methyl-1H-1,2,4-triazol-5-yl)quinolin-8-yloxy)methyl)phenyl)ethyl)isoindoline-1,3-dione (45.5 mg, 82 μmol) was deprotected according to the synthesis of (S)-1-(3-chloro-5-fluoro-2-((4-(4-fluoro-1H-pyrazol-1-yl)-2-methylquinolin-8-yloxy)methyl)phenyl)ethanamine to give the title compound. MS (m/z): 448.3 [M+Na⁺].

Step E. Synthesis of (S)—N-(1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide (S)-1-(3-chloro-5-fluoro-2-((2-methyl-4-(1-methyl-1H-1,2,4-triazol-5-yl)quinolin-8-yloxy)methyl)phenyl)ethanamine (28.9 mg, 68 μmol) and 2-(difluoromethoxy)acetic acid (11.1 mg, 88 μmol) was reacted according to the synthesis of (R)—N—((S)-1-(3-chloro-5-fluoro-2-((4-(4-fluoro-1H-pyrazol-1-yl)-2-methylquinolin-8-yloxy)methyl)

phenyl)ethyl)-2-hydroxypropanamide to give the title compound. MS (m/z): 535.0 [M+H$^+$].

Example 7: Preparation of Compound No. 7

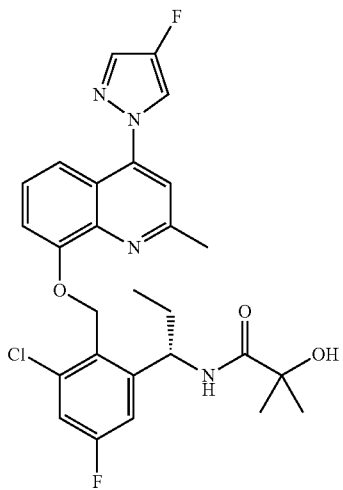 [SMILES: CC[C@H](NC(=O)C(C)(C)O)c1cc(F)cc(Cl)c1COc1cccc2c(-n3cc(F)cn3)cc(C)nc12]

(S)—N-(1-(3-chloro-5-fluoro-2-((4-(4-fluoro-1H-pyrazol-1-yl)-2-methylquinolin-8-yloxy)methyl)phenyl)ethyl)-2-hydroxy-2-methylpropanamide Step A. Synthesis of (3-chloro-5-fluoro-2-((4-methoxyphenoxy)methyl)phenyl)methanol LiBH$_4$ (200 mg, 9.3 mmol) was added in several portions to a stirred solution of methyl 3-chloro-5-fluoro-2-((4-methoxyphenoxy)methyl)benzoate (347 mg, 0.81 mmol) in THF (8.9 mL) and MeOH (2 mL) at RT over a period of 3 h. After stirring for 1 h at RT, the reaction mixture was partitioned between DCM (20 mL) and water (10 mL). The aqueous layer was extracted with DCM (2×15 mL). The combined organic layers were dried over Na$_2$SO$_4$, filtered, and concentrated in vacuo. The residue was purified by flash chromatography on silica gel (elution with EA/heptane) to give the title compound.

Step B. Synthesis of 3-chloro-5-fluoro-2-((4-methoxyphenoxy)methyl)benzaldehyde (3-Chloro-5-fluoro-2-((4-methoxyphenoxy)methyl)phenyl)methanol (1.70 g, 5.73 mmol) was dissolved in a 1:1-mixture of dioxane and toluene (70 mL) and manganese(IV) oxide (9.96 g, 114.59 mmol) was added. The reaction mixture was stirred at RT until complete reaction (TLC). After filtration over Celite, the filtrate was evaporated under reduced pressure to give the title compound.

Step C. Synthesis of (R,E)-N-(3-chloro-5-fluoro-2-((4-methoxyphenoxy)methyl)benzylidene)-2-methylpropane-2-sulfinamide Under an atmosphere of argon 3-chloro-5-fluoro-2-((4-methoxyphenoxy)methyl)benzaldehyde (317 mg, 1.08 mmol) and (R)-$^t$Bu-sulfinylamide (143 µL, 1.18 mmol) were dissolved in anhydrous THF (5 mL). Subsequently, Titan(IV)ethoxide (676.5 mL, 3.23 mmol) was added dropwise. The reaction mixture was stirred at 65° C. over night. After completion of the reaction the reaction mixture was quenched with water. The aqueous layer was extracted 3× with DCM. The combined organic layers were dried over Na$_2$SO$_4$, filtered and evaporated to dryness under reduced pressure to give the title compound. MS (m/z): 420.1 [M+Na].

Step D. Synthesis of (R)—N—((R)-1-(3-chloro-5-fluoro-2-((4-methoxyphenoxy)methyl)phenyl)propyl)-2-methylpropane-2-sulfinamide and (R)—N—((S)-1-(3-chloro-5-fluoro-2-((4-methoxyphenoxy)methyl)phenyl)propyl)-2-methylpropane-2-sulfinamide (R,E)-N-(3-chloro-5-fluoro-2-((4-methoxyphenoxy)methyl)benzylidene)-2-methylpropane-2-sulfinamide (352.0 mg, 884.67 µmol) was dissolved in THF (20 mL). A 1 M solution of ethylmagnesium bromide in THF (2.21 mL, 2.21 mmol) was added dropwise. The reaction mixture was stirred at RT over night. Ice was added cautiously before dilution with sat. aqueous NH$_4$Cl-solution. The aqueous phase was extracted 3× with DCM. The combined organic layers were dried over Na$_2$SO$_4$ and, after filtration, evaporated to dryness under reduced pressure. The crude product was purified by flash chromatography on silica gel (elution with EA/heptane) to give the title compounds. R-isomer: MS (m/z): 428.3 [M+H$^+$] and S-isomer: MS (m/z): 428.0 [M+H$^+$].

Step E. Synthesis of (S)-1-(3-chloro-5-fluoro-2-((4-methoxyphenoxy)methyl)phenyl)propan-1-amine (R)—N—((S)-1-(3-chloro-5-fluoro-2-((4-methoxyphenoxy)methyl)phenyl)propyl)-2-methylpropane-2-sulfinamide (182 mg, 425 µmol) was reacted with 3M methanolic HCl solution according to the synthesis of (S)-1-(3-chloro-5-fluoro-2-((4-methoxyphenoxy)methyl)phenyl)ethanamine to give the title compound. MS (m/z): 324.1 [M+H$^+$].

Step F. Synthesis of (S)-2-(1-(3-chloro-5-fluoro-2-((4-methoxyphenoxy)methyl)phenyl)propyl)isoindoline-1,3-dione (S)-1-(3-chloro-5-fluoro-2-((4-methoxyphenoxy)methyl)phenyl)propan-1-amine (95.4 mg, 295 µmol) was reacted with phthalic anhydride (48 mg, 324 µmol) according to the synthesis of (S)-2-(1-(3-chloro-5-fluoro-2-((4-methoxyphenoxy)methyl)phenyl)ethyl)isoindoline-1,3-dione to give the title compound. MS (m/z): 454.6 [M+H$^+$].

Step G. Synthesis of (S)-2-(1-(3-chloro-5-fluoro-2-(hydroxymethyl)phenyl)propyl)isoindoline-1,3-dione (S)-2-(1-(3-chloro-5-fluoro-2-((4-methoxyphenoxy)methyl)phenyl)propyl)isoindoline-1,3-dione (102 mg, 225 µmol) was reacted with ammonium cerium(IV) nitrate (308 mg, 562 µmol) according to the synthesis of (S)-2-(1-(3-chloro-5-fluoro-2-(hydroxymethyl)phenyl)ethyl)isoindoline-1,3-dione to give the title compound. MS (m/z): 370.3 [M+Na].

Step H. Synthesis of (S)-2-(1-(3-chloro-2-(chloromethyl)-5-fluorophenyl)propyl)isoindoline-1,3-dione (S)-2-(1-(3-chloro-5-fluoro-2-(hydroxymethyl)phenyl)propyl)isoindoline-1,3-dione (52.9 mg, 152 µmol) was reacted with SOCl$_2$ (22.06 μL, 304 μmol) according to the synthesis of (S)-2-(1-(3-chloro-2-(chloromethyl)-5-fluorophenyl)ethyl)isoindoline-1,3-dione to give the title compound. MS (m/z): 388.3 [M+Na].

Step I. Synthesis of (S)-2-(1-(3-chloro-5-fluoro-2-((4-(4-fluoro-1H-pyrazol-1-yl)-2-methylquinolin-8-yloxy)methyl)phenyl)propyl)isoindoline-1,3-dione (S)-2-(1-(3-chloro-2-(chloromethyl)-5-fluorophenyl)propyl)isoindoline-1,3-dione (53.3 mg, 146 μmol) was reacted with 4-(4-fluoro-1H-pyrazol-1-yl)-2-methylquinolin-8-ol (35.4 mg, 146 μmol) according to the synthesis of methyl (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione to give the title compound. MS (m/z): 573.4 [M+H$^+$].

Step J. Synthesis of (S)-1-(3-chloro-5-fluoro-2-((4-(4-fluoro-1H-pyrazol-1-yl)-2-methylquinolin-8-yloxy)methyl)phenyl)propan-1-amine (S)-2-(1-(3-chloro-5-fluoro-2-((4-(4-fluoro-1H-pyrazol-1-yl)-2-methylquinolin-8-yloxy)methyl)phenyl)propyl)isoindoline-1,3-dione (80.8 mg, 141 μmol) was reacted with hydrazine hydrate (27.5 μL, 282 μmol) according to the synthesis of (S)-1-(3-chloro-5-fluoro-2-((4-(4-fluoro-1H-pyrazol-1-yl)-2-methylquinolin-8-yloxy)methyl)phenyl)ethanamine to give the title compound. MS (m/z): 444.1 [M+H$^+$].

Step K. Synthesis of (S)—N-(1-(3-chloro-5-fluoro-2-((4-(4-fluoro-1H-pyrazol-1-yl)-2-methylquinolin-8-yloxy)methyl)phenyl)propyl)-2-hydroxy-2-methylpropanamide (S)-1-(3-chloro-5-fluoro-2-((4-(4-fluoro-1H-pyrazol-1-yl)-2-methylquinolin-8-yloxy)methyl)phenyl)propan-1-amine (18 mg, 41 μmol) was reacted with alpha-hydroxyisobutyric acid (4.9 mg, 47 μmol) according to the synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide to give the title compound. MS (m/z): 529.6 [M+H$^+$].

Example 8: Preparation of Compound No. 8

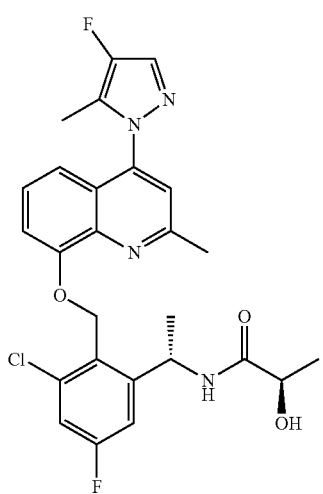 [SMILES: Cc1cc(-n2ncc(F)c2C)c2cccc(OCc3c(Cl)cc(F)cc3[C@H](C)NC(=O)[C@@H](C)O)c2n1]

(R)—N—((S)-1-(3-chloro-5-fluoro-2-((4-(4-fluoro-5-methyl-1H-pyrazol-1-yl)-2-methylquinolin-8-yloxy)methyl)phenyl)ethyl)-2-hydroxypropanamide Step A. Synthesis of 4-(4-fluoro-5-methyl-1H-pyrazol-1-yl)-8-methoxy-2-methylquinoline A mixture of 4-hydrazinyl-8-methoxy-2-methylquinoline (100 mg, 0.493 mmol) and 3-fluoro-4,4-dimethoxybutan-2-one (110 mg, 0.739 mmol) [Funabiki, K. et al *J. Chem. Soc., Perkin Trans.* 1 1997, 18, 2679-2680] in 5 M aqueous HCl (5.3 mL) was stirred at 90° C. for 1.5 h. The reaction mixture was concentrated in vacuo, partitioned between sat. aqueous NaHCO$_3$ (3 mL) and DCM (5 mL). The aqueous layer was extracted with DCM (2×5 mL), the combined organic layers were dried over Na$_2$SO$_4$, filtered and concentrated in vacuo. The residue was purified by flash chromatography on silica gel (elution with MeOH/DCM) to give the title compound. MS (m/z): 272.0 [M+H$^+$].

Step B. Synthesis of 4-(4-fluoro-5-methyl-1H-pyrazol-1-yl)-2-methylquinolin-8-ol 4-(4-fluoro-5-methyl-1H-pyrazol-1-yl)-8-methoxy-2-methylquinoline (118 mg, 0.436 mmol) was demethylated according to the synthesis of 4-(4-fluoro-H-pyrazol-1-yl)-2-methylquinolin-8-ol to give the title compound. MS (m/z): 258.1 [M+H$^+$].

Step C. Synthesis of (S)-2-(1-(3-chloro-5-fluoro-2-((4-(4-fluoro-5-methyl-1H-pyrazol-1-yl)-2-methylquinolin-8-yloxy)methyl)phenyl)ethyl)isoindoline-1,3-dione 4-(4-fluoro-5-methyl-1H-pyrazol-1-yl)-2-methylquinolin-8-ol (21.0 mg, 82 μmol) was reacted with (S)-2-(1-(3-chloro-2-(chloromethyl)-5-fluorophenyl)ethyl)isoindoline-1,3-dione (28.8 mg, 82 μmol) according to the synthesis of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione to give the title compound. MS (m/z): 573.1 [M+H$^+$].

Step D. Synthesis of (S)-1-(3-chloro-5-fluoro-2-((4-(4-fluoro-5-methyl-1H-pyrazol-1-yl)-2-methylquinolin-8-yloxy)methyl)phenyl)ethanamine (S)-2-(1-(3-chloro-5-fluoro-2-((4-(4-fluoro-5-methyl-1H-pyrazol-1-yl)-2-methylquinolin-8-yloxy)methyl)phenyl)ethyl)isoindoline-1,3-dione (31.1 mg, 54 μmol) was deprotected according to the synthesis of (S)-1-(3-chloro-5-fluoro-2-((4-(4-fluoro-1H-pyrazol-1-yl)-2-methylquinolin-8-yloxy)methyl)phenyl)ethanamine to give the title compound. MS (m/z): 465.4 [M+Na$^+$].

Step E. Synthesis of (R)—N—((S)-1-(3-chloro-5-fluoro-2-((4-(4-fluoro-5-methyl-1H-pyrazol-1-yl)-2-methylquinolin-8-yloxy)methyl)phenyl)ethyl)-2-hydroxypropanamide (S)-1-(3-chloro-5-fluoro-2-((4-(4-fluoro-5-methyl-1H-pyrazol-1-yl)-2-methylquinolin-8-yloxy)methyl)phenyl)ethanamine (20.5 mg, 46 μmol) was coupled with (R)-2-hydroxypropanoic acid (4.8 mg, 53 μmol) according to the synthesis of (R)—N—((S)-1-(3-chloro-5-fluoro-2-((4-(4-fluoro-1H-pyrazol-1-yl)-2-methylquinolin-8-yloxy)methyl)

phenyl)ethyl)-2-hydroxypropanamide to give the title compound. MS (m/z): 515.9 [M+H$^+$].

Example 9: Preparation of Compound No. 9 and Compound No. 10

Compound No. 9

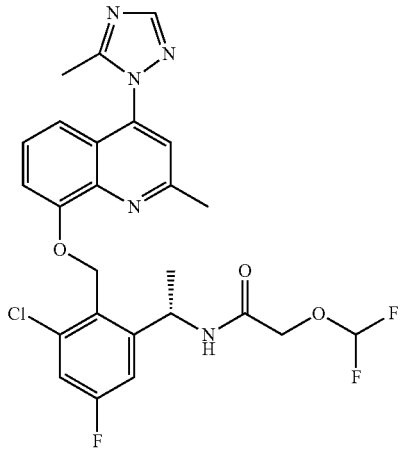

Compound No. 10

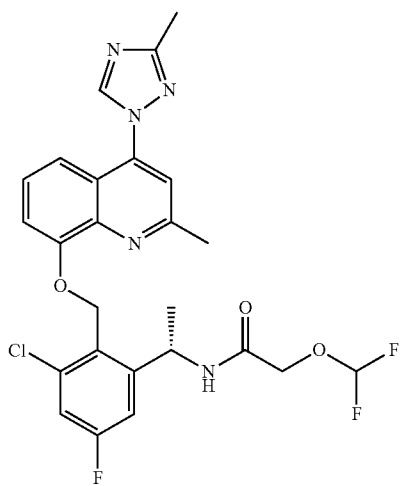

(S)—N-(1-(3-chloro-5-fluoro-2-((2-methyl-4-(5-methyl-1H-1,2,4-triazol-1-yl)quinolin-8-yloxy)methyl)phenyl)ethyl)-2-(difluoromethoxy)acetamide (9) and (S)—N-(1-(3-chloro-5-fluoro-2-((2-methyl-4-(3-methyl-1H-1,2,4-triazol-1-yl)quinolin-8-yloxy)methyl)phenyl)ethyl)-2-(difluoromethoxy)acetamide (10)

Step A. Synthesis of 8-methoxy-2-methyl-4-(5-methyl-1H-1,2,4-triazol-1-yl)quinoline and 8-methoxy-2-methyl-4-(3-methyl-1H-1,2,4-triazol-1-yl)quinoline 4-chloro-8-methoxy-2-methylquinoline (100 mg, 0.481 mmol) was reacted with 3-methyl-1H-1,2,4-triazole (46.0, 0.554 mmol) according to the synthesis of 4-(4-fluoro-1H-pyrazol-1-yl)-8-methoxy-2-methylquinoline to give a mixture of the title compounds. MS (m/z): 255.3 [M+H$^+$].

Step B. Synthesis of 2-methyl-4-(3-methyl-1H-1,2,4-triazol-1-yl)quinolin-8-ol and 2-methyl-4-(5-methyl-1H-1,2,4-triazol-1-yl)quinolin-8-ol A mixture of 8-methoxy-2-methyl-4-(5-methyl-1H-1,2,4-triazol-1-yl)quinoline and 8-methoxy-2-methyl-4-(3-methyl-1H-1,2,4-triazol-1-yl)quinoline (153 mg, 0.602 mmol) was demethylated according to the synthesis of 4-(4-fluoro-1H-pyrazol-1-yl)-2-methylquinolin-8-ol to give a mixture of the title compounds. MS (m/z): 241.1 [M+H$^+$].

Step C. Synthesis of (S)-2-(1-(3-chloro-5-fluoro-2-((2-methyl-4-(5-methyl-1H-1,2,4-triazol-1-yl)quinolin-8-yloxy)methyl)phenyl)ethyl)isoindoline-1,3-dione and (S)-2-(1-(3-chloro-5-fluoro-2-((2-methyl-4-(3-methyl-1H-1,2,4-triazol-1-yl)quinolin-8-yloxy)methyl)phenyl)ethyl)isoindoline-1,3-dione A mixture of 2-methyl-4-(3-methyl-1H-1,2,4-triazol-1-yl)quinolin-8-ol and 2-methyl-4-(5-methyl-1H-1,2,4-triazol-1-yl)quinolin-8-ol (48.3 mg, 0.201 mmol) was reacted with (S)-2-(1-(3-chloro-2-(chloromethyl)-5-fluorophenyl)ethyl)isoindoline-1,3-dione (70.7 mg, 0.201 mmol) according to the synthesis of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione to give a mixture of the title compounds. MS (m/z): 556.4 [M+H$^+$].

Step D. Synthesis of (S)-1-(3-chloro-5-fluoro-2-((2-methyl-4-(5-methyl-1H-1,2,4-triazol-1-yl)quinolin-8-yloxy)methyl)phenyl)ethanamine and (S)-1-(3-chloro-5-fluoro-2-((2-methyl-4-(3-methyl-1H-1,2,4-triazol-1-yl)quinolin-8-yloxy)methyl)phenyl)ethanamine A mixture of (S)-2-(1-(3-chloro-5-fluoro-2-((2-methyl-4-(5-methyl-1H-1,2,4-triazol-1-yl)quinolin-8-yloxy)methyl)phenyl)ethyl)isoindoline-1,3-dione and (S)-2-(1-(3-chloro-5-fluoro-2-((2-methyl-4-(3-methyl-1H-1,2,4-triazol-1-yl)quinolin-8-yloxy)methyl)phenyl)ethyl)isoindoline-1,3-dione (111 mg, 201 µmol) was deprotected according to the synthesis of (S)-1-(3-chloro-5-fluoro-2-((4-(4-fluoro-1H-pyrazol-1-yl)-2-methylquinolin-8-yloxy)methyl)phenyl)ethanamine to give the title compounds. MS (m/z): 448.3 [M+Na$^+$].

Step E. Synthesis of (S)—N-(1-(3-chloro-5-fluoro-2-((2-methyl-4-(5-methyl-1H-1,2,4-triazol-1-yl)quinolin-8-yloxy)methyl)phenyl)ethyl)-2-(difluoromethoxy)acetamide and (S)—N-(1-(3-chloro-5-fluoro-2-((2-methyl-4-(3-methyl-1H-1,2,4-triazol-1-yl)quinolin-8-yloxy)methyl)phenyl)ethyl)-2-(difluoromethoxy)acetamide A mixture of (S)-1-(3-chloro-5-fluoro-2-((2-methyl-4-(5-methyl-1H-1,2,4-triazol-1-yl)quinolin-8-yloxy)methyl)phenyl)ethanamine and (S)-1-(3-chloro-5-fluoro-2-((2-methyl-4-(3-methyl-1H-1,2,4-triazol-1-yl)quinolin-8-yloxy)methyl)phenyl)ethanamine (19 mg, 43 µmol) was reacted with 2-(difluoromethoxy)acetic acid (7.2 mg, 56 µmol) according to the synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide and purified by HPLC to yield (S)—N-(1-(3-chloro-5-fluoro-2-((2-methyl-4-(5-methyl-1H-1,2,4-triazol-1-yl)quinolin-8-yloxy)methyl)phenyl)ethyl)-2-(difluoromethoxy)acetamide (MS (m/z): 534.2 [M+H$^+$]) and (S)—N-(1-(3-chloro-5- fluoro-2-((2-methyl-4-(3-methyl-1H-1,2,4-triazol-1-yl)quinolin-8-yloxy)methyl)phenyl)ethyl)-2-(difluoromethoxy) acetamide (MS (m/z): 534.0 [M+H$^+$])

Example 10: Preparation of Compound No. 11

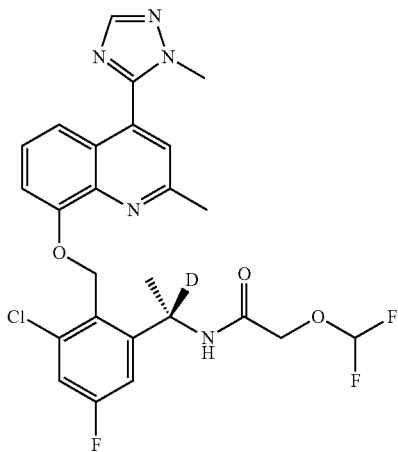 [SMILES: [2H][C@@](C)(NC(=O)COC(F)F)c1cc(F)cc(Cl)c1COc1cccc2c(-c3ncnn3C)cc(C)nc12]

(S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy) acetamide Step A. Synthesis of (R)—N—((S)-1-deutero-1-(3-chloro-5-fluoro-2-((4-methoxyphenoxy)methyl)phenyl)ethyl)-2-methylpropane-2-sulfinamide Preparation of deutero-L-Selectride solution: Anhydrous MeOH (0.591 mL, 14.6 mmol) was added to a stirred suspension of LiAlD$_4$ (203 mg, 4.86 mmol) at 0° C. within 10 min. The reaction mixture was allowed to reach RT and tri-sec-butylborane solution (1 M in THF, 3.6 mL, 3.6 mmol) was then added. The deutero-L-selectride solution was used after stirring for 15 min at RT.

Titan(IV)ethoxide (1.02 mL, 4.86 mmol) was added dropwise under an Argon atmosphere to a solution of 1-(3-chloro-5-fluoro-2-((4-methoxyphenoxy)methyl)phenyl) ethanone (0.500 g, 1.62 mmol) and (R)-(+)-2-methyl-2-propanesulfinamide (216 mg, 1.78 mmol) in anhydrous THF (1.7 mL). The mixture was heated under reflux until complete conversion (TLC). Subsequently, the mixture was cooled to 0° C. and the deutero-L-Selectride solution was added dropwise. The mixture was stirred at this temperature until complete conversion (TLC). Subsequently, methanol (~10 mL) was added until evolution of gas stopped. The solution was poured into sat. aqueous NaCl solution (5 mL). Then, the mixture was filtrated over a pad of Celite and carefully rinsed with DCM. The filtrate was washed with sat. aqueous NaCl solution. The aqueous layer was extracted with DCM. The combined organic layers were dried over Na$_2$SO$_4$, filtrated, and evaporated to dryness. The remaining residue was purified by flash chromatography on silica gel (elution with EA/heptane) to give the title compound. MS (m/z): 415.3 [M+H$^+$].

Step B. Synthesis of (S)-1-deutero-1-(3-chloro-5-fluoro-2-((4-methoxyphenoxy)methyl)phenyl) ethanamine (R)—N—((S)-1-deutero-1-(3-chloro-5-fluoro-2-((4-methoxyphenoxy)methyl)phenyl)ethyl)-2-methylpropane-2-sulfinamide (323 mg, 779 µmol) was hydrolyzed according to the synthesis of (S)-1-(3-chloro-5-fluoro-2-((4-methoxyphenoxy)methyl)phenyl)ethanamine to give the title compound. MS (m/z): 311.7 [M+H$^+$].

Step C. Synthesis of (S)—N-(1-deutero-1-(3-chloro-5-fluoro-2-((4-methoxyphenoxy)methyl)phenyl)ethyl)-2-(difluoromethoxy)acetamide (S)-1-Deutero-1-(3-chloro-5-fluoro-2-((4-methoxyphenoxy)methyl)phenyl)ethanamine (50.0 mg, 161 µmol) was coupled with 2-(difluoromethoxy)acetic acid (26.4 mg, 209 µmol) according to the synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide to give the title compound. MS (m/z): 419.2 [M+H$^+$].

Step D. Synthesis of (S)—N-(1-deutero-1-(3-chloro-5-fluoro-2-(hydroxymethyl)phenyl)ethyl)-2-(difluoromethoxy)acetamide (S)—N-(1-deutero-1-(3-chloro-5-fluoro-2-((4-methoxyphenoxy)methyl)phenyl)ethyl)-2-(difluoromethoxy)acetamide (38 mg, 91 µmol) was deprotected according to the synthesis of (S)-2-(1-(3-chloro-5-fluoro-2-(hydroxymethyl) phenyl)ethyl)isoindoline-1,3-dione to give the title compound. MS (m/z): 312.7 [M+H$^+$].

Step E. Synthesis of (S)—N-(1-deutero-1-(3-chloro-2-(chloromethyl)-5-fluorophenyl)ethyl)-2-(difluoromethoxy)acetamide (S)—N-(1-deutero-1-(3-chloro-5-fluoro-2-(hydroxymethyl)phenyl)ethyl)-2-(difluoromethoxy)acetamide (19 mg, 61 µmol) was chlorinated according to the synthesis of (S)-2-(1-(3-chloro-2-(chloromethyl)-5-fluorophenyl)ethyl) isoindoline-1,3-dione to give the title compound. MS (m/z): 330.7 [M+H$^+$].

Step F. Synthesis of (S)—N-(1-deutero-1-(3-chloro-5-fluoro-2-((2-methyl-4-(1-methyl-1H-1,2,4-triazol-5-yl)quinolin-8-yloxy)methyl)phenyl)ethyl)-2-(difluoromethoxy)acetamide (S)—N-(1-deutero-1-(3-chloro-2-(chloromethyl)-5-fluorophenyl)ethyl)-2-(difluoromethoxy)acetamide (20 mg, 57 µmol) was reacted with 2-methyl-4-(1-methyl-1H-1,2,4-triazol-5-yl)quinolin-8-ol (14 mg, 57 µmol) according to the synthesis of (S)-2-(1-(3-chloro-5-fluoro-2-((4-(4-fluoro-1H-pyrazol-1-yl)-2-methylquinolin-8-yloxy)methyl)phenyl) ethyl)isoindoline-1,3-dione to give the title compound. MS (m/z): 535.4 [M+H$^+$].

Example 10A: Preparation of Compound No. 11A

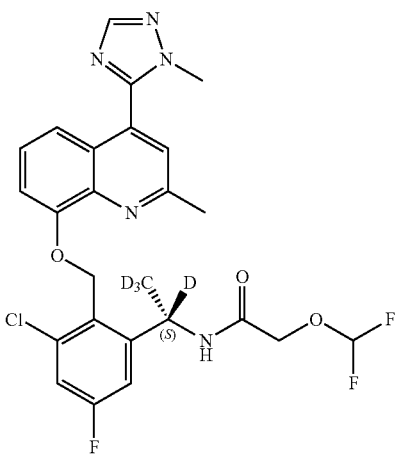

N-[(1S)-1-[3-chloro-5-fluoro-2-({[2-methyl-4-(1-methyl-1H-1,2,4-triazol-5-yl)quinolin-8-yl]oxy}methyl)phenyl](1,2,2,2-$^2$H$_4$)ethyl]-2-(difluoromethoxy)acetamide Step A: (S)—N-[(1,2,2,2-$^2$H$_4$)ethylidene]-2-methylpropane-2-sulfinamide (1,2,2,2-$^2$H$_4$)Acetaldehyde (1.00 g, 15.6 mmol was reacted with (S)-2-methylpropane-2-sulfinamide (2.07 g, 17.1 mmol) according to the synthesis of (R,E)-N-(2-(tert-butyldimethylsilyloxy)ethylidene)-2-methylpropane-2-sulfinamide to give the title compound.

Step B: Synthesis of (S)—N-[(1S)-1-{3-chloro-5-fluoro-2-[(4-methoxyphenoxy)methyl]phenyl}(1,2,2,2-$^2$H$_4$)ethyl]-2-methylpropane-2-sulfinamide 1-Bromo-3-chloro-5-fluoro-2-((4-methoxyphenoxy)methyl)benzene (272.0 mg, 0.79 mmol) was reacted with (S)—N-[(1,2,2,2-$^2$H$_4$)ethylidene]-2-methylpropane-2-sulfinamide (113 mg, 0.75 mmol) according to the synthesis of (R)—N—((R)-2-(tert-butyldimethylsilyloxy)-1-(3-chloro-5-fluoro-2-((4-methoxyphenoxy)methyl)phenyl)ethyl)-2-methylpropane-2-sulfinamide to give the title compound. MS (m/z): 440.5 [M+Na$^+$]

Step C: Synthesis of (1S)-1-{3-chloro-5-fluoro-2-[(4-methoxyphenoxy)methyl]phenyl}($^2$H$_4$)ethan-1-amine (S)—N-[(1S)-1-{3-chloro-5-fluoro-2-[(4-methoxyphenoxy)methyl]phenyl}(1,2,2,2-$^2$H$_4$)ethyl]-2-methylpropane-2-sulfinamide (86.5 mg, 0.21 mmol) dissolved in methanol (1 mL) was reacted with 3 M methanolic HCl (207 µL, 0.62 mmol) according to the synthesis of (S)-1-(3-chloro-5-fluoro-2-((4-methoxyphenoxy)methyl)phenyl)ethanamine to yield the title compound. MS (m/z): 314.9 [M+H$^+$]

Step D: Synthesis of N—[(S)-1-{3-chloro-5-fluoro-2-[(4-methoxyphenoxy)methyl]phenyl}(1,2,2,2-$^2$H$_4$)ethyl]-2-(difluoromethoxy)acetamide The reaction of (1S)-1-{3-chloro-5-fluoro-2-[(4-methoxyphenoxy)methyl]phenyl}($^2$H$_4$)ethan-1-amine (32 mg. 0.10 mmol) with 2-(difluoromethoxy)acetic acid (14 mg, 0.11 mmol), PyAOP (70 mg, 0.13 mmol), and DIPEA (21 µL, 0.18 mmol) according to the synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide yielded the crude title compound. It was purified by flash chromatography on silica gel (elution with EA/heptane) to give the title compound. MS (m/z): 444.4 [M+Na$^+$].

Step E: Synthesis of N-[(1S)-1-[3-chloro-5-fluoro-2-(hydroxymethyl)phenyl](1,2,2,2-$^2$H$_4$)ethyl]-2-(difluoromethoxy)acetamide N-[(1S)-1-{3-chloro-5-fluoro-2-[(4-methoxyphenoxy)methyl]phenyl}(1,2,2,2-$^2$H$_4$)ethyl]-2-(difluoromethoxy)acetamide (29 mg, 0.070 mmol) was reacted with ammonium cerium(IV) nitrate (95.7 mg, 0.175 mmol) according to the synthesis of (S)-2-(1-(3-chloro-5-fluoro-2-(hydroxymethyl)phenyl)ethyl)isoindoline-1,3-dione to give the tile compound.

Step F: Synthesis of N-[(1S)-1-[3-chloro-2-(chloromethyl)-5-fluorophenyl](1,2,2,2-$^2$H$_4$)ethyl]-2-(difluoromethoxy)acetamide N-[(1S)-1-[3-chloro-5-fluoro-2-(hydroxymethyl)phenyl](1,2,2,2-$^2$H$_4$)ethyl]-2-(difluoromethoxy)acetamide (18 mg, 0.057 mmol) was reacted with SOCl$_2$ (17 µL, 0.23 mmol) according to the synthesis of (S)-2-(1-(3-chloro-2-(chloromethyl)-5-fluorophenyl)ethyl)isoindoline-1,3-dione to give the tile compound.

Step G: Synthesis of N-[(1S)-1-[3-chloro-5-fluoro-2-({[2-methyl-4-(1-methyl-1H-1,2,4-triazol-5-yl)quinolin-8-yl]oxy}methyl)phenyl](1,2,2,2-$^2$H$_4$)ethyl]-2-(difluoromethoxy)acetamide N-[(1S)-1-[3-chloro-2-(chloromethyl)-5-fluorophenyl](1,2,2,2-$^2$H$_4$)ethyl]-2-(difluoromethoxy)acetamide (14.3 mg, 43 µmol) was reacted with 2-methyl-4-(1-methyl-1H-1,2,4-triazol-5-yl)quinolin-8-ol (11 mg, 47 µmol) according to the synthesis of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione The crude product was purified by HPLC to yield the title compound. MS (m/z): 539.2 [M+H$^+$].

Example 10B: Preparation of Compound No. 11B

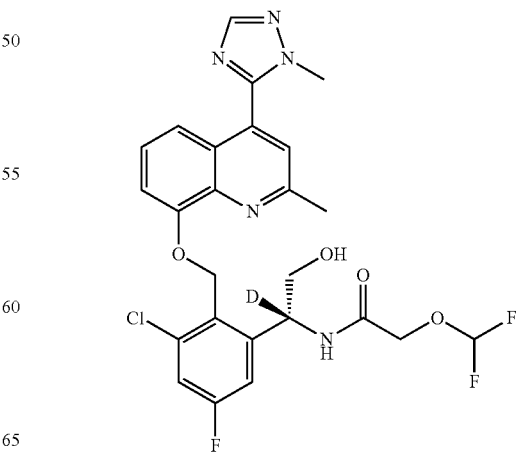

(R)—N-(1-Deutero-1-(3-chloro-5-fluoro-2-((2-methyl-4-(1-methyl-1H-1,2,4-triazol-5-yl)quinolin-8-yloxy)methyl)phenyl)-2-hydroxyethyl)-2-(difluoromethoxy)acetamide Step A. Synthesis of tert-butyldimethyl[2-oxo(2-$^2$H)ethoxy]silane A solution of methyl 2-(tert-butyldimethylsilyloxy)acetate (2.0 g, 10 mmol) in anhydrous Et$_2$O (8.9 mL) was added dropwise to a stirred suspension of LiAlD$_4$ (0.49 g, 12 mmol) in anhydrous Et$_2$O (35 mL) at −78° C. After stirring for 40 min at −78° C., the reaction was quenched by the addition of water (0.45 mL) and 15% aqueous NaOH-solution (0.45 mL) at −78° C. Water (1.34 mL) was then added and the mixture was allowed to warm to RT. The mixture was filtrated over a pad of Celite and the filtrate was concentrated in vacuo. The remaining residue was purified by flash chromatography on silica gel (elution with EA/heptane) to give the title compound.

Step B. Synthesis (R)—N-[(1E)-2-[(tert-butyldimethylsilyl)oxy](1-$^2$H)ethylidene]-2-methylpropane-2-sulfinamide A solution of titan(IV)ethoxide (794 µL, 3.79 mmol), (R)-(+)-2-methyl-2-propanesulfinamide (344 mg, 2.84 mmol) and tert-butyldimethyl[2-oxo(2-$^2$H)ethoxy]silane in anhydrous DCM (10 mL) was stirred under an atmosphere of nitrogen at RT for 16 h. After complete conversion (TLC) the reaction was quenched by the addition of water (20 mL) at 0° C. and the resulting mixture was filtered through a pad of Celite. Subsequently, the filter was carefully rinsed with DCM (2×20 mL). The aqueous layer was extracted with DCM (20 mL) and the combined organic layers were dried over Na$_2$SO$_4$, filtered and concentrated in vacuo. The remaining residue was purified by flash chromatography on silica gel (elution with EA/heptane) to give the title compound. MS (m/z): 279.2 [M+H$^+$].

Step C. Synthesis of (R)—N-(2-(tert-butyldimethylsilyloxy)-1-deutero-1-(3-chloro-5-fluoro-2-((4-methoxyphenoxy)methyl)phenyl)ethyl)pivalamide AlMe$_3$ (2 M in toluene, 551 µL, 1.10 mmol) was added to a solution of (R)—N—[(E)-2-[(tert-butyldimethylsilyl)oxy](1-$^2$H)ethylidene]-2-methylpropane-2-sulfinamide (279 mg, 1.00 mmol) in anhydrous toluene (1.6 mL) at −78° C. and the resulting solution was stirred for 30 min at −78° C. Then, in a second flask, BuLi (2.5 M in hexanes, 508 µL, 1.27 mmol) was added to a solution of 1-bromo-3-chloro-5-fluoro-2-((4-methoxyphenoxy)methyl)benzene (381 mg, 1.10 mmol) in anhydrous toluene (3.8 mL) at −78° C. and the resulting solution was stirred for 15 min at −78° C. The (R)—N-[(1E)-2-[(tert-butyldimethylsilyl)oxy](1-$^2$H)ethylidene]-2-methylpropane-2-sulfinamide-containing solution was then slowly added to the 1-bromo-3-chloro-5-fluoro-2-((4-methoxyphenoxy)methyl)benzene-containing solution at −78° C. The reaction mixture was allowed to reach RT within 4.5 h and was quenched by the addition of saturated aqueous NH$_4$Cl solution. The mixture was extracted with EA and the combined organic layers were dried over Na$_2$SO$_4$, filtered and concentrated in vacuo. The remaining residue was purified by flash chromatography on silica gel (elution with EA/heptane) to yield the title compound. MS (m/z): 567.0 [M+Na$^+$].

Step D. Synthesis of (R)—N-(1-Deutero-1-(3-chloro-5-fluoro-2-((2-methyl-4-(1-methyl-1H-1,2,4-triazol-5-yl)quinolin-8-yloxy)methyl)phenyl)-2-hydroxyethyl)-2-(difluoromethoxy)acetamide (R)—N-(2-(tert-butyldimethylsilyloxy)-1-deutero-1-(3-chloro-5-fluoro-2-((4-methoxyphenoxy)methyl)phenyl)ethyl)pivalamide (388 mg, 0.714 mmol) was deprotected according to the synthesis of (R)-2-amino-2-(3-chloro-5-fluoro-2-((4-methoxyphenoxy)methyl)phenyl)ethanol, followed by the amidation with 2-(difluoromethoxy)acetic acid according to the synthesis of (S)—N—((R)-1-(3-chloro-5-fluoro-2-((4-methoxyphenoxy)methyl)phenyl)-2-hydroxyethyl)-2-hydroxy-3-methylbutanamide, followed by benzoylation, 4-methoxyphenol removal and chlorination according to the synthesis of (S)-1-((R)-2-(benzoyloxy)-1-(3-chloro-5-fluoro-2-(hydroxymethyl)phenyl)ethylamino)-3-methyl-1-oxobutan-2-yl benzoate, followed by the reaction with 2-methyl-4-(1-methyl-1H-1,2,4-triazol-5-yl)quinolin-8-ol and subsequent debenzoylation according to the synthesis of (S)—N—((R)-1-(3-chloro-5-fluoro-2-((4-fluoro-1H-pyrazol-1-yl)-2-methylquinolin-8-yloxy)methyl)phenyl)-2-hydroxyethyl)-2-hydroxy-3-methylbutanamide to give the title compound. MS (m/z): 551.3 [M+H$^+$].

Example 10C: Preparation of Compound No. 11C

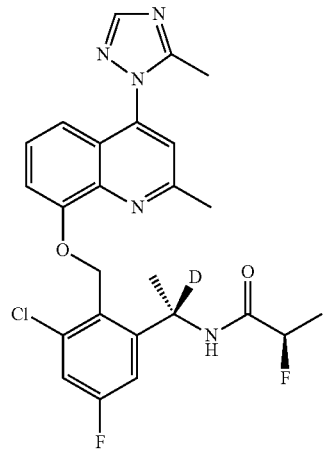 [SMILES: [2H][C@@](C)(NC(=O)[C@@H](C)F)c1cc(F)cc(Cl)c1COc1cccc2c(-n3ncnc3C)cc(C)nc12]

(R)—N—((S)-1-deutero-1-(3-chloro-5-fluoro-2-((2-methyl-4-(5-methyl-1H-1,2,4-triazol-1-yl)quinolin-8-yloxy)methyl)phenyl)ethyl)-2-fluoropropanamide Step A. Synthesis of 8-methoxy-2-methyl-4-(5-methyl-1H-1,2,4-triazol-1-yl)quinolineol Acetic anhydride (0.645 mL, 0.692 g, 6.78 mmol) was added to a stirred mixture of formamidine acetate salt (0.705 g, 6.78 mmol) in anhydrous DMF (23.1 mL) at RT. After stirring for 5 min at RT, Et$_3$N (1.56 mL, 1.14 g, 11.3 mmol) was added. After stirring for 5 min at RT, the reaction mixture was warmed to 80° C. and stirred until the reaction mixture became a clear solution. The reaction mixture was then allowed to cool to RT followed by the addition of acetic acid (3.10 mL, 3.25 g, 54.2 mmol) and 4-hydrazinyl-8-methoxy-2-methylquinoline [A. A. Avetisyan et al. *Russ. J.* of *Org. Chem.* 2010 46(3), 427-431] (0.918 g, 4.52 mmol). After stirring for 17 h at 80° C., the reaction mixture was concentrated in vacuo. The residue was purified by flash chromatography on silica gel (elution with DCM/MeOH) to give the title compound. MS (m/z): 255.2 [M+H$^+$].

Step B. Synthesis of 2-methyl-4-(5-methyl-1H-1,2,4-triazol-1-yl)quinolin-8-ol 2-Methyl-4-(5-methyl-1H-1,2,4-triazol-1-yl)quinolin-8-ol (0.750 g, 2.95 mmol) was demethylated with AlCl$_3$ (1.18 g, 8.85 mmol) according to the synthesis of 4-(4-fluoro-H-pyrazol-1-yl)-2-methylquinolin-8-ol to give the title compound. MS (m/z): 240.8 [M+H$^+$].

Step C. Synthesis of (S)—N—((S)-1-deutero-1-(3-chloro-5-fluoro-2-((4-methoxyphenoxy)methyl)phenyl)ethyl)-2-hydroxypropanamide (S)-1-deutero-1-(3-chloro-5-fluoro-2-((4-methoxyphenoxy)methyl)phenyl)ethanamine (250 mg, 0.804 mmol) was reacted with L-(+)lactic acid (76 µL, 76 mg, 0.85 mmol) according to the synthesis of (R)—N—((S)-1-(3-chloro-5-fluoro-2-((4-(4-fluoro-1H-pyrazol-1-yl)-2-methylquinolin-8-yloxy)methyl)phenyl)ethyl)-2-hydroxypropanamide to give the tile compound. MS (m/z): 383.7 [M+H$^+$].

Step D. Synthesis of (R)—N—((S)-1-deutero-1-(3-chloro-5-fluoro-2-((4-methoxyphenoxy)methyl)phenyl)ethyl)-2-fluoropropanamide 1,8-Diazabicyclo[5.4.0]undec-7-ene (170 µL, 173 mg, 1.14 mmol) and perfluoro-1-butanesulfonyl fluoride (200 µL, 343 mg, 1.14 mmol) was subsequently added to a stirred solution of (S)—N—((S)-1-deutero-1-(3-chloro-5-fluoro-2-((4-methoxyphenoxy)methyl)phenyl)ethyl)-2-hydroxypropanamide (290 mg, 0.758 mmol) in anhydrous toluene (8 mL) at 0° C. After stirring for 30 min at 0° C., the reaction mixture was allowed to reach RT and stirred overnight at RT. The reaction mixture was then poured onto ice/water and extracted with DCM (3×20 mL). The combined organic layers were dried over Na$_2$SO$_4$, filtrated, and concentrated in vacuo. The remaining residue was purified by flash chromatography on silica gel (elution with EA/heptane) to give the title compound. MS (m/z): 385.9 [M+H$^+$].

Step E. Synthesis of (R)—N—((S)-1-deutero-1-(3-chloro-5-fluoro-2-(hydroxymethyl)phenyl)ethyl)-2-fluoropropanamide (R)—N—((S)-1-deutero-1-(3-chloro-5-fluoro-2-((4-methoxyphenoxy)methyl)phenyl)ethyl)-2-fluoropropanamide (96 mg, 0.25 mmol) was reacted with ammonium cerium (IV) nitrate (342 mg, 0.624 mmol) according to the synthesis of (S)-2-(1-(3-chloro-5-fluoro-2-(hydroxymethyl)phenyl)ethyl)isoindoline-1,3-dione to give the tile compound. MS (m/z): 276.8 [M–H$^+$].

Step F. Synthesis of (R)—N—((S)-1-deutero-1-(3-chloro-2-(chloromethyl)-5-fluorophenyl)ethyl)-2-fluoropropanamide (R)—N—((S)-1-deutero-1-(3-chloro-5-fluoro-2-(hydroxymethyl)phenyl)ethyl)-2-fluoropropanamide (47 mg, 0.17 mmol) was reacted with SOCl$_2$ (49 µL, 0.68 mmol) according to the synthesis of (S)-2-(1-(3-chloro-2-(chloromethyl)-5-fluorophenyl)ethyl)isoindoline-1,3-dione to give the tile compound. MS (m/z): 294.8 [M–H$^+$].

Step G. Synthesis of (R)—N—((S)-1-deutero-1-(3-chloro-5-fluoro-2-((2-methyl-4-(5-methyl-1H-1,2,4-triazol-1-yl)quinolin-8-yloxy)methyl)phenyl)ethyl)-2-fluoropropanamide (R)—N—((S)-1-deutero-1-(3-chloro-2-(chloromethyl)-5-fluorophenyl)ethyl)-2-fluoropropanamide (29 mg, 0.10 mmol) was reacted with 2-methyl-4-(5-methyl-1H-1,2,4-triazol-1-yl)quinolin-8-ol (26 mg, 0.11 mmol) according to the synthesis of (S)-2-(1-(3-chloro-5-fluoro-2-((4-(4-fluoro-1H-pyrazol-1-yl)-2-methylquinolin-8-yloxy)methyl)phenyl)ethyl)isoindoline-1,3-dione to give the tile compound. MS (m/z): 501.8[M+H$^+$].

Example 11: Compounds Nos. 12 to 213

The compounds Nos. 12 to 213 shown in the following Table 1 are further representative examples of compounds according to general formula (I) of the present invention. These compounds have been synthesized using the methods described above, together with synthetic methods disclosed in the references cited herein or known in the art of synthetic organic chemistry, and variations thereon as appreciated by those skilled in the art. Each of the references cited herein in relation to the routes of synthesis described in Examples 1 to 10C is hereby incorporated by reference in its entirety in the present specification. In any event, those skilled in the art of organic synthesis will recognize the starting materials and reaction conditions including variations to produce the compounds.

TABLE 1

Example Compounds Nos. 12 to 213

| Cpd No. | Structure | Mass# |
|---|---|---|
| 12. | 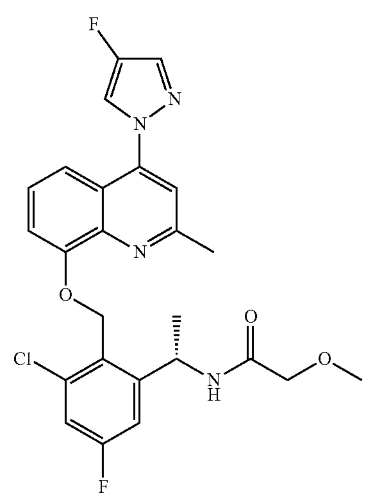 [SMILES: COCC(=O)N[C@@H](C)c1cc(F)cc(Cl)c1COc1cccc2c(-n3cc(F)cn3)cc(C)nc12] | 501.1 |

TABLE 1-continued

Example Compounds Nos. 12 to 213

| Cpd No. | Structure | Mass# |
|---|---|---|
| 13. | 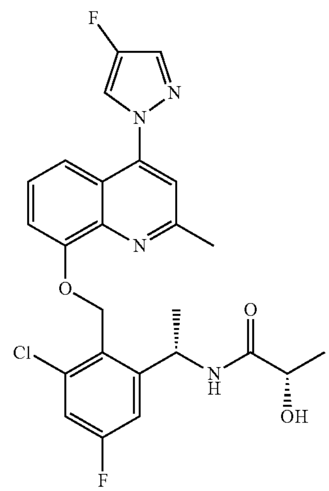 [SMILES: Cc1cc(-n2cc(F)cn2)c2cccc(OCc3c(Cl)cc(F)cc3[C@H](C)NC(=O)[C@H](C)O)c2n1] | 501.0 |
| 14. | 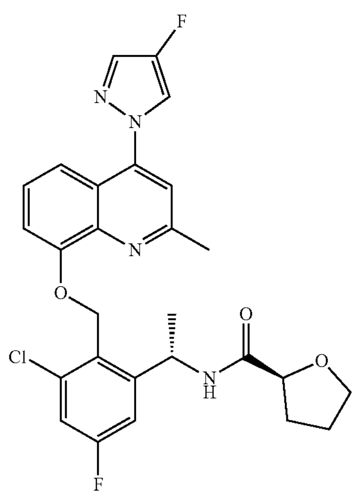 [SMILES: Cc1cc(-n2cc(F)cn2)c2cccc(OCc3c(Cl)cc(F)cc3[C@H](C)NC(=O)[C@@H]3CCCO3)c2n1] | 527.1 |
| 15. | 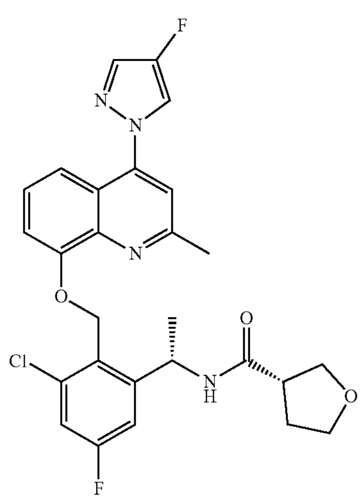 [SMILES: Cc1cc(-n2cc(F)cn2)c2cccc(OCc3c(Cl)cc(F)cc3[C@H](C)NC(=O)[C@H]3CCOC3)c2n1] | 527.0 |
| 16. | | 515.1 |
| 17. | | 515.1 |
| 18. | | 515.1 |

TABLE 1-continued

Example Compounds Nos. 12 to 213

| Cpd No. | Structure | Mass# |
|---|---|---|
| 19. | 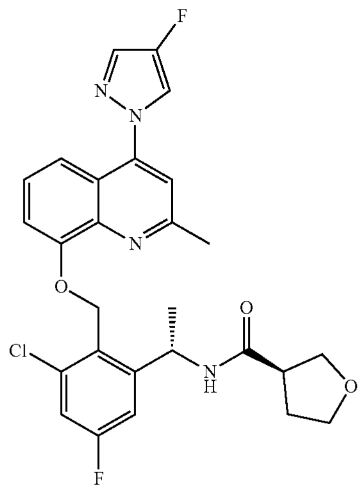 [SMILES: Cc1cc(-n2cc(F)cn2)c2cccc(OCc3c(Cl)cc(F)cc3[C@H](C)NC(=O)[C@@H]3CCOC3)c2n1] | 527.1 |
| 20. | 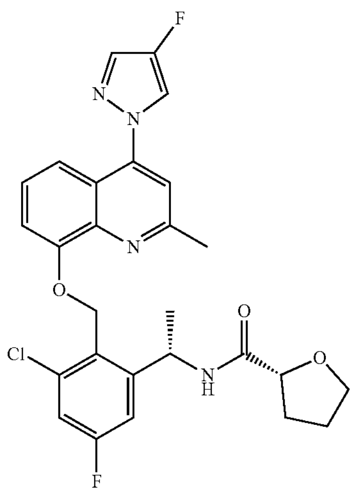 [SMILES: Cc1cc(-n2cc(F)cn2)c2cccc(OCc3c(Cl)cc(F)cc3[C@H](C)NC(=O)[C@H]3CCCO3)c2n1] | 528.0 |
| 21. | 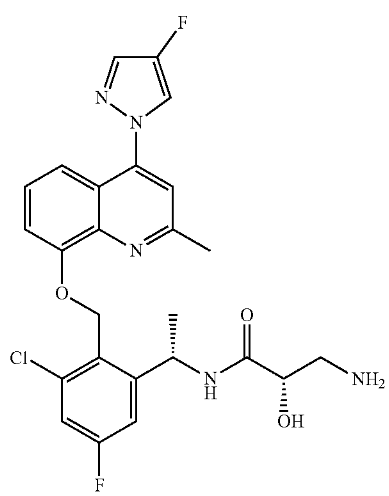 [SMILES: Cc1cc(-n2cc(F)cn2)c2cccc(OCc3c(Cl)cc(F)cc3[C@H](C)NC(=O)[C@@H](O)CN)c2n1] | 516.5 |
| 22. | | 530.1 |
| 23. | | 516.1 |
| 24. | | 515.2 |

TABLE 1-continued

Example Compounds Nos. 12 to 213

| Cpd No. | Structure | Mass# |
|---|---|---|
| 25. | 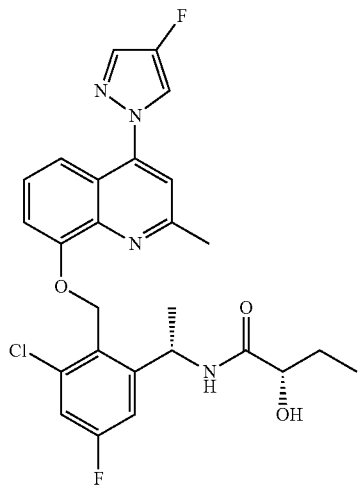 [SMILES: CC[C@H](O)C(=O)N[C@@H](C)c1cc(F)cc(Cl)c1COc1cccc2c(-n3cc(F)cn3)cc(C)nc12] | 516.1 |
| 26. | 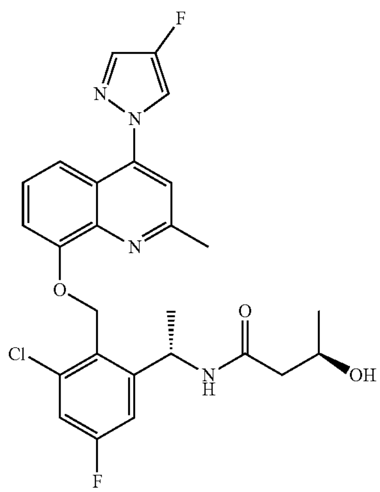 [SMILES: Cc1cc(-n2cc(F)cn2)c2cccc(OCc3c(Cl)cc(F)cc3[C@H](C)NC(=O)C[C@@H](C)O)c2n1] | 516.1 |
| 27. | 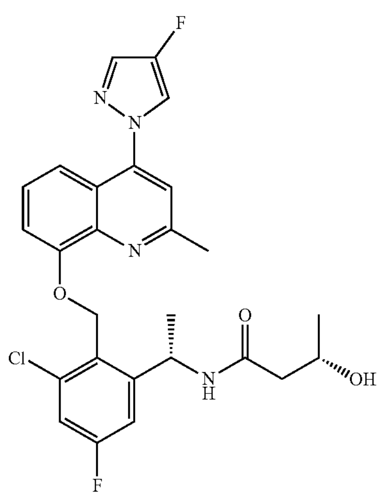 [SMILES: Cc1cc(-n2cc(F)cn2)c2cccc(OCc3c(Cl)cc(F)cc3[C@H](C)NC(=O)C[C@H](C)O)c2n1] | 516.1 |
| 28. | | 499.1 |
| 29. | | 498.6 |
| 30. | | 511.0 |

TABLE 1-continued

Example Compounds Nos. 12 to 213

| Cpd No. | Structure | Mass# |
|---|---|---|
| 31. | 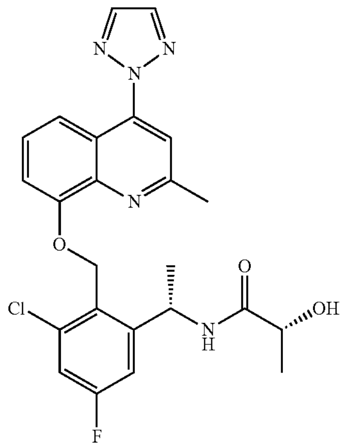 [SMILES: Cc1cc(-n2nccn2)c2cccc(OCc3c(Cl)cc(F)cc3[C@H](C)NC(=O)[C@@H](C)O)c2n1] | 485.0 |
| 32. | 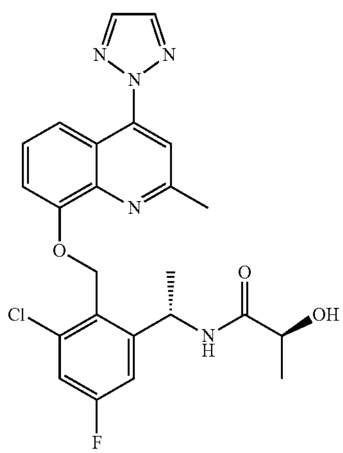 [SMILES: Cc1cc(-n2nccn2)c2cccc(OCc3c(Cl)cc(F)cc3[C@H](C)NC(=O)[C@H](C)O)c2n1] | 484.5 |
| 33. | 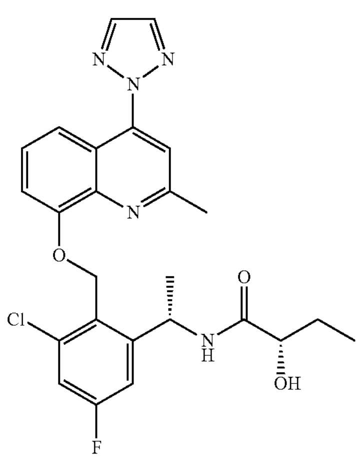 [SMILES: CC[C@H](O)C(=O)N[C@@H](C)c1cc(F)cc(Cl)c1COc1cccc2c(-n3nccn3)cc(C)nc12] | 499.1 |
| 34. | | 499.1 |
| 35. | | 537.5 |
| 36. | | 531.1 |

TABLE 1-continued

Example Compounds Nos. 12 to 213

| Cpd No. | Structure | Mass# |
|---|---|---|
| 37. | 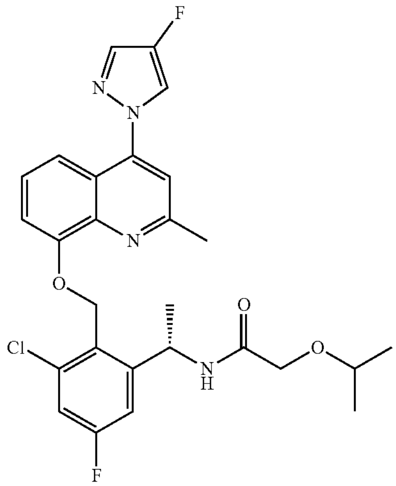 [SMILES: Cc1cc(-n2cc(F)cn2)c2cccc(OCc3c(Cl)cc(F)cc3[C@H](C)NC(=O)COC(C)C)c2n1] | 529.6 |
| 38. | 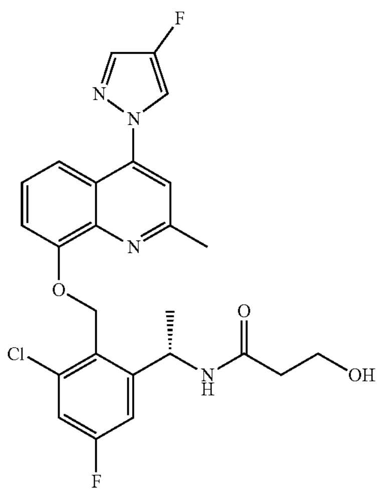 [SMILES: Cc1cc(-n2cc(F)cn2)c2cccc(OCc3c(Cl)cc(F)cc3[C@H](C)NC(=O)CCO)c2n1] | 501.5 |
| 39. | 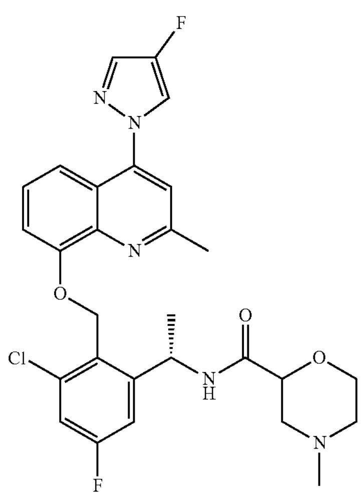 [SMILES: Cc1cc(-n2cc(F)cn2)c2cccc(OCc3c(Cl)cc(F)cc3[C@H](C)NC(=O)C3CN(C)CCO3)c2n1] | 556.3 |
| 40. | | 541.5 |
| 41. | | 510.2 |
| 42. | | 498.2 |

TABLE 1-continued

Example Compounds Nos. 12 to 213

| Cpd No. | Structure | Mass# |
|---|---|---|
| 43. | 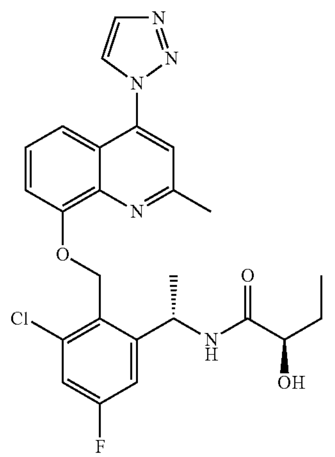 [SMILES: CC[C@@H](O)C(=O)N[C@@H](C)c1cc(F)cc(Cl)c1COc1cccc2c(-n3ccnn3)cc(C)nc12] | 498.2 |
| 44. | 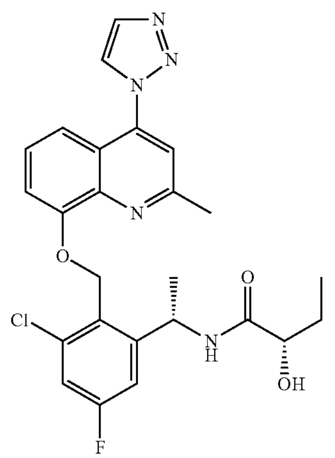 [SMILES: CC[C@H](O)C(=O)N[C@@H](C)c1cc(F)cc(Cl)c1COc1cccc2c(-n3ccnn3)cc(C)nc12] | 498.2 |
| 45. | 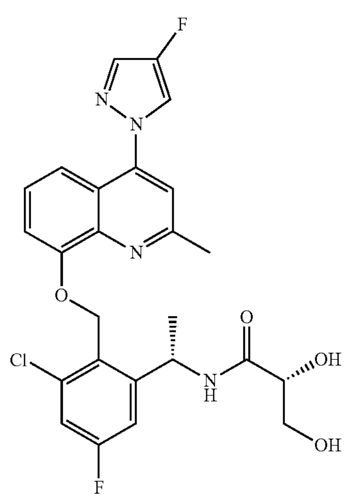 [SMILES: Cc1cc(-n2cc(F)cn2)c2cccc(OCc3c(Cl)cc(F)cc3[C@H](C)NC(=O)[C@H](O)CO)c2n1] | 517.1 |
| 46. | | 543.3 |
| 47. | | 543.3 |
| 48. | | 567.1 |

TABLE 1-continued
Example Compounds Nos. 12 to 213
| Cpd No. | Structure | Mass# |
|---|---|---|
| 49. | 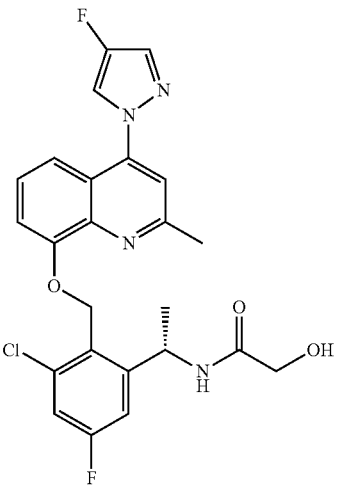 | 487.1 |
| 50. | 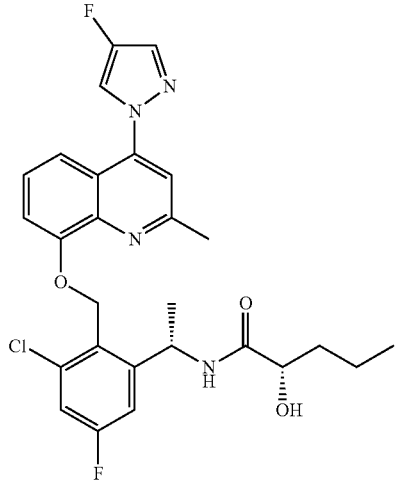 [SMILES: CCC[C@H](O)C(=O)N[C@@H](C)c1cc(F)cc(Cl)c1COc1cccc2c(-n3cc(F)cn3)cc(C)nc12] | 529.2 |
| 51. | 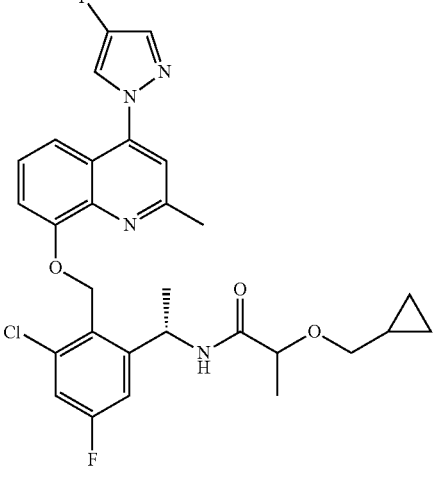 | 555.3 |
| 52. | 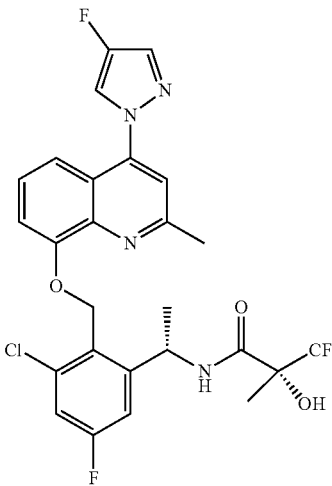 | 569.2 |
| 53. | 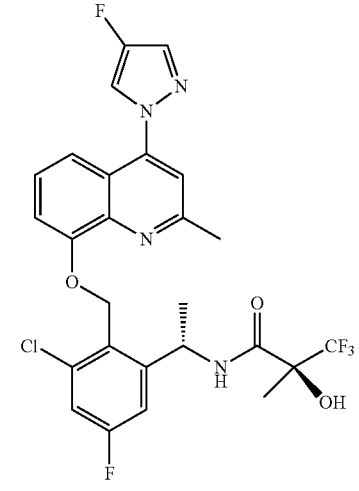 [SMILES: Cc1cc(-n2cc(F)cn2)c2cccc(OCc3c(Cl)cc(F)cc3[C@H](C)NC(=O)[C@](C)(O)C(F)(F)F)c2n1] | 569.1 |
| 54. | 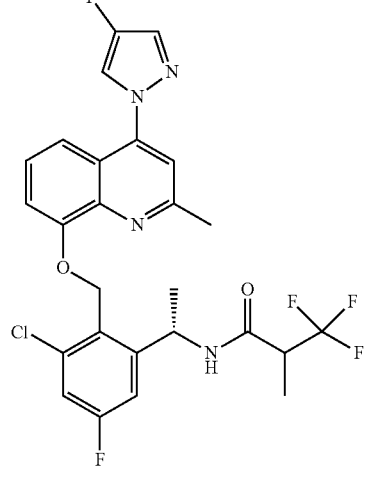 | 553.5 |

TABLE 1-continued

Example Compounds Nos. 12 to 213

| Cpd No. | Structure | Mass# |
|---|---|---|
| 55. | 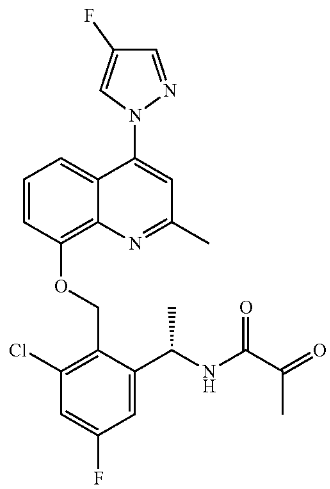 [SMILES: CC(=O)C(=O)N[C@@H](C)c1cc(F)cc(Cl)c1COc1cccc2c(-n3cc(F)cn3)cc(C)nc12] | 499.1 |
| 56. | 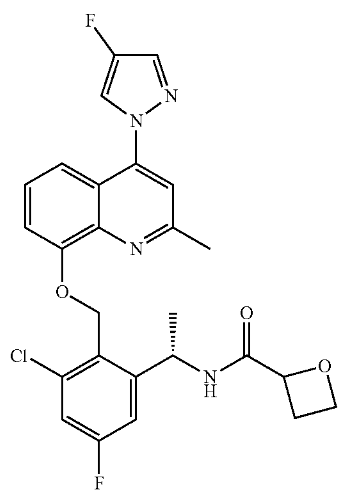 [SMILES: Cc1cc(-n2cc(F)cn2)c2cccc(OCc3c(Cl)cc(F)cc3[C@H](C)NC(=O)C3CCO3)c2n1] | 513.4 |
| 57. | 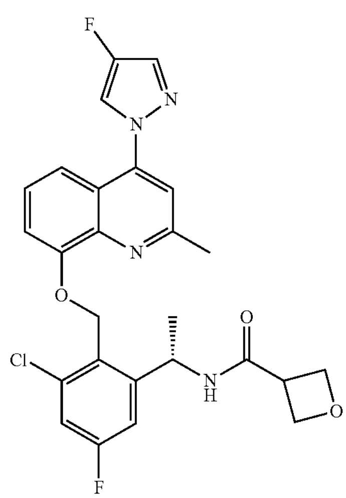 [SMILES: Cc1cc(-n2cc(F)cn2)c2cccc(OCc3c(Cl)cc(F)cc3[C@H](C)NC(=O)C3COC3)c2n1] | 513.4 |
| 58. | | 527.1 |
| 59. | | 515.2 |
| 60. | | 529.3 |

TABLE 1-continued
Example Compounds Nos. 12 to 213
| Cpd No. | Structure | Mass# |
|---|---|---|
| 61. | 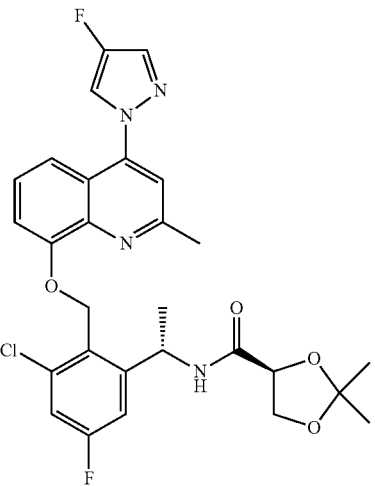 [SMILES: Cc1cc(-n2cc(F)cn2)c2cccc(OCc3c(Cl)cc(F)cc3[C@H](C)NC(=O)[C@@H]3COC(C)(C)O3)c2n1] | 557.5 |
| 62. | 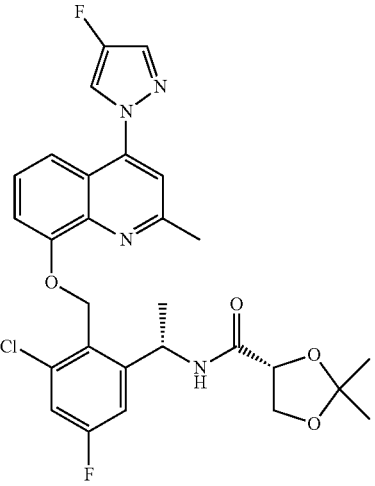 [SMILES: Cc1cc(-n2cc(F)cn2)c2cccc(OCc3c(Cl)cc(F)cc3[C@H](C)NC(=O)[C@H]3COC(C)(C)O3)c2n1] | 557.2 |
| 63. | 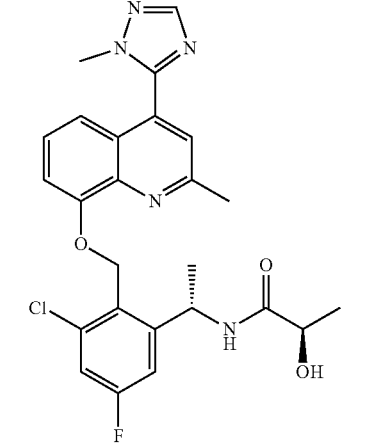 [SMILES: Cc1cc(-c2ncnn2C)c2cccc(OCc3c(Cl)cc(F)cc3[C@H](C)NC(=O)[C@@H](C)O)c2n1] | 498.2 |
| 64. | 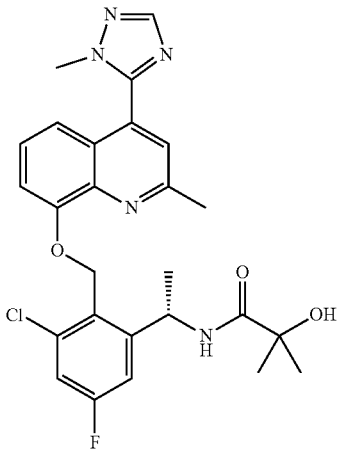 [SMILES: Cc1cc(-c2ncnn2C)c2cccc(OCc3c(Cl)cc(F)cc3[C@H](C)NC(=O)C(C)(C)O)c2n1] | 512.1 |
| 65. | 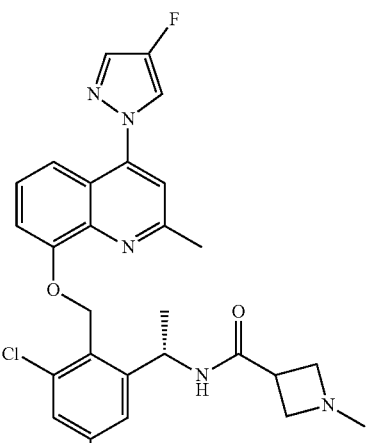 | 526.1 |
| 66. | 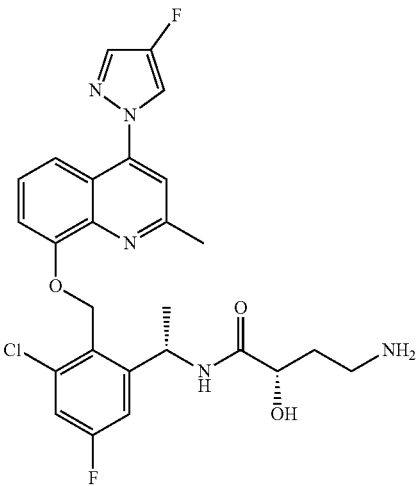 [SMILES: Cc1cc(-n2cc(F)cn2)c2cccc(OCc3c(Cl)cc(F)cc3[C@H](C)NC(=O)[C@@H](O)CCN)c2n1] | 530.3 |

TABLE 1-continued

Example Compounds Nos. 12 to 213

| Cpd No. | Structure | Mass# |
|---|---|---|
| 67. | 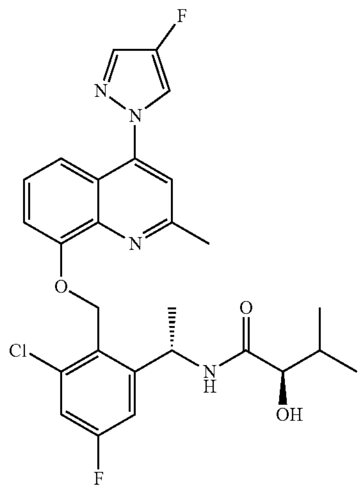 [SMILES: Cc1cc(-n2cc(F)cn2)c2cccc(OCc3c(Cl)cc(F)cc3[C@H](C)NC(=O)[C@H](O)C(C)C)c2n1] | 529.1 |
| 68. | 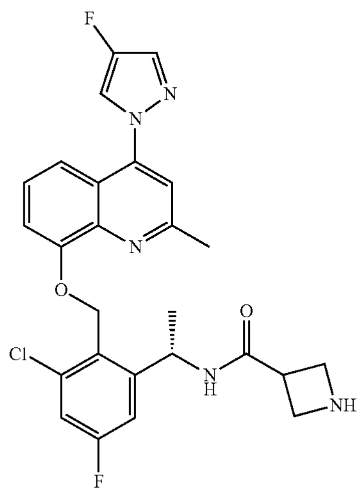 [SMILES: Cc1cc(-n2cc(F)cn2)c2cccc(OCc3c(Cl)cc(F)cc3[C@H](C)NC(=O)C3CNC3)c2n1] | 512.0 |
| 69. | 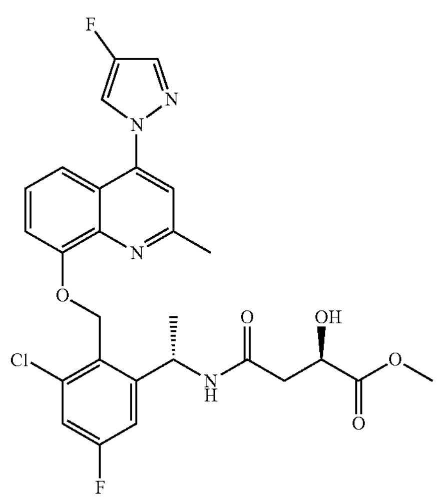 [SMILES: COC(=O)[C@H](O)CC(=O)N[C@@H](C)c1cc(F)cc(Cl)c1COc1cccc2c(-n3cc(F)cn3)cc(C)nc12] | 559.1 |
| 70. | | 559.1 |
| 71. | | 531.2 |
| 72. | | 558.4 |

TABLE 1-continued

Example Compounds Nos. 12 to 213

| Cpd No. | Structure | Mass# |
|---|---|---|
| 73. | 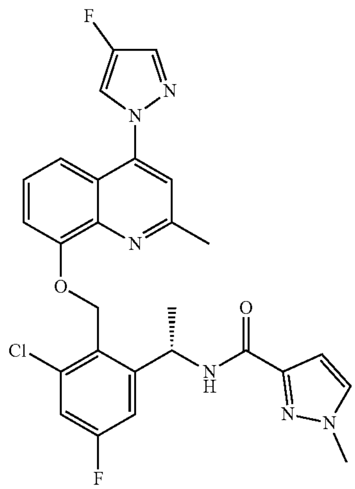 [SMILES: Cc1cc(-n2cc(F)cn2)c2cccc(OCc3c(Cl)cc(F)cc3[C@H](C)NC(=O)c3ccn(C)n3)c2n1] | 537.5 |
| 74. | 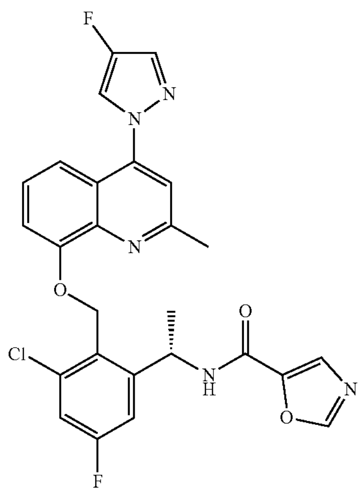 [SMILES: Cc1cc(-n2cc(F)cn2)c2cccc(OCc3c(Cl)cc(F)cc3[C@H](C)NC(=O)c3cnco3)c2n1] | 524.1 |
| 75. | 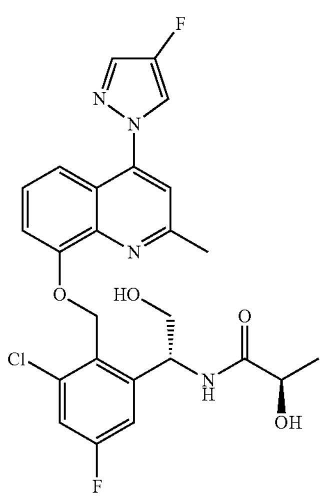 [SMILES: Cc1cc(-n2cc(F)cn2)c2cccc(OCc3c(Cl)cc(F)cc3[C@H](CO)NC(=O)[C@@H](C)O)c2n1] | 517.1 |
| 76. | | 544.1 |
| 77. | | 544.1 |
| 78. | | 524.1 |

TABLE 1-continued

Example Compounds Nos. 12 to 213

| Cpd No. | Structure | Mass# |
|---|---|---|
| 79. | 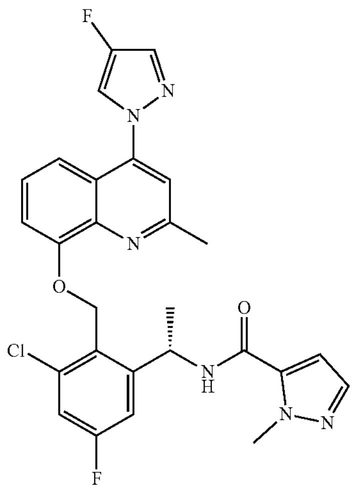 [SMILES: Cc1cc(-n2cc(F)cn2)c2cccc(OCc3c(Cl)cc(F)cc3[C@H](C)NC(=O)c3ccnn3C)c2n1] | 537.1 |
| 80. | 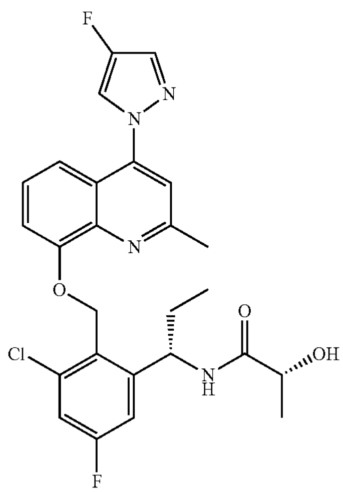 | 515.2 |
| 81. | 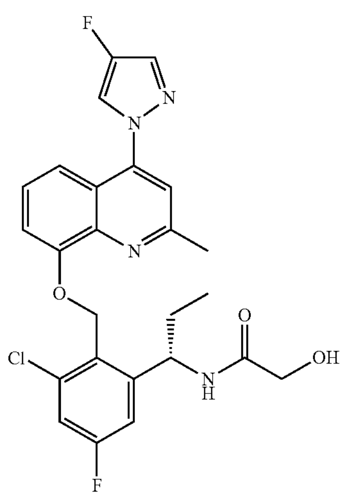 [SMILES: CC[C@H](NC(=O)CO)c1cc(F)cc(Cl)c1COc1cccc2c(-n3cc(F)cn3)cc(C)nc12] | 501.2 |
| 82. | | 524.1 |
| 83. | | 498.5 |
| 84. | | 512.4 |

TABLE 1-continued

Example Compounds Nos. 12 to 213

| Cpd No. | Structure | Mass# |
|---|---|---|
| 85. | 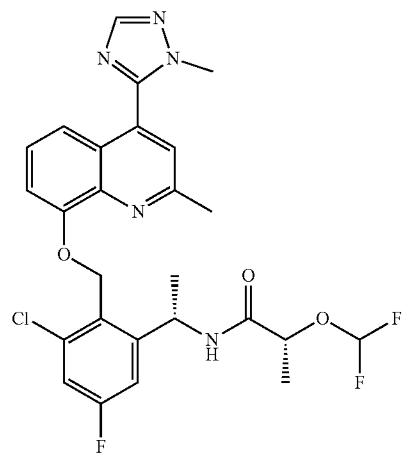 [SMILES: Cc1cc(-c2ncnn2C)c2cccc(OCc3c(Cl)cc(F)cc3[C@H](C)NC(=O)[C@@H](C)OC(F)F)c2n1] | 548.3 |
| 86. | 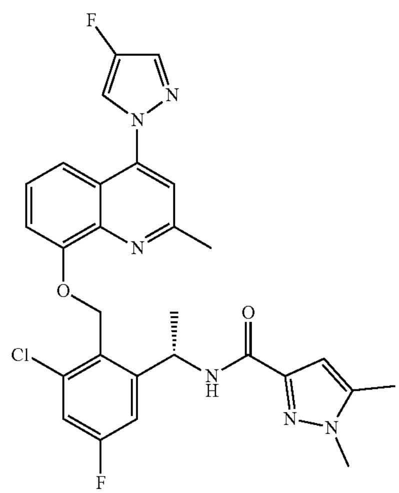 [SMILES: Cc1cc(-n2cc(F)cn2)c2cccc(OCc3c(Cl)cc(F)cc3[C@H](C)NC(=O)c3cc(C)n(C)n3)c2n1] | 551.2 |
| 87. | 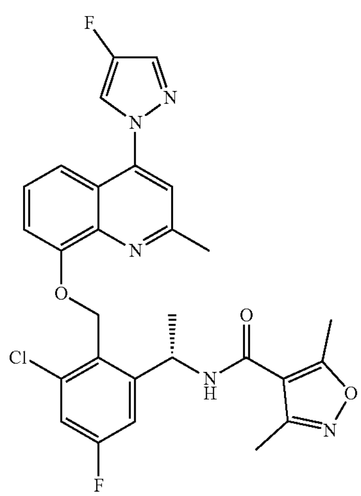 [SMILES: Cc1cc(-n2cc(F)cn2)c2cccc(OCc3c(Cl)cc(F)cc3[C@H](C)NC(=O)c3c(C)noc3C)c2n1] | 552.1 |
| 88. | | 538.1 |
| 89. | | 538.1 |
| 90. | | 540.1 |

TABLE 1-continued

Example Compounds Nos. 12 to 213

| Cpd No. | Structure | Mass# |
|---|---|---|
| 91. | 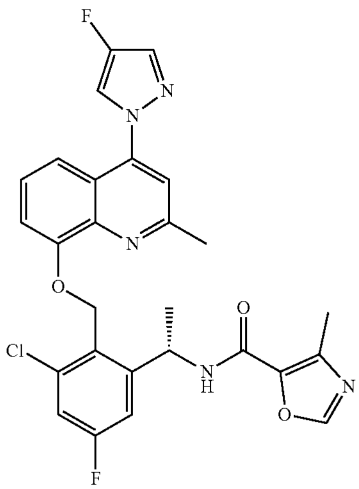 [SMILES: Cc1cc(-n2cc(F)cn2)c2cccc(OCc3c(Cl)cc(F)cc3[C@H](C)NC(=O)c3ocnc3C)c2n1] | 538.1 |
| 92. | 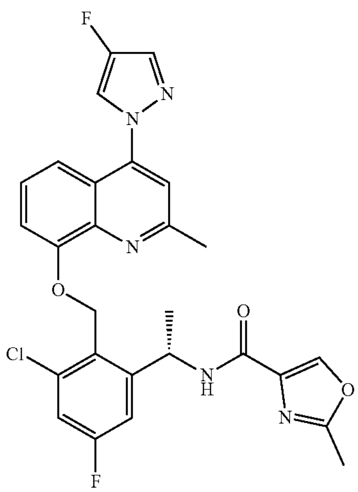 [SMILES: Cc1cc(-n2cc(F)cn2)c2cccc(OCc3c(Cl)cc(F)cc3[C@H](C)NC(=O)c3coc(C)n3)c2n1] | 538.5 |
| 93. | 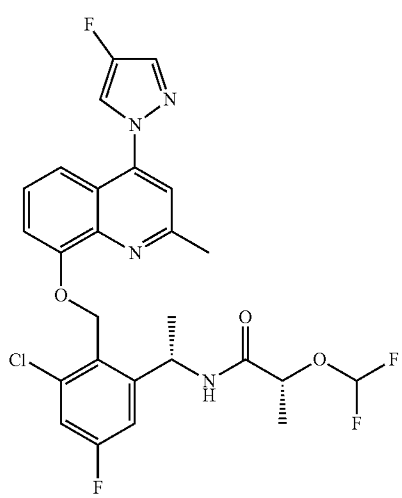 [SMILES: Cc1cc(-n2cc(F)cn2)c2cccc(OCc3c(Cl)cc(F)cc3[C@H](C)NC(=O)[C@@H](C)OC(F)F)c2n1] | 551.5 |
| 94. | | 625.0 |
| 95. | | 521.0 |
| 96. | | 521.4 |

TABLE 1-continued

Example Compounds Nos. 12 to 213

| Cpd No. | Structure | Mass# |
|---|---|---|
| 97. | 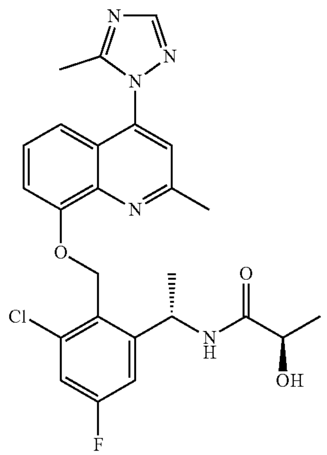 [SMILES: Cc1cc(-n2ncnc2C)c2cccc(OCc3c(Cl)cc(F)cc3[C@H](C)NC(=O)[C@@H](C)O)c2n1] | 498.3 |
| 98. | 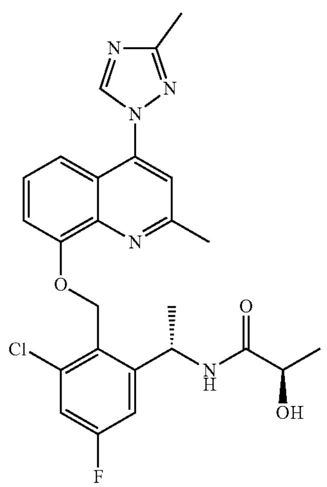 [SMILES: Cc1cc(-n2cnc(C)n2)c2cccc(OCc3c(Cl)cc(F)cc3[C@H](C)NC(=O)[C@@H](C)O)c2n1] | 498.4 |
| 99. | 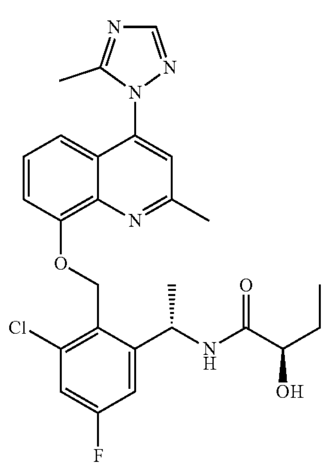 [SMILES: CC[C@@H](O)C(=O)N[C@@H](C)c1cc(F)cc(Cl)c1COc1cccc2c(-n3ncnc3C)cc(C)nc12] | 512.3 |
| 100. | | 512.4 |
| 101. | | 529.3 |
| 102. | | 501.1 |

TABLE 1-continued

Example Compounds Nos. 12 to 213

| Cpd No. | Structure | Mass# |
|---|---|---|
| 103. | 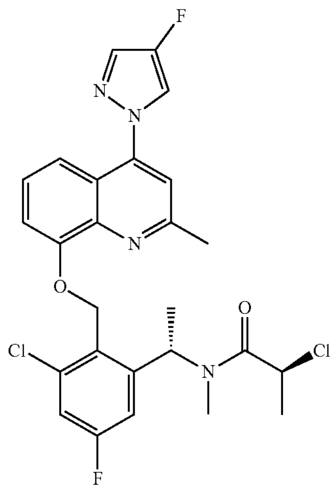 [SMILES: Cc1cc(-n2cc(F)cn2)c2cccc(OCc3c(Cl)cc(F)cc3[C@H](C)N(C)C(=O)[C@H](C)Cl)c2n1] | 533.1 |
| 104. | 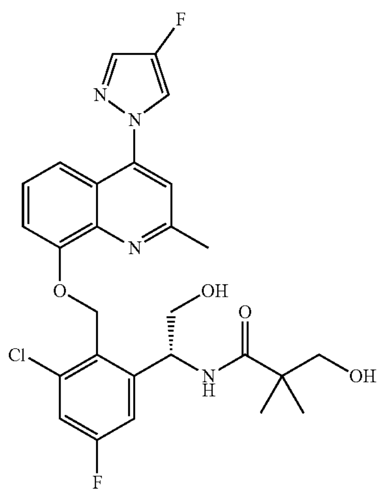 [SMILES: Cc1cc(-n2cc(F)cn2)c2cccc(OCc3c(Cl)cc(F)cc3[C@H](CO)NC(=O)C(C)(C)CO)c2n1] | 545.2 |
| 105. | 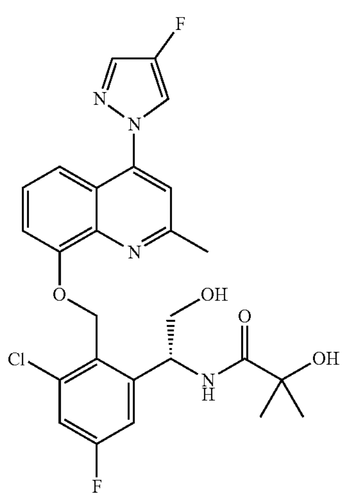 [SMILES: Cc1cc(-n2cc(F)cn2)c2cccc(OCc3c(Cl)cc(F)cc3[C@H](CO)NC(=O)C(C)(C)O)c2n1] | 531.1 |
| 106. | 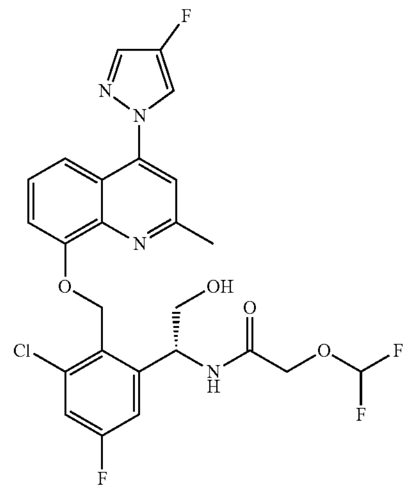 [SMILES: Cc1cc(-n2cc(F)cn2)c2cccc(OCc3c(Cl)cc(F)cc3[C@H](CO)NC(=O)COC(F)F)c2n1] | 553.1 |
| 107. | 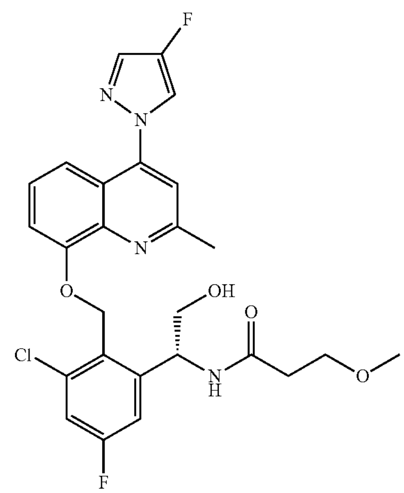 [SMILES: COCCC(=O)N[C@@H](CO)c1cc(F)cc(Cl)c1COc1cccc2c(-n3cc(F)cn3)cc(C)nc12] | 531.2 |
| 108. | 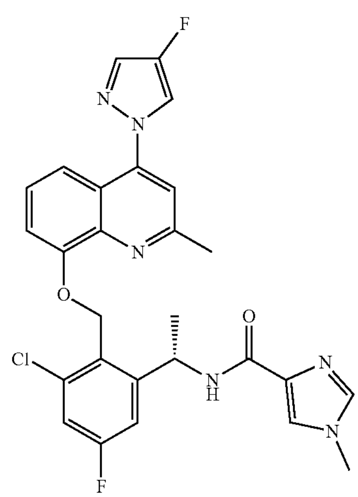 [SMILES: Cc1cc(-n2cc(F)cn2)c2cccc(OCc3c(Cl)cc(F)cc3[C@H](C)NC(=O)c3cn(C)cn3)c2n1] | 537.1 |

TABLE 1-continued

Example Compounds Nos. 12 to 213

| Cpd No. | Structure | Mass# |
|---|---|---|
| 109. | 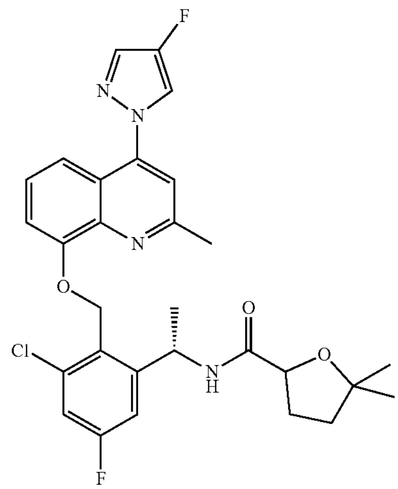 [SMILES: Cc1cc(-n2cc(F)cn2)c2cccc(OCc3c(Cl)cc(F)cc3[C@H](C)NC(=O)C3CCC(C)(C)O3)c2n1] | 555.2 |
| 110. | 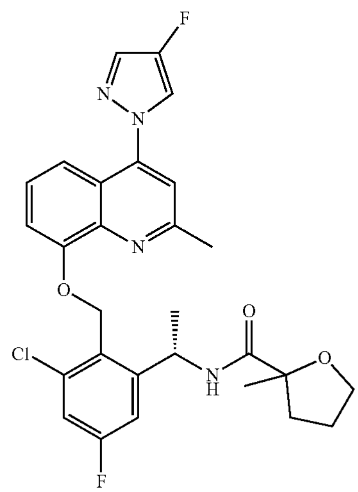 [SMILES: Cc1cc(-n2cc(F)cn2)c2cccc(OCc3c(Cl)cc(F)cc3[C@H](C)NC(=O)C3(C)CCCO3)c2n1] | 541.2 |
| 111. | 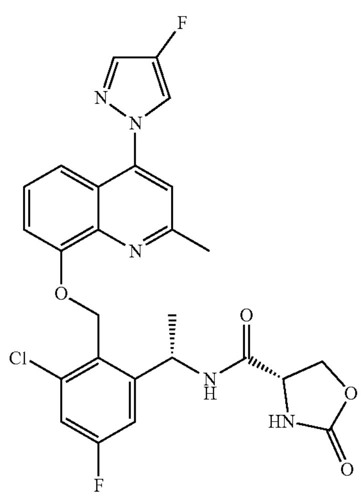 [SMILES: Cc1cc(-n2cc(F)cn2)c2cccc(OCc3c(Cl)cc(F)cc3[C@H](C)NC(=O)[C@@H]3COC(=O)N3)c2n1] | 542.2 |
| 112. | | 542.1 |
| 113. | | 541.2 |
| 114. | | 540.2 |

TABLE 1-continued

Example Compounds Nos. 12 to 213

| Cpd No. | Structure | Mass# |
|---|---|---|
| 115. | 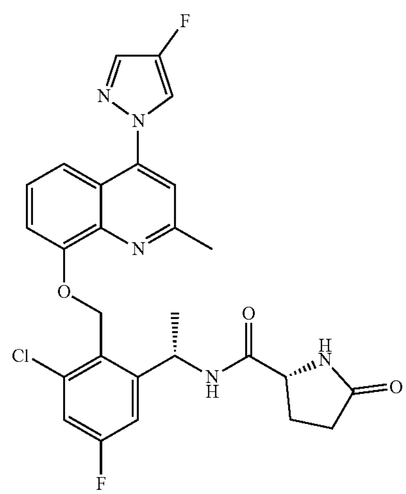 [SMILES: Cc1cc(-n2cc(F)cn2)c2cccc(OCc3c(Cl)cc(F)cc3[C@H](C)NC(=O)[C@H]3CCC(=O)N3)c2n1] | 540.2 |
| 116. | 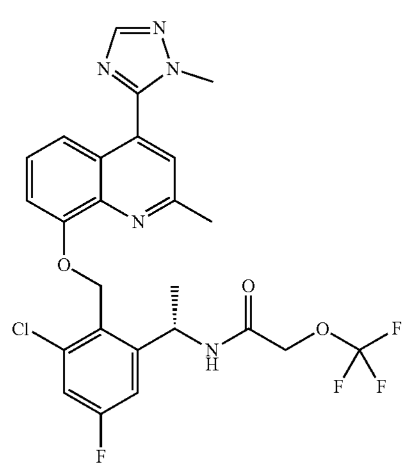 [SMILES: Cc1cc(-c2ncnn2C)c2cccc(OCc3c(Cl)cc(F)cc3[C@H](C)NC(=O)COC(F)(F)F)c2n1] | 552.0 |
| 117. | 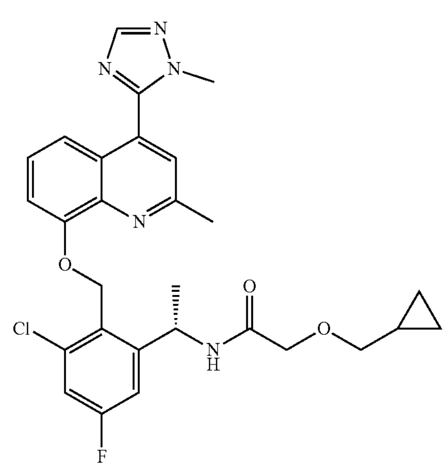 [SMILES: Cc1cc(-c2ncnn2C)c2cccc(OCc3c(Cl)cc(F)cc3[C@H](C)NC(=O)COCC3CC3)c2n1] | 538.3 |
| 118. | 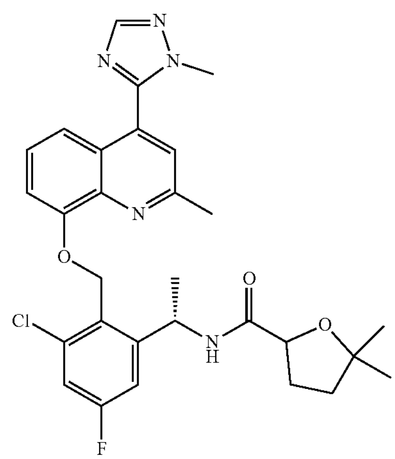 [SMILES: Cc1cc(-c2ncnn2C)c2cccc(OCc3c(Cl)cc(F)cc3[C@H](C)NC(=O)C3CCC(C)(C)O3)c2n1] | 552.4 |
| 119. | 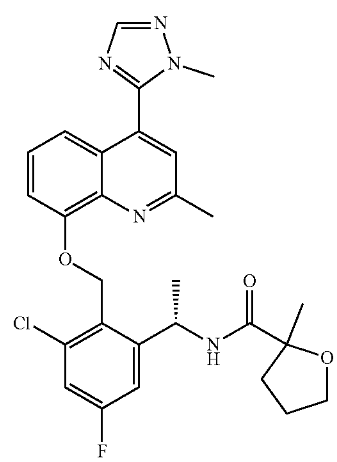 [SMILES: Cc1cc(-c2ncnn2C)c2cccc(OCc3c(Cl)cc(F)cc3[C@H](C)NC(=O)C3(C)CCCO3)c2n1] | 538.4 |
| 120. | 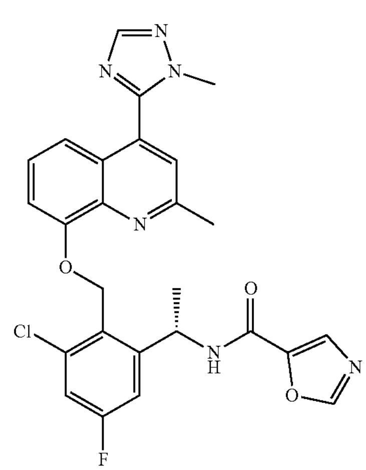 [SMILES: Cc1cc(-c2ncnn2C)c2cccc(OCc3c(Cl)cc(F)cc3[C@H](C)NC(=O)c3cnco3)c2n1] | 521.3 |

TABLE 1-continued

Example Compounds Nos. 12 to 213

| Cpd No. | Structure | Mass# |
|---|---|---|
| 121. | 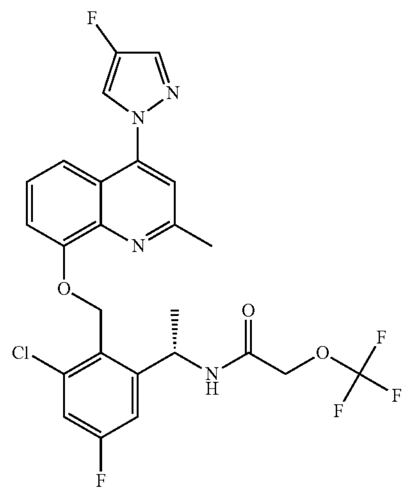 [SMILES: Cc1cc(-n2cc(F)cn2)c2cccc(OCc3c(Cl)cc(F)cc3[C@H](C)NC(=O)COC(F)(F)F)c2n1] | 555.1 |
| 122. | 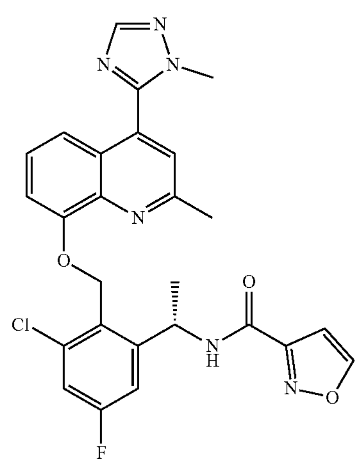 [SMILES: Cc1cc(-c2ncnn2C)c2cccc(OCc3c(Cl)cc(F)cc3[C@H](C)NC(=O)c3ccon3)c2n1] | 521.3 |
| 123. | 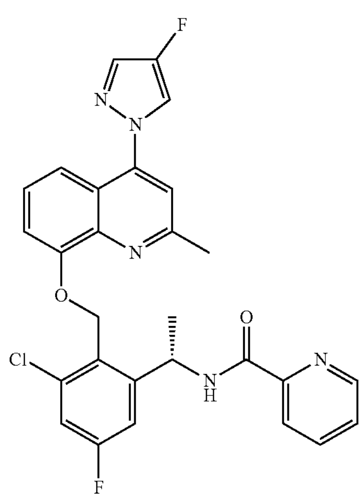 [SMILES: Cc1cc(-n2cc(F)cn2)c2cccc(OCc3c(Cl)cc(F)cc3[C@H](C)NC(=O)c3ccccn3)c2n1] | 534.4 |
| 124. | 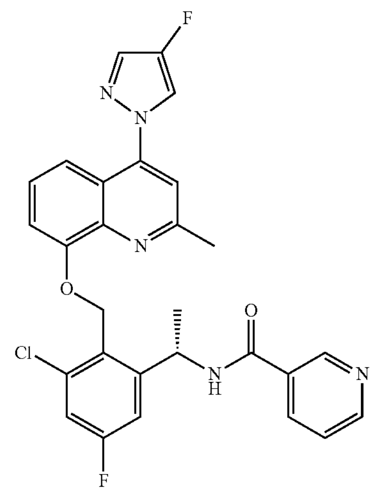 [SMILES: Cc1cc(-n2cc(F)cn2)c2cccc(OCc3c(Cl)cc(F)cc3[C@H](C)NC(=O)c3cccnc3)c2n1] | 534.4 |
| 125. | 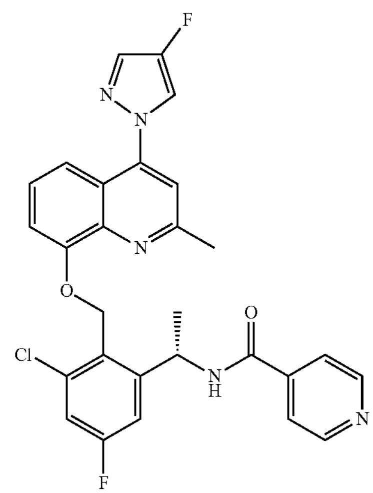 [SMILES: Cc1cc(-n2cc(F)cn2)c2cccc(OCc3c(Cl)cc(F)cc3[C@H](C)NC(=O)c3ccncc3)c2n1] | 534.4 |
| 126. | 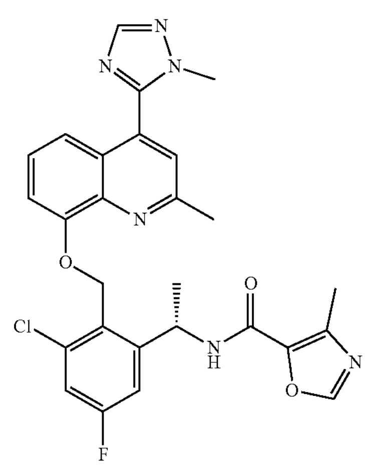 [SMILES: Cc1cc(-c2ncnn2C)c2cccc(OCc3c(Cl)cc(F)cc3[C@H](C)NC(=O)c3ocnc3C)c2n1] | 535.9 |

TABLE 1-continued

Example Compounds Nos. 12 to 213

| Cpd No. | Structure | Mass# |
|---|---|---|
| 127. | 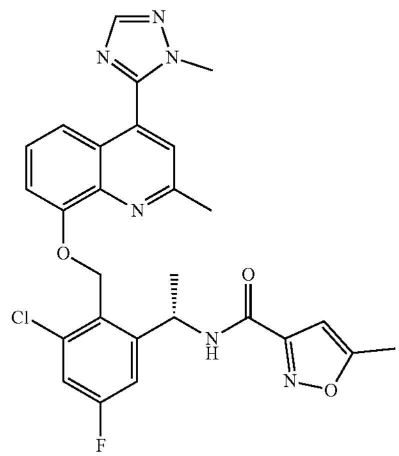 [SMILES: Cc1cc(-c2ncnn2C)c2cccc(OCc3c(Cl)cc(F)cc3[C@H](C)NC(=O)c3cc(C)on3)c2n1] | 535.8 |
| 128. | 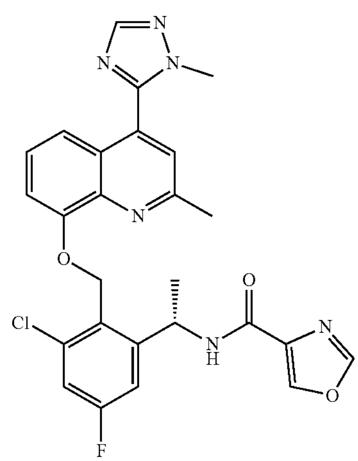 [SMILES: Cc1cc(-c2ncnn2C)c2cccc(OCc3c(Cl)cc(F)cc3[C@H](C)NC(=O)c3cocn3)c2n1] | 522.2 |
| 129. | 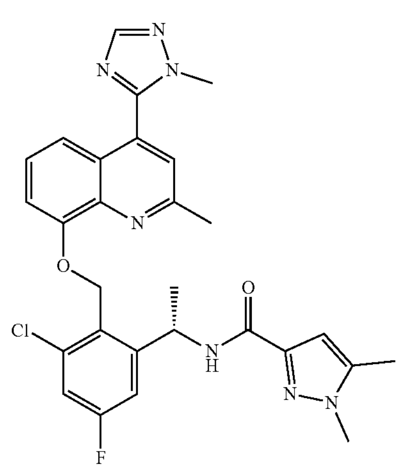 [SMILES: Cc1cc(-c2ncnn2C)c2cccc(OCc3c(Cl)cc(F)cc3[C@H](C)NC(=O)c3cc(C)n(C)n3)c2n1] | 549.3 |
| 130. | | 536.2 |
| 131. | | 549.2 |
| 132. | | 542.1 |

TABLE 1-continued
Example Compounds Nos. 12 to 213
| Cpd No. | Structure | Mass# |
|---|---|---|
| 133. | 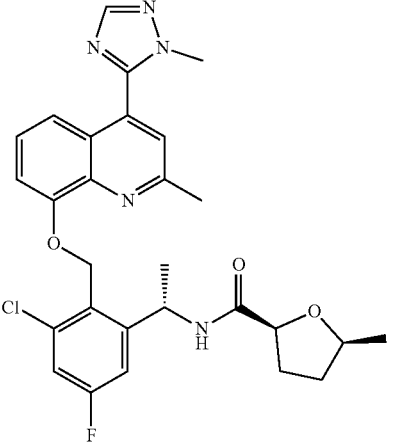 [SMILES: Cc1cc(-c2ncnn2C)c2cccc(OCc3c(Cl)cc(F)cc3[C@H](C)NC(=O)[C@@H]3CC[C@H](C)O3)c2n1] | 538.2 |
| 134. | 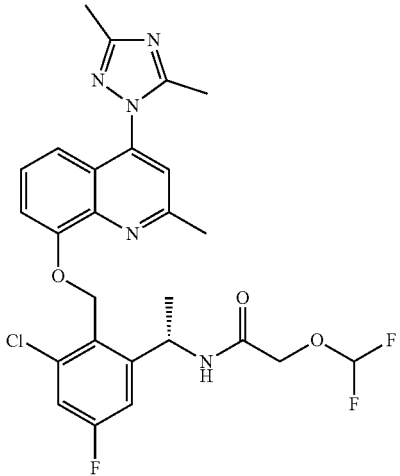 [SMILES: Cc1cc(-n2nc(C)nc2C)c2cccc(OCc3c(Cl)cc(F)cc3[C@H](C)NC(=O)COC(F)F)c2n1] | 549.3 |
| 135. | 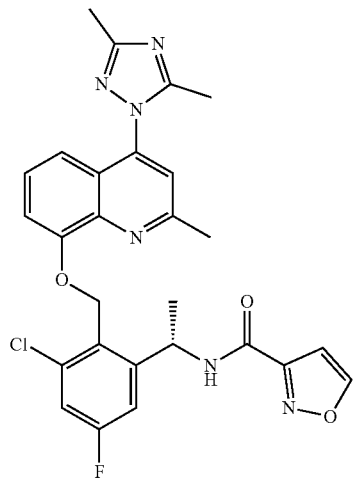 [SMILES: Cc1cc(-n2nc(C)nc2C)c2cccc(OCc3c(Cl)cc(F)cc3[C@H](C)NC(=O)c3ccon3)c2n1] | 536.2 |
| 136. | 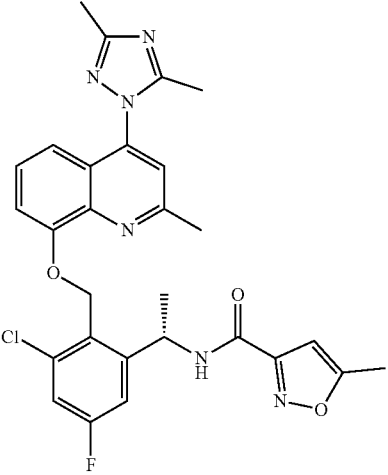 [SMILES: Cc1cc(-n2nc(C)nc2C)c2cccc(OCc3c(Cl)cc(F)cc3[C@H](C)NC(=O)c3cc(C)on3)c2n1] | 550.2 |
| 137. | 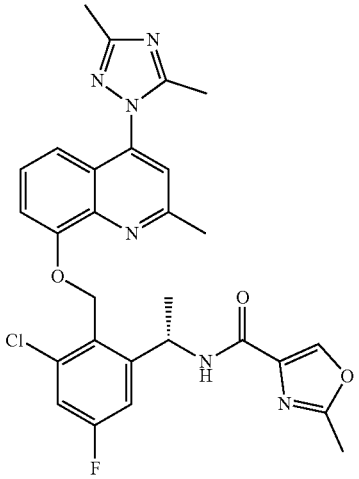 [SMILES: Cc1cc(-n2nc(C)nc2C)c2cccc(OCc3c(Cl)cc(F)cc3[C@H](C)NC(=O)c3coc(C)n3)c2n1] | 550.3 |
| 138. | 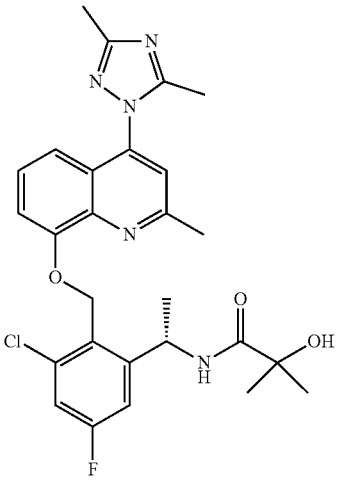 [SMILES: Cc1cc(-n2nc(C)nc2C)c2cccc(OCc3c(Cl)cc(F)cc3[C@H](C)NC(=O)C(C)(C)O)c2n1] | 527.4 |

TABLE 1-continued

Example Compounds Nos. 12 to 213

| Cpd No. | Structure | Mass# |
|---|---|---|
| 139. | 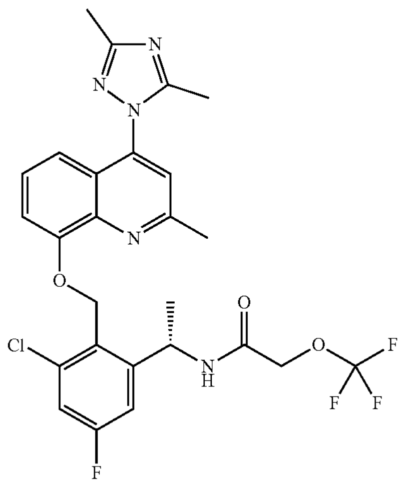 [SMILES: Cc1cc(-n2nc(C)nc2C)c2cccc(OCc3c(Cl)cc(F)cc3[C@H](C)NC(=O)COC(F)(F)F)c2n1] | 567.3 |
| 140. | 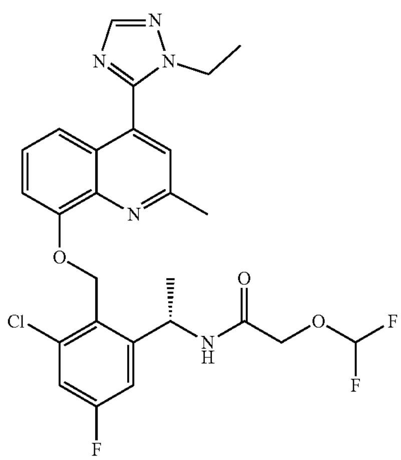 [SMILES: CCn1ncnc1-c1cc(C)nc2c(OCc3c(Cl)cc(F)cc3[C@H](C)NC(=O)COC(F)F)cccc12] | 548.9 |
| 141. | 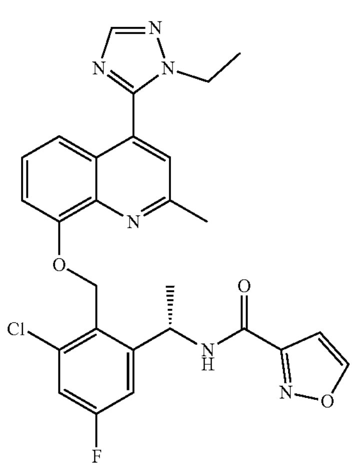 [SMILES: CCn1ncnc1-c1cc(C)nc2c(OCc3c(Cl)cc(F)cc3[C@H](C)NC(=O)c3ccon3)cccc12] | 536.0 |
| 142. | 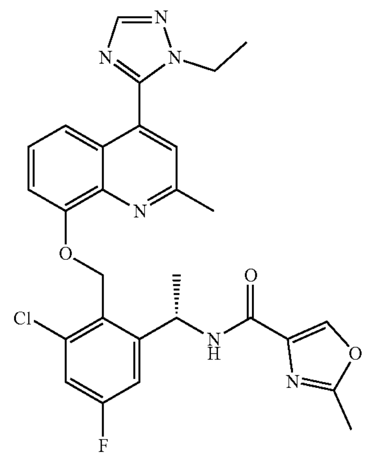 [SMILES: CCn1ncnc1-c1cc(C)nc2c(OCc3c(Cl)cc(F)cc3[C@H](C)NC(=O)c3coc(C)n3)cccc12] | 549.0 |
| 143. | 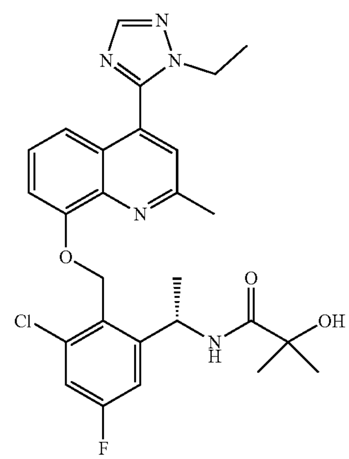 [SMILES: CCn1ncnc1-c1cc(C)nc2c(OCc3c(Cl)cc(F)cc3[C@H](C)NC(=O)C(C)(C)O)cccc12] | 527.0 |
| 144. | 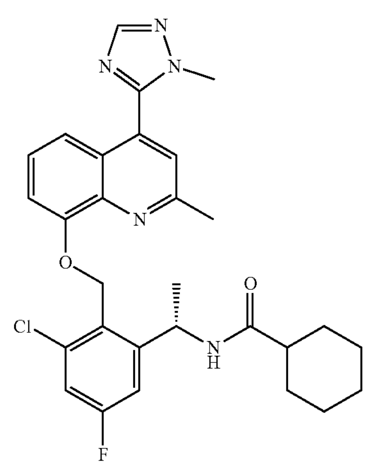 [SMILES: Cc1cc(-c2ncnn2C)c2cccc(OCc3c(Cl)cc(F)cc3[C@H](C)NC(=O)C3CCCCC3)c2n1] | 537.4 |

TABLE 1-continued

Example Compounds Nos. 12 to 213

| Cpd No. | Structure | Mass# |
|---|---|---|
| 145. | 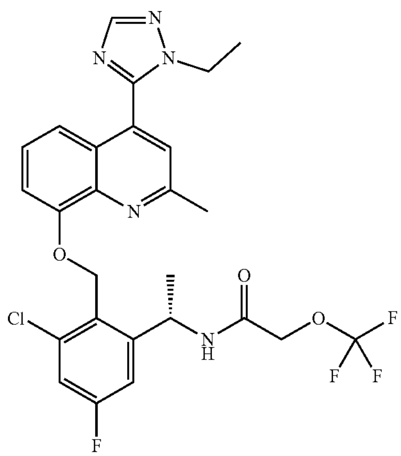 [SMILES: CCn1ncnc1-c1cc(C)nc2c(OCc3c(Cl)cc(F)cc3[C@H](C)NC(=O)COC(F)(F)F)cccc12] | 566.8 |
| 146. | 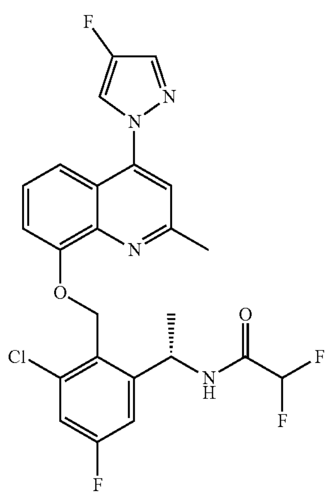 [SMILES: Cc1cc(-n2cc(F)cn2)c2cccc(OCc3c(Cl)cc(F)cc3[C@H](C)NC(=O)C(F)F)c2n1] | 507.4 |
| 147. | 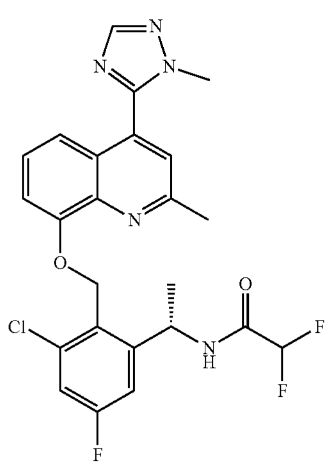 [SMILES: Cc1cc(-c2ncnn2C)c2cccc(OCc3c(Cl)cc(F)cc3[C@H](C)NC(=O)C(F)F)c2n1] | 504.4 |
| 148. | | 518.0 |
| 149. | | 549.5 |
| 150. | | 535.5 |

TABLE 1-continued

Example Compounds Nos. 12 to 213

| Cpd No. | Structure | Mass# |
|---|---|---|
| 151. | 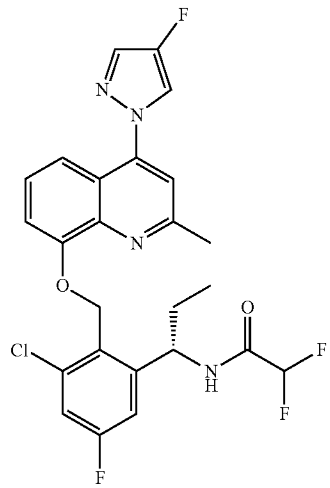 [SMILES: CC[C@H](NC(=O)C(F)F)c1cc(F)cc(Cl)c1COc1cccc2c(-n3cc(F)cn3)cc(C)nc12] | 521.1 |
| 152. | 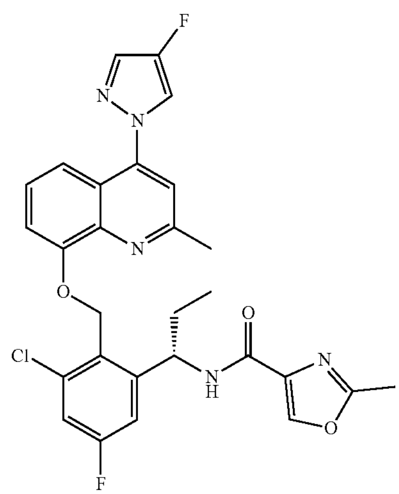 [SMILES: CC[C@H](NC(=O)c1coc(C)n1)c1cc(F)cc(Cl)c1COc1cccc2c(-n3cc(F)cn3)cc(C)nc12] | 552.4 |
| 153. | 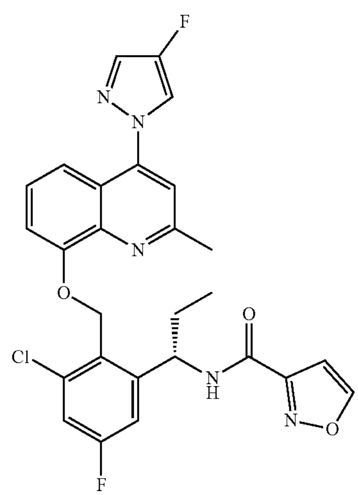 [SMILES: CC[C@H](NC(=O)c1ccon1)c1cc(F)cc(Cl)c1COc1cccc2c(-n3cc(F)cn3)cc(C)nc12] | 538.4 |
| 154. | | 551.4 |
| 155. | | 535.5 |
| 156. | | 535.9 |

TABLE 1-continued

Example Compounds Nos. 12 to 213

| Cpd No. | Structure | Mass# |
|---|---|---|
| 157. | 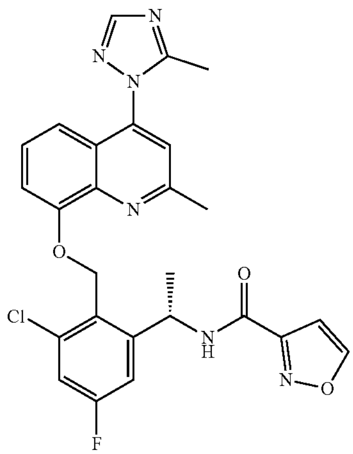 [SMILES: Cc1cc(-n2ncnc2C)c2cccc(OCc3c(Cl)cc(F)cc3[C@H](C)NC(=O)c3ccon3)c2n1] | 521.9 |
| 158. | 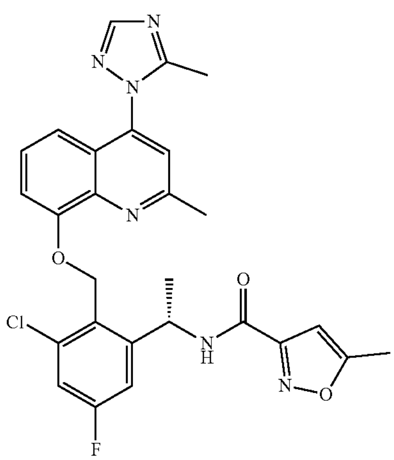 [SMILES: Cc1cc(-n2ncnc2C)c2cccc(OCc3c(Cl)cc(F)cc3[C@H](C)NC(=O)c3cc(C)on3)c2n1] | 535.9 |
| 159. | 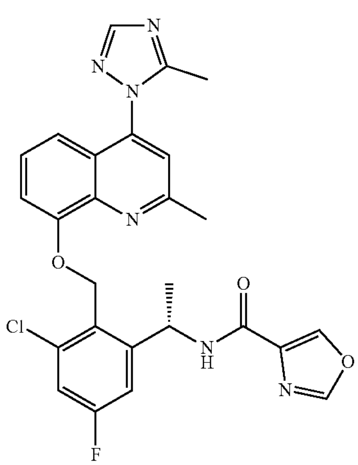 [SMILES: Cc1cc(-n2ncnc2C)c2cccc(OCc3c(Cl)cc(F)cc3[C@H](C)NC(=O)c3cocn3)c2n1] | 521.9 |
| 160. | 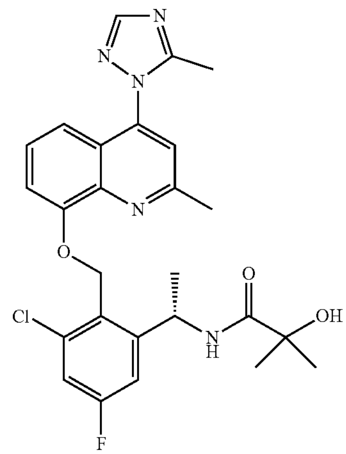 [SMILES: Cc1cc(-n2ncnc2C)c2cccc(OCc3c(Cl)cc(F)cc3[C@H](C)NC(=O)C(C)(C)O)c2n1] | 512.9 |
| 161. | 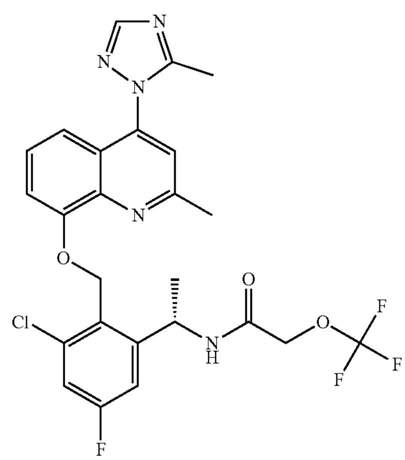 [SMILES: Cc1cc(-n2ncnc2C)c2cccc(OCc3c(Cl)cc(F)cc3[C@H](C)NC(=O)COC(F)(F)F)c2n1] | 553.2 |
| 162. | 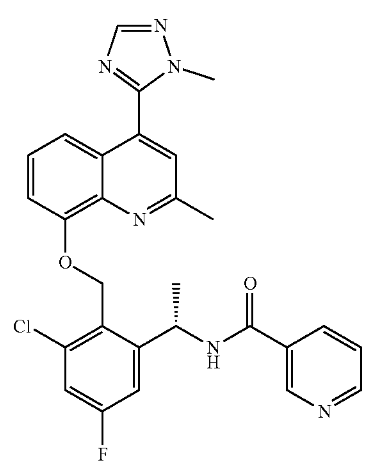 [SMILES: Cc1cc(-c2ncnn2C)c2cccc(OCc3c(Cl)cc(F)cc3[C@H](C)NC(=O)c3cccnc3)c2n1] | 531.0 |

TABLE 1-continued
Example Compounds Nos. 12 to 213
| Cpd No. | Structure | Mass# |
|---|---|---|
| 163. | 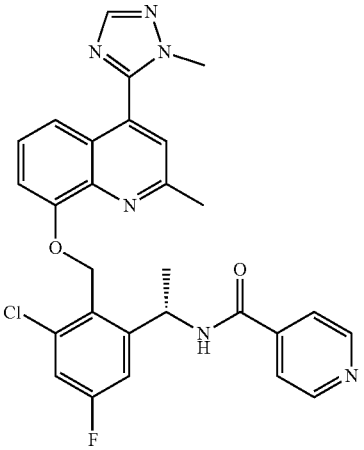 [SMILES: Cc1cc(-c2ncnn2C)c2cccc(OCc3c(Cl)cc(F)cc3[C@H](C)NC(=O)c3ccncc3)c2n1] | 531.0 |
| 164. | 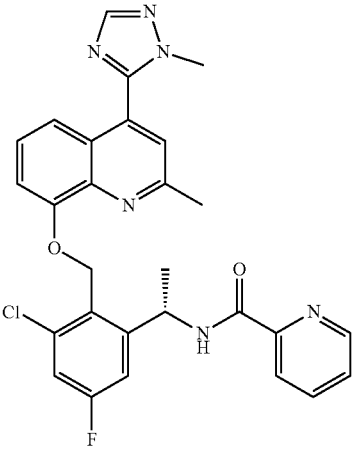 [SMILES: Cc1cc(-c2ncnn2C)c2cccc(OCc3c(Cl)cc(F)cc3[C@H](C)NC(=O)c3ccccn3)c2n1] | 531.0 |
| 165. | 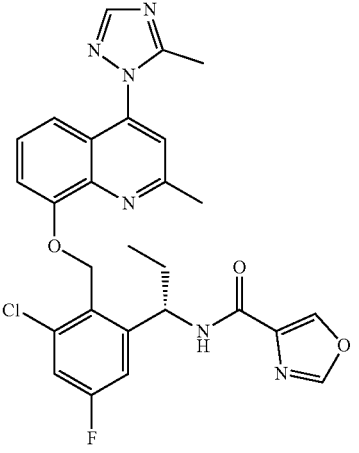 [SMILES: CC[C@H](NC(=O)c1cocn1)c1cc(F)cc(Cl)c1COc1cccc2c(-n3ncnc3C)cc(C)nc12] | 535.4 |
| 166. | 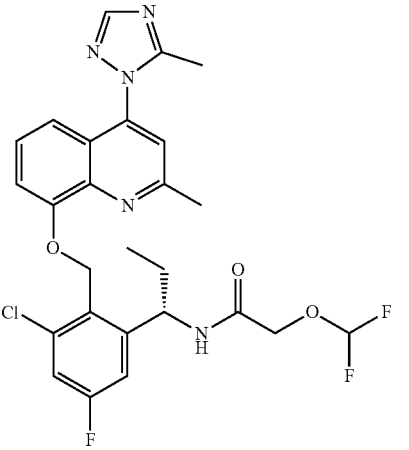 [SMILES: CC[C@H](NC(=O)COC(F)F)c1cc(F)cc(Cl)c1COc1cccc2c(-n3ncnc3C)cc(C)nc12] | 549.3 |
| 167. | 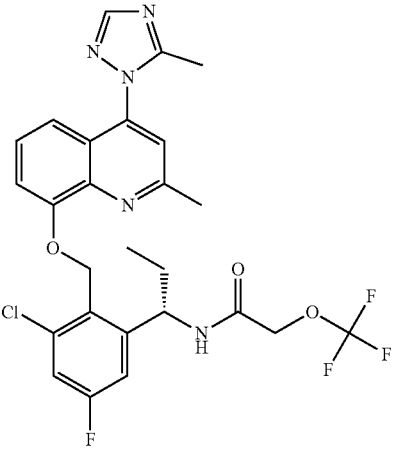 [SMILES: CC[C@H](NC(=O)COC(F)(F)F)c1cc(F)cc(Cl)c1COc1cccc2c(-n3ncnc3C)cc(C)nc12] | 566.9 |
| 168. | 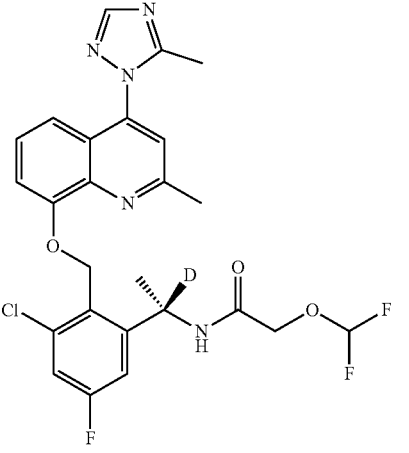 [SMILES: [2H][C@@](C)(NC(=O)COC(F)F)c1cc(F)cc(Cl)c1COc1cccc2c(-n3ncnc3C)cc(C)nc12] | 535.4 |

TABLE 1-continued

Example Compounds Nos. 12 to 213

| Cpd No. | Structure | Mass# |
|---|---|---|
| 169. | 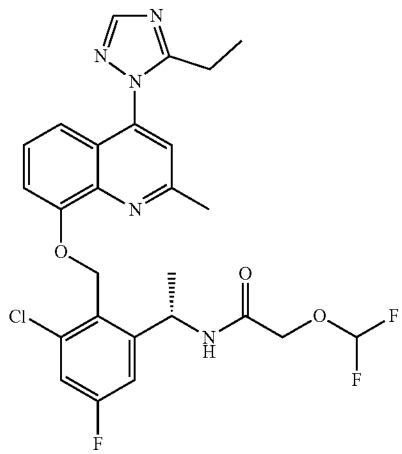 [SMILES: CCc1ncnn1-c1cc(C)nc2c(OCc3c(Cl)cc(F)cc3[C@H](C)NC(=O)COC(F)F)cccc12] | 549.2 |
| 170. | 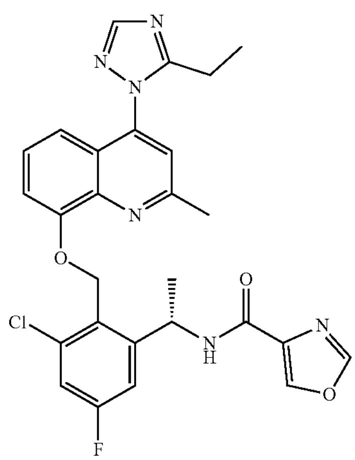 [SMILES: CCc1ncnn1-c1cc(C)nc2c(OCc3c(Cl)cc(F)cc3[C@H](C)NC(=O)c3cocn3)cccc12] | 536.2 |
| 171. | 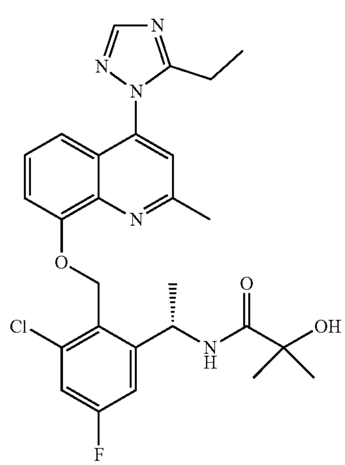 [SMILES: CCc1ncnn1-c1cc(C)nc2c(OCc3c(Cl)cc(F)cc3[C@H](C)NC(=O)C(C)(C)O)cccc12] | 527.2 |
| 172. | | 514.9 |
| 173. | | 518.1 |
| 174. | | 505.1 |

TABLE 1-continued
Example Compounds Nos. 12 to 213
| Cpd No. | Structure | Mass# |
|---|---|---|
| 175. | 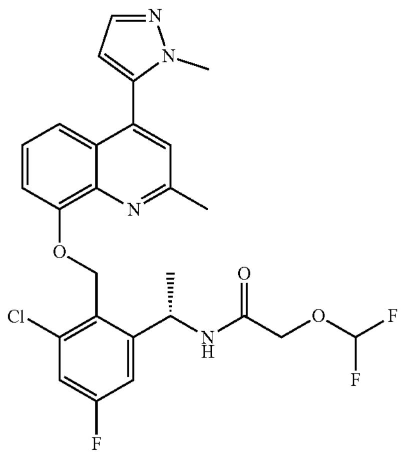 [SMILES: Cc1cc(-c2ccnn2C)c2cccc(OCc3c(Cl)cc(F)cc3[C@H](C)NC(=O)COC(F)F)c2n1] | 534.2 |
| 176. | 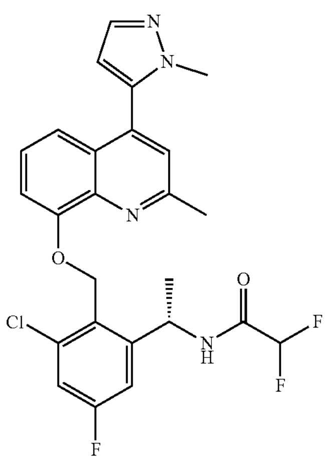 [SMILES: Cc1cc(-c2ccnn2C)c2cccc(OCc3c(Cl)cc(F)cc3[C@H](C)NC(=O)C(F)F)c2n1] | 503.8 |
| 177. | 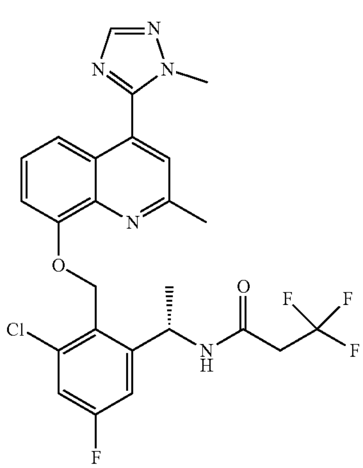 [SMILES: Cc1cc(-c2ncnn2C)c2cccc(OCc3c(Cl)cc(F)cc3[C@H](C)NC(=O)CC(F)(F)F)c2n1] | 536.1 |
| 178. | 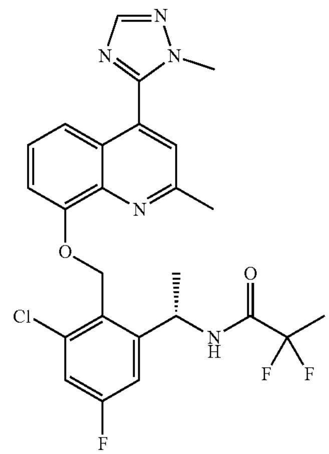 [SMILES: Cc1cc(-c2ncnn2C)c2cccc(OCc3c(Cl)cc(F)cc3[C@H](C)NC(=O)C(C)(F)F)c2n1] | 518.1 |
| 179. | 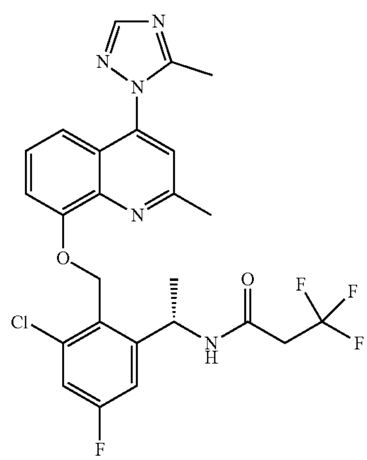 [SMILES: Cc1cc(-n2ncnc2C)c2cccc(OCc3c(Cl)cc(F)cc3[C@H](C)NC(=O)CC(F)(F)F)c2n1] | 536.1 |
| 180. | 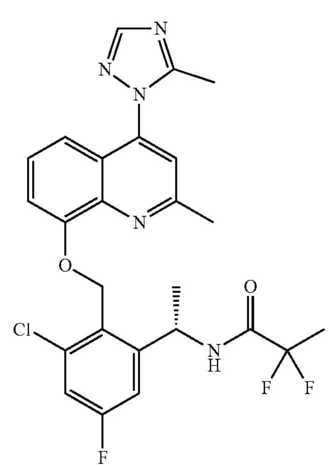 [SMILES: Cc1cc(-n2ncnc2C)c2cccc(OCc3c(Cl)cc(F)cc3[C@H](C)NC(=O)C(C)(F)F)c2n1] | 518.0 |
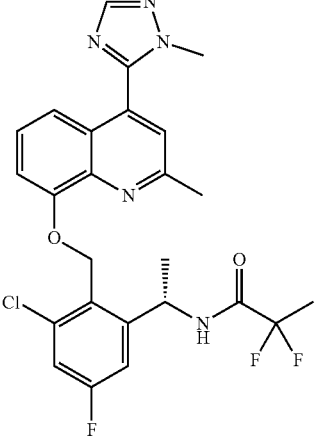

TABLE 1-continued

Example Compounds Nos. 12 to 213

| Cpd No. | Structure | Mass# |
|---|---|---|
| 181. | 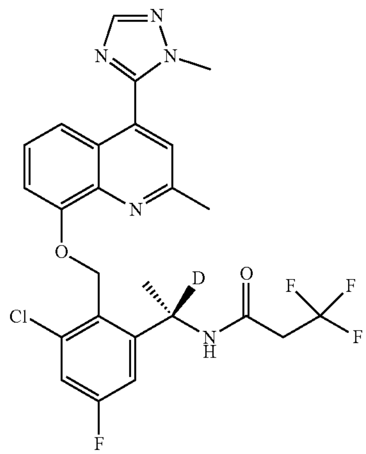 [SMILES: [2H][C@@](C)(NC(=O)CC(F)(F)F)c1cc(F)cc(Cl)c1COc1cccc2c(-c3ncnn3C)cc(C)nc12] | 537.8 |
| 182. | 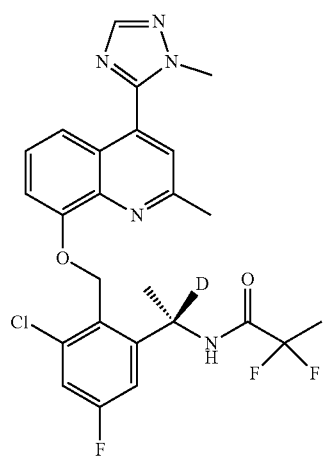 [SMILES: [2H][C@@](C)(NC(=O)C(C)(F)F)c1cc(F)cc(Cl)c1COc1cccc2c(-c3ncnn3C)cc(C)nc12] | 519.8 |
| 183. | 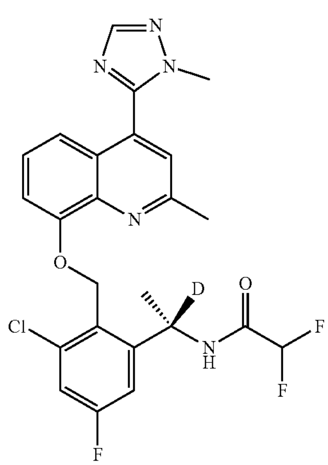 [SMILES: [2H][C@@](C)(NC(=O)C(F)F)c1cc(F)cc(Cl)c1COc1cccc2c(-c3ncnn3C)cc(C)nc12] | 505.8 |
| 184. | 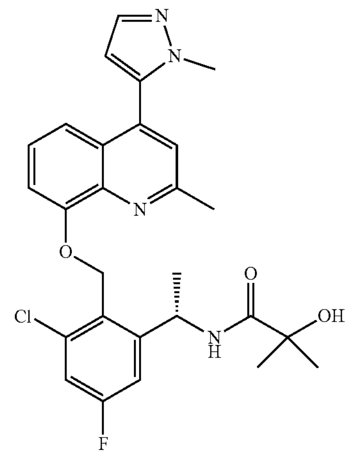 [SMILES: Cc1cc(-c2ccnn2C)c2cccc(OCc3c(Cl)cc(F)cc3[C@H](C)NC(=O)C(C)(C)O)c2n1] | 512.3 |
| 185. | 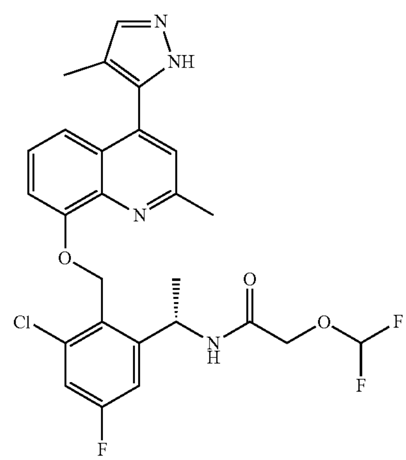 [SMILES: Cc1cc(-c2[nH]ncc2C)c2cccc(OCc3c(Cl)cc(F)cc3[C@H](C)NC(=O)COC(F)F)c2n1] | 533.9 |
| 186. | 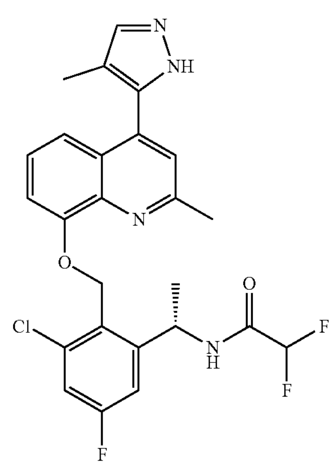 [SMILES: Cc1cc(-c2[nH]ncc2C)c2cccc(OCc3c(Cl)cc(F)cc3[C@H](C)NC(=O)C(F)F)c2n1] | 504.2 |

TABLE 1-continued

Example Compounds Nos. 12 to 213

| Cpd No. | Structure | Mass# |
|---|---|---|
| 187. | 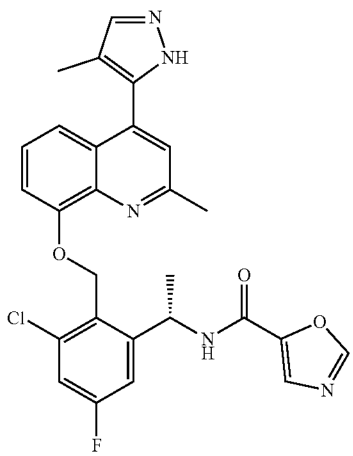 [SMILES: Cc1cc(-c2[nH]ncc2C)c2cccc(OCc3c(Cl)cc(F)cc3[C@H](C)NC(=O)c3cnco3)c2n1] | 520.8 |
| 188. | 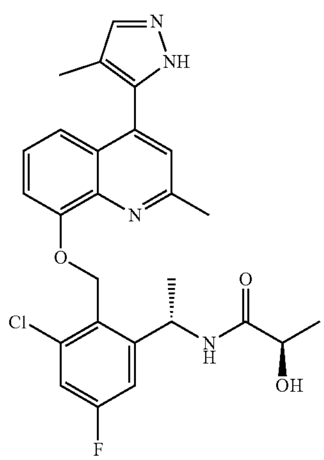 [SMILES: Cc1cc(-c2[nH]ncc2C)c2cccc(OCc3c(Cl)cc(F)cc3[C@H](C)NC(=O)[C@@H](C)O)c2n1] | 497.9 |
| 189. | 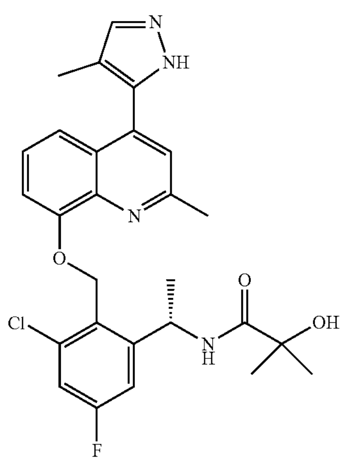 [SMILES: Cc1cc(-c2[nH]ncc2C)c2cccc(OCc3c(Cl)cc(F)cc3[C@H](C)NC(=O)C(C)(C)O)c2n1] | 511.9 |
| 190. | 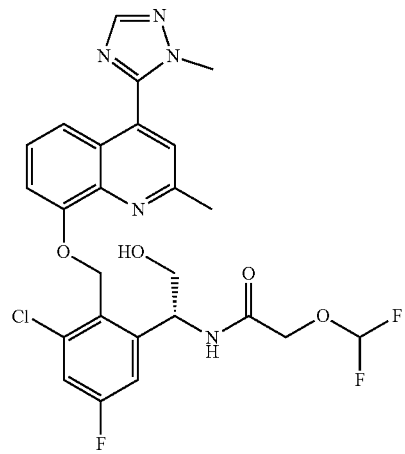 [SMILES: Cc1cc(-c2ncnn2C)c2cccc(OCc3c(Cl)cc(F)cc3[C@H](CO)NC(=O)COC(F)F)c2n1] | 549.9 |
| 191. | 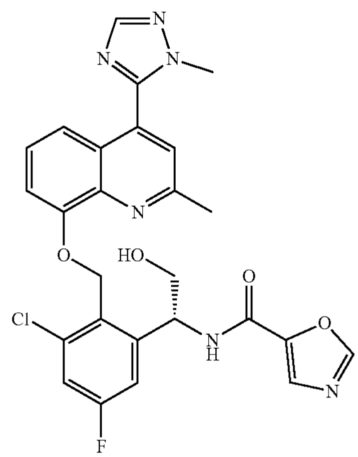 [SMILES: Cc1cc(-c2ncnn2C)c2cccc(OCc3c(Cl)cc(F)cc3[C@H](CO)NC(=O)c3cnco3)c2n1] | 537.1 |
| 192. | 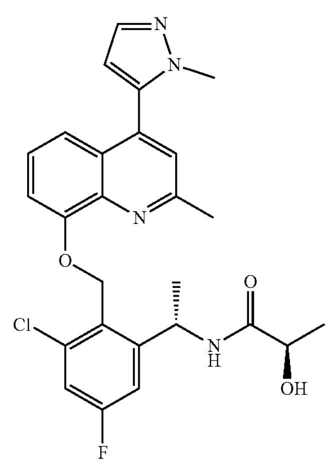 [SMILES: Cc1cc(-c2ccnn2C)c2cccc(OCc3c(Cl)cc(F)cc3[C@H](C)NC(=O)[C@@H](C)O)c2n1] | 497.9 |

TABLE 1-continued

Example Compounds Nos. 12 to 213

| Cpd No. | Structure | Mass# |
|---|---|---|
| 193. | 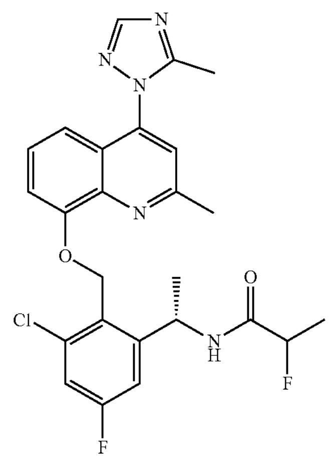 [SMILES: Cc1cc(-n2ncnc2C)c2cccc(OCc3c(Cl)cc(F)cc3[C@H](C)NC(=O)C(C)F)c2n1] | 500.0 |
| 194. | 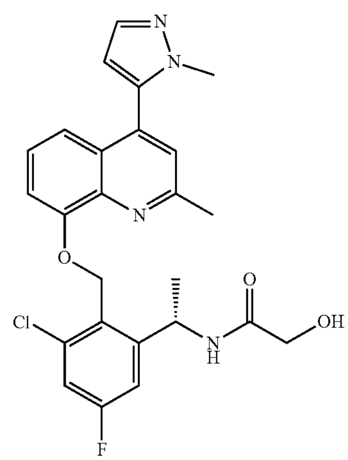 [SMILES: Cc1cc(-c2ccnn2C)c2cccc(OCc3c(Cl)cc(F)cc3[C@H](C)NC(=O)CO)c2n1] | 483.9 |
| 195. | 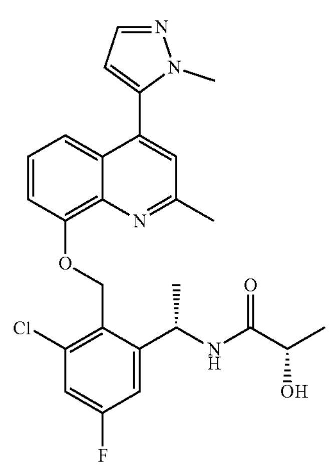 [SMILES: Cc1cc(-c2ccnn2C)c2cccc(OCc3c(Cl)cc(F)cc3[C@H](C)NC(=O)[C@H](C)O)c2n1] | 498.2 |
| 196. | 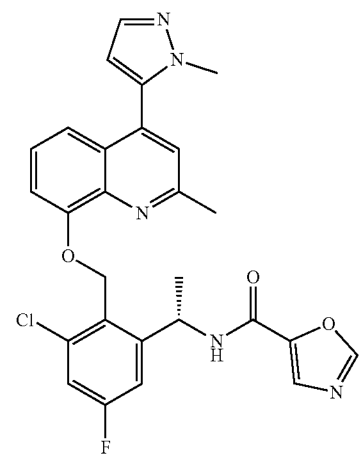 [SMILES: Cc1cc(-c2ccnn2C)c2cccc(OCc3c(Cl)cc(F)cc3[C@H](C)NC(=O)c3cnco3)c2n1] | 521.2 |
| 197. | 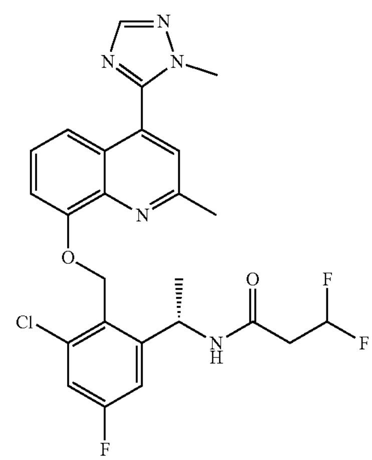 [SMILES: Cc1cc(-c2ncnn2C)c2cccc(OCc3c(Cl)cc(F)cc3[C@H](C)NC(=O)CC(F)F)c2n1] | 518.1 |
| 198. | 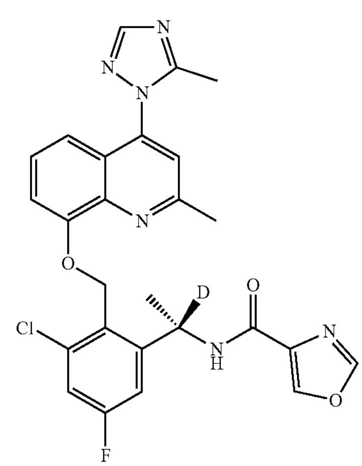 [SMILES: [2H][C@@](C)(NC(=O)c1cocn1)c1cc(F)cc(Cl)c1COc1cccc2c(-n3ncnc3C)cc(C)nc12] | 523.2 |

TABLE 1-continued

Example Compounds Nos. 12 to 213

| Cpd No. | Structure | Mass# |
|---|---|---|
| 199. | 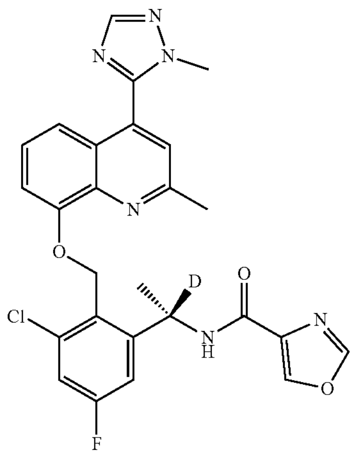 [SMILES: [2H][C@@](C)(NC(=O)c1cocn1)c1cc(F)cc(Cl)c1COc1cccc2c(-c3ncnn3C)cc(C)nc12] | 523.2 |
| 200. | 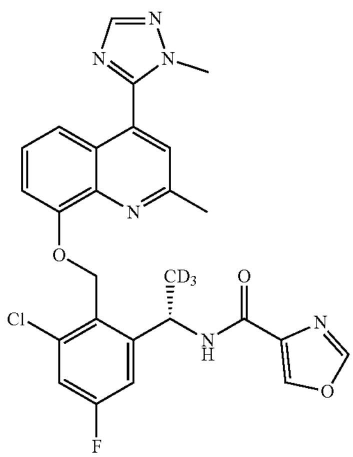 [SMILES: [2H]C([2H])([2H])[C@H](NC(=O)c1cocn1)c1cc(F)cc(Cl)c1COc1cccc2c(-c3ncnn3C)cc(C)nc12] | 525.1 |
| 201. | 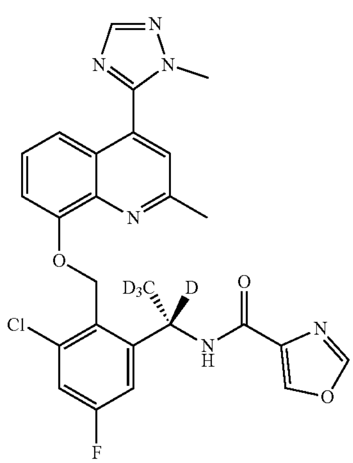 [SMILES: [2H]C([2H])([2H])[C@]([2H])(NC(=O)c1cocn1)c1cc(F)cc(Cl)c1COc1cccc2c(-c3ncnn3C)cc(C)nc12] | 526.2 |
| 202. | 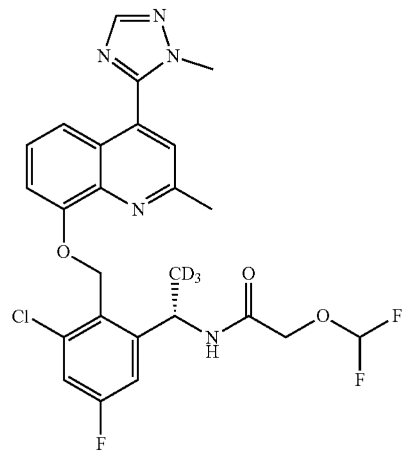 [SMILES: [2H]C([2H])([2H])[C@H](NC(=O)COC(F)F)c1cc(F)cc(Cl)c1COc1cccc2c(-c3ncnn3C)cc(C)nc12] | 538.0 |
| 203. | 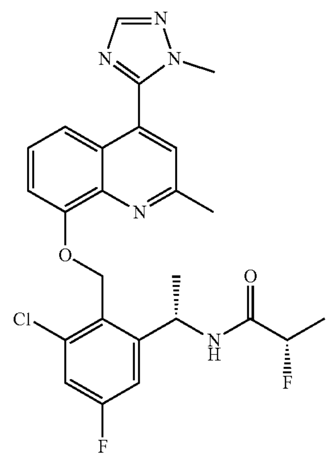 [SMILES: Cc1cc(-c2ncnn2C)c2cccc(OCc3c(Cl)cc(F)cc3[C@H](C)NC(=O)[C@H](C)F)c2n1] | 500.2 |
| 204. | 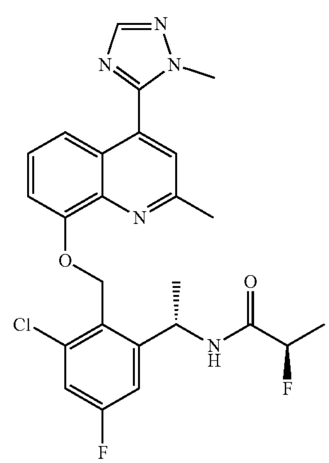 [SMILES: Cc1cc(-c2ncnn2C)c2cccc(OCc3c(Cl)cc(F)cc3[C@H](C)NC(=O)[C@@H](C)F)c2n1] | 500.3 |

TABLE 1-continued

Example Compounds Nos. 12 to 213

| Cpd No. | Structure | Mass# |
|---|---|---|
| 205. | 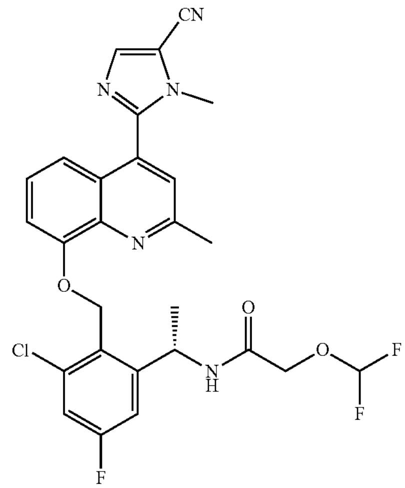 [SMILES: Cc1cc(-c2ncc(C#N)n2C)c2cccc(OCc3c(Cl)cc(F)cc3[C@H](C)NC(=O)COC(F)F)c2n1] | 559.2 |
| 206. | 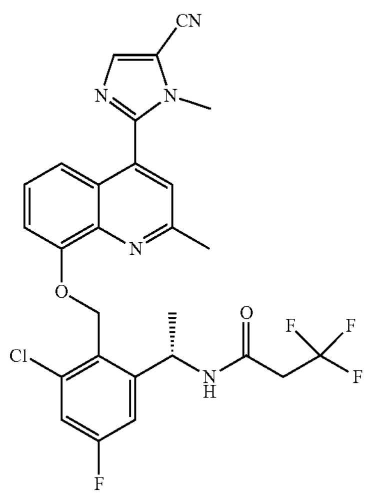 [SMILES: Cc1cc(-c2ncc(C#N)n2C)c2cccc(OCc3c(Cl)cc(F)cc3[C@H](C)NC(=O)CC(F)(F)F)c2n1] | 561.2 |
| 207. | 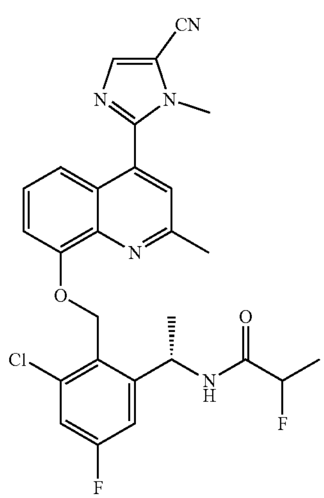 [SMILES: Cc1cc(-c2ncc(C#N)n2C)c2cccc(OCc3c(Cl)cc(F)cc3[C@H](C)NC(=O)C(C)F)c2n1] | 525.2 |
| 208. | 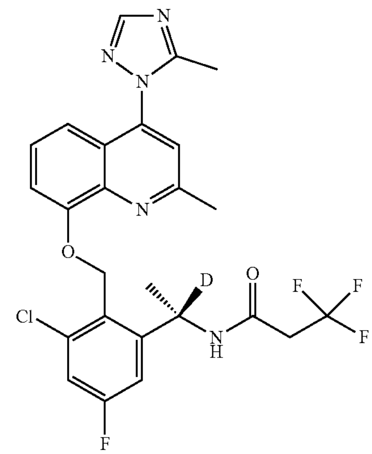 [SMILES: [2H][C@@](C)(NC(=O)CC(F)(F)F)c1cc(F)cc(Cl)c1COc1cccc2c(-n3ncnc3C)cc(C)nc12] | 538.1 |
| 209. | 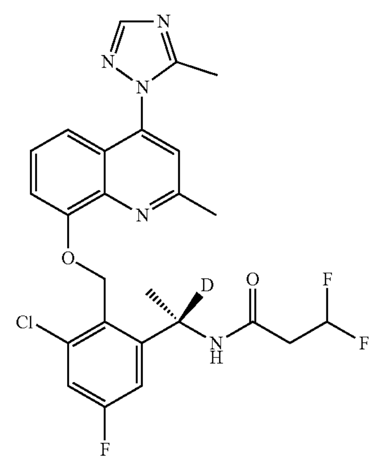 [SMILES: [2H][C@@](C)(NC(=O)CC(F)F)c1cc(F)cc(Cl)c1COc1cccc2c(-n3ncnc3C)cc(C)nc12] | 520.1 |
| 210. | 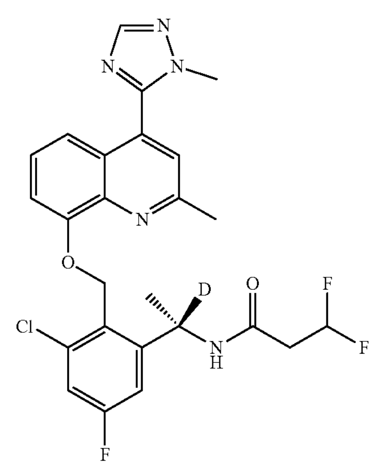 [SMILES: [2H][C@@](C)(NC(=O)CC(F)F)c1cc(F)cc(Cl)c1COc1cccc2c(-c3ncnn3C)cc(C)nc12] | 519.7 |

TABLE 1-continued

Example Compounds Nos. 12 to 213

| Cpd No. | Structure | Mass# |
|---|---|---|
| 211. | 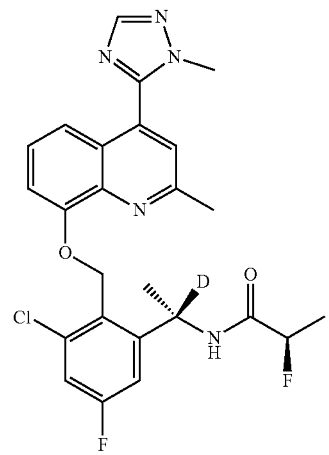 [SMILES: [2H][C@@](C)(NC(=O)[C@@H](C)F)c1cc(F)cc(Cl)c1COc1cccc2c(-c3ncnn3C)cc(C)nc12] | 501.2 |
| 212. | 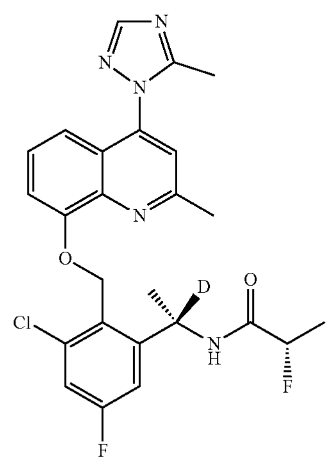 [SMILES: [2H][C@@](C)(NC(=O)[C@H](C)F)c1cc(F)cc(Cl)c1COc1cccc2c(-n3ncnc3C)cc(C)nc12] | 501.7 |
| 213. | 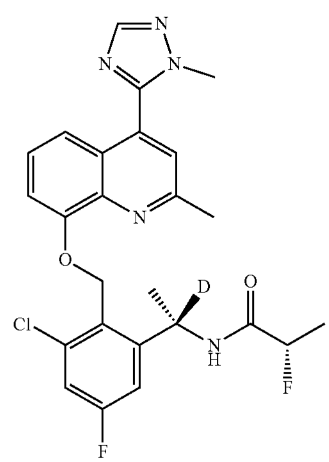 [SMILES: [2H][C@@](C)(NC(=O)[C@H](C)F)c1cc(F)cc(Cl)c1COc1cccc2c(-c3ncnn3C)cc(C)nc12] | 501.7 |

Mass: The mass spectrometry data (from liquid chromatography mass spectrometry spectra) are indicated (m/z) and represent the values for the protonated molecular ions [M + H⁺]

Example 12: Antagonistic Activity of Test Compounds Towards Human B2R

The following cell-based human bradykinin B2 receptor calcium mobilization (hB2R-CaM) assay was used to determine the antagonistic activity of compounds selected from the example compounds Nos. 1 to 168 towards human bradykinin B2 receptor (hB2R). The assay is defined herein as a standard in vitro B2 receptor activity assay, which can be used to determine $IC_{50}$ values of the compounds according to the present invention, e. g. the compounds shown in Examples 1-11.

The antagonistic activity of compounds according to the present invention was investigated with the hB2R-CaM assay using the B2 Bradykinin Receptor Stable Cell Line HTS041C (Eurofins, St. Charles Mo.) and the FLIPR Calcium 6 Assay Kit (Molecular Devices, Wokingham, UK) according to the instructions of the providers. CaM assay measurements were performed with a Flexstation 3 System (Molecular Devices) which allows the precise addition of compounds (B2R antagonists) and bradykinin (B2R agonist) to the cells and adjacent continuous recording of the time-dependent CaM assay signals.

Cell Culture, Plating and Starvation:

HTS041C cells were cultured in high glucose DMEM cell culture medium (Lonza) supplemented with 10% heat-inactivated FBS (PAN Biotech), 10 mM HEPES, Penicillin/Streptomycin (200 U/mL, 200 μg/mL), 1× non-essential amino acids (Lonza), and 250 μg/mL G418 (Invivogen) in cell incubator at 37° C. in a 5% $CO_2$ atmosphere.

One day before the CaM assay experiments cells were seeded in 200 μL DMEM cell culture medium with reduced FBS (5%) and without G418 on clear bottom black 96 well plates (ThermoFisher #165305). Cell starvation was carried out by incubation (37° C., 5% $CO_2$) of 70.000 cells/well for 24 h to 28 h. Immediately prior calcium dye-loading the medium was carefully aspirated and cells were washed with Hank's balanced salt solution (HBSS, Gibco) containing $Ca^{2+}$, $Mg^{2+}$ and 20 mM HEPES, adjusted to pH 7.4 (HBSS+).

Calcium Dye Loading of the Cells:

For calcium dye-loading one FLIPR 6 assay aliquot was dissolved in 20 mL HBSS+. 150 μL of the dye loading solution was added to cell plate and incubated for 120 min at 37° C. and 5% $CO_2$. After dye loading the cell plate was immediately transferred to the pre-warmed (37° C.) Flexstation 3 System for CaM assaying.

Intracellular Calcium Mobilization Assay (CaM Assay):

Freshly prepared compound (B2 receptor antagonists) dilution series (8 pt, n=2) and bradykinin (B2 receptor agonist) solution in non-binding plates (Costar) were transferred to the Flexstation System (source plate) shortly before starting the experiment. Bradykinin was added in EC80 concentration determined in n>3 preliminary experiments with 8 pt concentration response curves (n=8)). CaM assay was executed by Flexstation 3 System starting with recording of calcium-sensitive dye fluorescence in bottom-read Flex modus with ex/em=485 nm/525 nm, cut off(em)=515 nM. After 20 s, 50 μL of 4-fold concentrated compound dilutions were added to the cells resulting in a final DMSO (Sigma) concentration of 0.1% in the cell plate. CaM signals were monitored for 80 s after additions for detection of potential agonistic activities. Prior to bradykinin stimulus compound- and vehicle-treated cells were incubated for 25 min at 37° C. within the Flexstation System. Then 50 μL of a 5-fold concentrated bradykinin solution (HBSS+, 0.1% DMSO) was added to trigger CaM signals (Read out: Max-Min values) which were measured for 80 s post bradykinin stimulus.

IC50 determinations were performed by 4 parameter logistic model curve fitting of the 8 pt (n=2) compound concentration response curves using XLFIT (IDBS) software.

Measurement Results:

Example Compounds Nos. 2, 6, 9, 11, 11A, 11B, 11C, 12, 14, 15, 16, 17, 18, 19, 20, 26, 27, 29, 30, 56, 57, 58, 59, 60, 61, 63, 64, 70, 71, 82, 83, 84, 85, 90, 91, 92, 94, 95, 101, 102, 104, 106, 107, 110, 116, 117, 118, 120, 121, 122, 124, 126, 127, 128, 129, 130, 131, 132, 133, 134, 139, 140, 141, 142, 143, 144, 145, 147, 148, 149, 150, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 187, 188, 189, 190, 191, 192, 193, 194, 195, 196, 197, 198, 199, 200, 201, 202, 203, 204, 205, 206, 207, 208, 209, 210, 211, 212 and 213 showed an IC50-value of equal to or below 50 nM towards human bradykinin B2 receptor (hB2R).

Example Compounds Nos. 1, 8, 10, 22, 23, 24, 25, 28, 31, 32, 33, 34, 46, 48, 49, 50, 51, 54, 62, 66, 67, 68, 69, 86, 87, 88, 89, 93, 96, 97, 99, 103, 105, 108, 109, 111, 112, 113, 114, 115, 119, 123, 125, 135, 136, 137, 138, 146, 151, 152, 153 and 186 showed an $IC_{50}$-value between 51 and 250 nM towards human bradykinin B2 receptor (hB2R).

Example Compounds Nos. 3, 13, 21, 47, 52, 53, 55, 65, 72, 98 and 100 showed an $IC_{50}$-value between 251 nM and 1000 nM towards human bradykinin B2 receptor (hB2R).

None of the tested compounds showed any toxic effects in the cell-based test system.

Example 13: Determination of Biological Activity, Permeability and Metabolic Stability For a more detailed evaluation of their therapeutic potential, Example Compounds Nos. 1, 6, 11 and 13 according to the present invention were tested for their antagonistic activity towards hB2R, their permeability and their metabolic stability.

No structurally similar compounds have been disclosed in the prior art patent applications cited above or elsewhere. Prior art document WO 2008/116620 discloses heteroaryl-quinolin-8-yloxymethyl-pyridine compounds which can have similar substituents at the pyridine ring. However, WO 2008/116620 is completely silent about pharmacokinetic properties, e.g. permeability and metabolic stability, of its compounds. WO 2010/031589 discloses second-generation compounds developed on the basis of the WO 2008/116620 compounds, which demonstrated low metabolic stability, low bioavailability, formation of glutathione adducts and bioactivation (toxicity) as disclosed in WO 2014/159637.

In the absence of known structurally-related compounds and in order to demonstrate the advantageous effects of the novel structural elements of the invention, virtual comparative compounds containing elements suggested in WO 2008/116620 and WO 2010/031589, respectively, were evaluated in the same manner for their antagonistic activity towards hB2R, their permeability and their metabolic stability. As virtual comparative compounds, the Comparative Compounds Nos. 169, 170, 171, 172, 173 and 174 shown in Table 2 below, were used. The Comparative Compounds Nos. 169, 170, and 171 are based on structural elements suggested in WO 2008/116620. The Comparative Compounds Nos. 172, 173 and 174 virtually combine structural elements suggested in WO 2008/116620 with a structural modification of the pyridine ring moiety (replacement with a phenyl ring) as suggested in WO 2010/031589 and WO 2014/159637. In this connection, it has, however, to be noted that both, WO 2010/031589 and WO 2014/159637, fail to provide any teaching or suggestion for the claimed substituents in m-position to the chloro atom in the phenyl ring moiety. In fact, WO 2010/031589 and WO 2014/159637 are entirely silent about a fluoro substituent in m-position to the chloro atom in the phenyl ring moiety, and further suggest completely different substituents at the second position meta to the chloro atom in the phenyl ring.

A: Preparation of Comparative Compounds Nos. 169 to 174

The Comparative Example Compounds Nos. 169 to 174 shown in Table 2 below were prepared according to the methods described above and those disclosed in WO 2010/031589 and WO 2008/116620 with appropriate variations thereon as appreciated and known by those skilled in the art of synthetic organic chemistry to produce the compounds.

B: Antagonistic Activity of Test Compounds Towards hB2R

Relative $IC_{50}$ values of the test compounds were determined with the same hB2R-CaM assay as in Example 12. The results are shown in Table 2 below.

C: Permeability of Test Compounds

The permeability of the test compounds was determined with a Caco-2 cell permeability assay according to Hubatsch I. et al (*Nat. Protoc.* 2007, 2 (9), 2111-2119).

The Caco-2 cell line is a continuous cell of heterogeneous human epithelial colorectal adenocarcinoma cells. When cultured as a confluent monolayer on a permeable support such as a cell culture insert filter, the cells differentiate to form a polarized epithelial cell monolayer that provides a physical and biochemical barrier to the passage of ions and small molecules. In form of the confluent monolayer, the Caco-2 cells serve in the pharmaceutical industry as a well established in vitro model of the human small intestinal mucosa to predict the absorption of orally administered drugs. Assessing transport in both directions (apical to basolateral (A-B) and basolateral to apical (B-A)) across the cell monolayer enables an efflux ratio to be determined which provides an indicator as to whether a compound undergoes active efflux. When a compound has a higher efflux ratio, it indicates that the compound is more subject to active efflux. As will be appreciated, active efflux substantially compromises oral bioavailability.

The results of the determined efflux ratios are shown in Table 2 below.

D: Metabolic Stability of Test Compounds

Hepatic clearance is the most important drug elimination mechanism in the body and many marketed compounds are cleared by hepatic cytochrome P450-mediated metabolism. The excretion or elimination property of the test compounds was determined with a metabolic stability assay according to Obach R S (*Drug Metab. Dispos.* 1999, 27(11), 1350-1359).

Assays were performed in 96-deepwell-plates using liver microsomes pooled from male Wistar rats (Corning). Rat liver microsomal incubations were conducted in duplicate and incubation mixtures consisted of liver microsomes (0.5 mg microsomal protein/mL), test compound (1 μM), $MgCl_2$ (2 mM), and NADPH (1 mM) in a total volume of 0.7 ml sodium phosphate buffer (100 mM, pH 7.4). Reactions were commenced with the addition of NADPH and shaken on a horizontal shaker with a fitted heating block at 37° C. At t=0 min and the time points: 10 min, 30 min and 60 min; aliquots (70 μL) were removed from the incubations and added to 140 μl termination mixtures. Termination mixtures consisted of acetonitrile supplemented with diazepam, diclofenac and griseofulvin as internal analytical standards. The quenched samples were processed by mixing and centrifugation (2,200×g, 5 minutes). The particle free supernatant was diluted 1+1 with deionised water and subsequently subjected to LC-MS for quantitative bioanalysis in terms of test compound depletion (pump flow rate: 600 µL/min; Kinetex Phenyl-Hexyl analytical column 2.6 µm, 50×2.1 mm (Phenomenex, Germany)). Incubations containing verapamil at a concentration of 1 µM were used as high clearance positive control (PC; n=2), and incubations without NADPH (70 µl phosphate buffer (supplemented with 2 mM MgCl$_2$) instead of 70 µL NADPH solution), in order to verify that any apparent loss of test item in the assay incubation was due to metabolism, were used as negative control (NC; n=2).

In the metabolic stability assay, the rate of disappearance of a test compound over time is measured in liver microsomes, and these data are used to calculate in vitro intrinsic clearance ($Cl_{int}$). $Cl_{int}$ data allow to predict the hepatic clearance in vivo, or, in other words, can be used as an indicator for the half life of a compound in vivo and its oral bioavailability. Highly cleared compounds are generally considered to be unfavourable as they are rapidly cleared in vivo resulting in a short duration of action. Said another way, a lower in vitro intrinsic clearance is usually indicative of a longer half life in vivo and of a better oral bioavailability.

The $Cl_{int}$ data obtained are shown in Table 2 below.

TABLE 2

Biological activity, permeability and metabolic stability

| | Comparative Compound No. 169 | Comparative Compound No. 172 | Example Compound No. 13 |
|---|---|---|---|
| Relative IC$_{50}$* | 57 | 29 | 7.6 |
| Cl$_{int}$ (µL/min/mg protein)** | 427 | 56 | 13 |
| Caco-2 BA/AB*** | 3.4 | 1.6 | 0.6 |

| | Comparative Compound No. 170 | Comparative Compound No. 173 | Example Compound No. 1 |
|---|---|---|---|

TABLE 2-continued

Biological activity, permeability and metabolic stability

| | | | |
|---|---|---|---|
| Relative IC$_{50}$* | 37 | 34 | 8.0 |
| Cl$_{int}$ (μL/min/mg protein)** | 329 | 132 | 56 |
| Caco-2 BA/AB*** | 2.9 | 1.1 | 0.7 |

| Comparative Compound No. 171 | Comparative Compound No. 174 | Example Compound No. 6 |
|---|---|---|

| | | | |
|---|---|---|---|
| Relative IC$_{50}$* | 4.3 | 2.6 | 1.0 |
| Cl$_{int}$ (μL/min/mg protein)** | 497 | 135 | 28 |
| Caco-2 BA/AB*** | 7.7 | 1.3 | 1.0 |

Example Compound No. 11

| | |
|---|---|
| Relative IC$_{50}$* | 1.1 |
| Cl$_{int}$ (μL/min/mg protein)** | 20 |
| Caco-2 BA/AB*** | 1.3 |

* IC$_{50}$/(IC$_{50}$ of compound No. 6)
** Metabolic stability in male Wistar rat liver microsomes, according to Obach RS *Drug Metab. Dispos.* 1999, 11, 1350-1359.
*** Caco-2 BA/AB: P$_{app}$ B to A/P$_{app}$ A to AB in differentiated Caco-2 cell monolayer assay according to Hubatsch I. *et al Nat. Protoc.* 2007, 2, 2111-2119.

As can be taken from Table 2 above, the compounds of general formula (I) according to the invention demonstrate a number of important advantages, the existence of which could not have been predicted. Compared with compounds comprising structural elements proposed in the prior art, the compounds of the invention demonstrate:

high antagonistic activity towards hB2R;
significantly improved efflux ratio; and
significantly improved metabolic stability.

More specifically, the exemplified compounds of general formula (I) according to the invention, i.e. Example Compounds Nos. 1, 6, and 13, show an improved antagonistic activity towards hB2R. For instance, Example Compound No. 13 has a relative IC50 value of 7.6, which is 7.5-fold and 3.8-fold improved as compared to the relative IC50 value of Comparative Compound No. 169 and Comparative Compound No. 172, respectively, which lack structural elements of the invention—a fluoro atom in m-position to the chloro atom in combination with the defined stereochemical configuration of the benzylic stereocenter.

The exemplified compounds of general formula (I) according to the invention, i.e. Example Compounds Nos. 1, 6, and 13, also show an improved efflux ratio as compared to the corresponding Comparative Compounds. In fact, all Example Compounds show a very favourable efflux ratio of less than 1.5, while Comparative Compound Nos. 169 to 171 show an unfavourable high efflux ratio of greater than 2, which indicates that the compounds will be subject to active efflux.

The exemplified compounds of general formula (I) according to the invention, i.e. Example Compounds Nos. 1, 6, and 13, also show a significantly improved metabolic stability as compared to the corresponding Comparative Compounds. In fact, all Example Compounds show a substantially lower intrinsic clearance relative to the corresponding Comparative Compounds lacking the combination of structural elements of the invention. For instance, Example Compound No. 6 has a $Cl_{int}$ of 28, which is 17.8-fold and 4.8-fold lower as compared to the Clin of Comparative Compound No. 171 and Comparative Compound No. 174, respectively.

Further, a compound having the stereochemical configuration according to the invention at the benzylic stereocenter will demonstrate more predictable pharmacokinetics, safety, toxicity and tolerability as all compounds should be metabolised in a similar manner as opposed to compounds with a different stereochemistry which may be metabolised differently or at different rates.

All in all, the results demonstrate that compounds of general formula (I) according to the invention are superior to compounds lacking the combination of structural elements of the invention (e.g. a fluoro atom in m-position to a chloro atom in the phenyl moiety in combination with the stereochemical configuration of the alkyl-based substituent at the benzylic stereocenter according to the invention) in activity and in pharmacokintetic properties such as absorption and elimination. Furthermore, these results show that compounds of general formula (I) according to the invention are suitable as active agents in oral drugs.

The features of the present invention disclosed in the specification and/or the claims may both separately and in any combination thereof be material for realizing the invention in various forms thereof.

The invention claimed is:

1. A compound of the general formula (I):

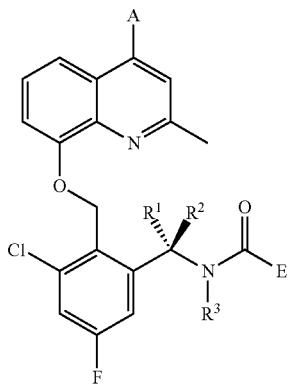

(I)

or a pharmaceutically acceptable salt thereof, wherein A represents the group:

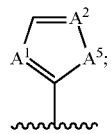

$A^1$ is N;
$A^2$ is N;
$A^5$ is N—$R^{45}$;
$R^{45}$ represents a hydrogen atom or a $(C_1$-$C_3)$alkyl group;
$R^1$ represents a $(C_1$-$C_2)$alkyl or $(C_2$-$C_4)$alkoxyalkyl group, which alkyl group or alkoxyalkyl group may be substituted by one or more, identical or different, group(s) selected from a deuterium atom, halogen atom, and OH;

$R^2$ represents a hydrogen atom or a deuterium atom;
$R^3$ represents a hydrogen atom or $(C_1$-$C_3)$alkyl;
E represents $CR^{E1}R^{E2}R^{E3}$ or Hce;
Hce represents a monocyclic, partially unsaturated or aromatic heterocycle having 3 to 5 C atoms and 1 to 3 N atom(s) or 3 to 5 C atoms, 1-2 N atom(s) and 1 O atom; which heterocycle is unsubstituted or may be mono- or, disubstituted, at each occasion independently, by a halogen atom, OH, $(C_1$-$C_3)$alkyl, $(C_1$-$C_3)$haloalkyl, $(C_1$-$C_3)$alkoxy, $(C_1$-$C_3)$haloalkoxy or $=$O;
$R^{E1}$ and $R^{E2}$ each, independently of one another, represents a hydrogen atom, halogen atom, or G;
$R^{E3}$ represents a hydrogen atom, halogen atom, G, OG or OH; and
G represents a $(C_1$-$C_6)$alkyl group in which 1 to 7 H atoms may be replaced by a halogen atom.

2. The compound, or a pharmaceutically acceptable salt thereof, according to claim 1, wherein $R^1$ represents $CH_3$, $CD_3$, $CH_2OH$, $CH_2F$, $CHF_2$ or $CF_3$.

3. The compound, or a pharmaceutically acceptable salt thereof, according to claim 1, wherein $R^1$ represents $CH_3$, $CD_3$ or $CH_2OH$.

4. The compound, or a pharmaceutically acceptable salt thereof, according to claim 3, wherein $R^3$ represents a hydrogen atom or a methyl group.

5. The compound, or a pharmaceutically acceptable salt thereof, according to claim 4, wherein A represents the group

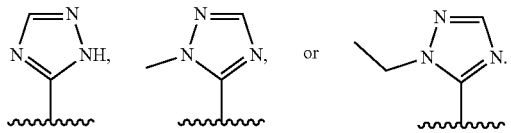

6. The compound, or a pharmaceutically acceptable salt thereof, according to claim 5, wherein E represents

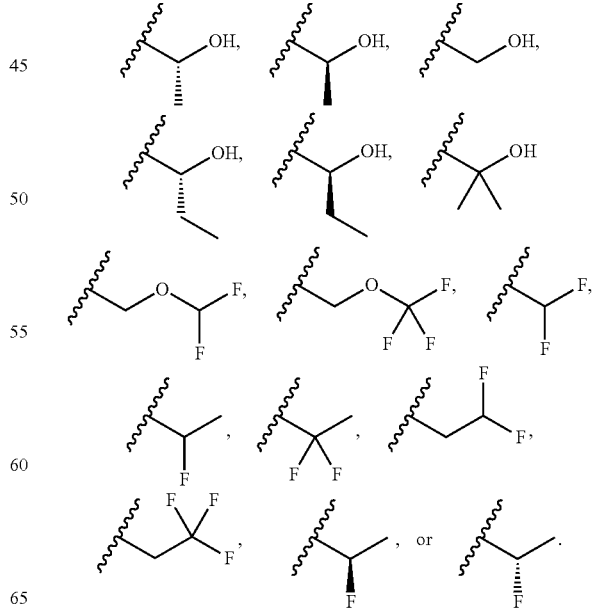

7. The compound, or a pharmaceutically acceptable salt thereof, according to claim 5, wherein E represent

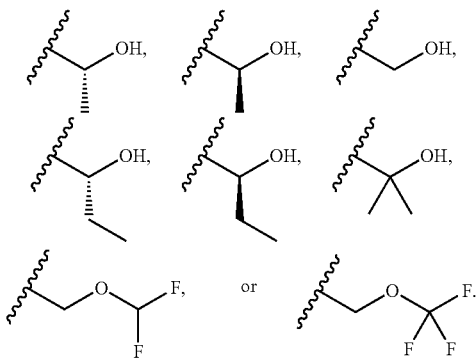

8. The compound, or a pharmaceutically acceptable salt thereof, according to claim 5, wherein E represents

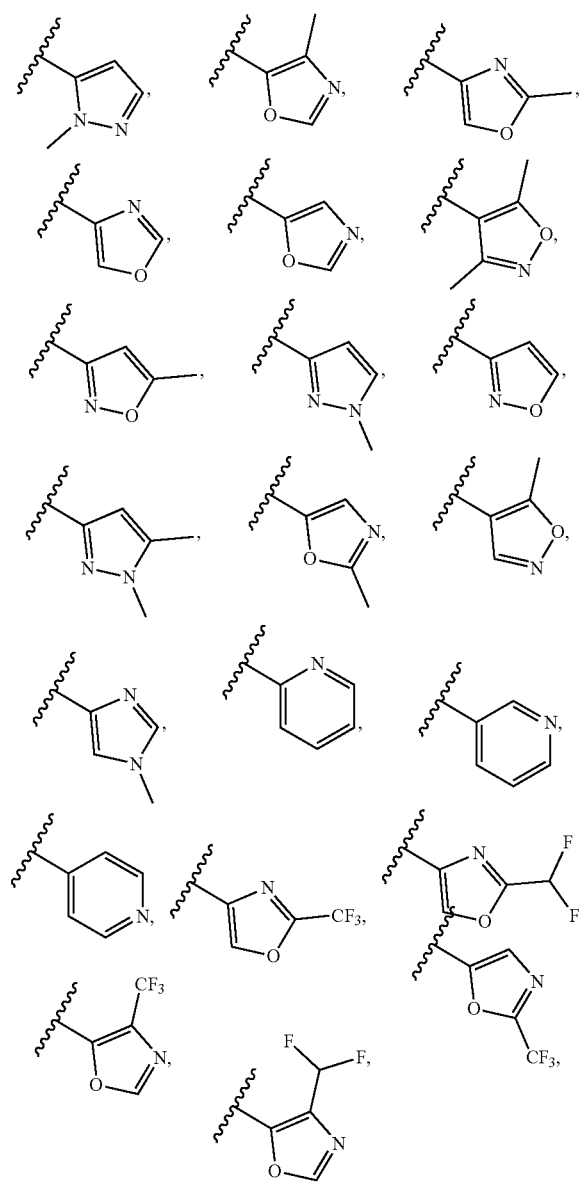

-continued

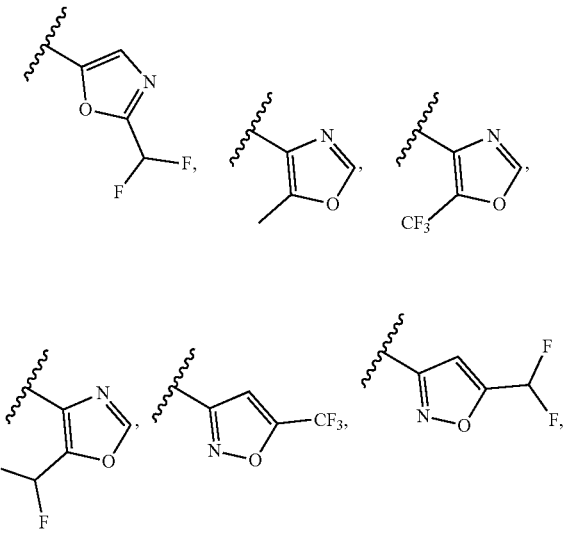

9. A pharmaceutical composition that comprises a compound, or a pharmaceutically acceptable salt thereof, according to claim 1 and at least one carrier substance, excipient or adjuvant.

10. The pharmaceutical composition according to claim 9, wherein the pharmaceutical composition is formulated as an aerosol, a cream, a gel, a pill, a capsule, a syrup, a solution, a transdermal patch or a pharmaceutical delivery device.

11. A method of treating angioedema in a subject comprising administering to the subject with angioedema a compound, or a pharmaceutically acceptable salt thereof, according to claim 1.

12. A compound having the following structure:

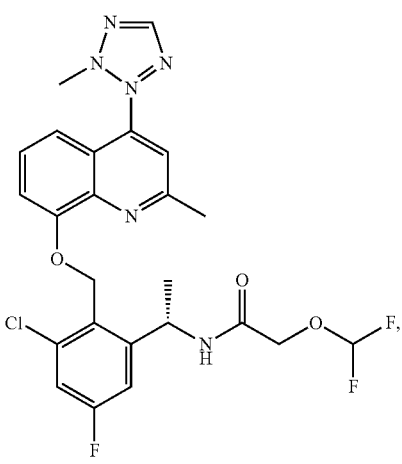

137
-continued
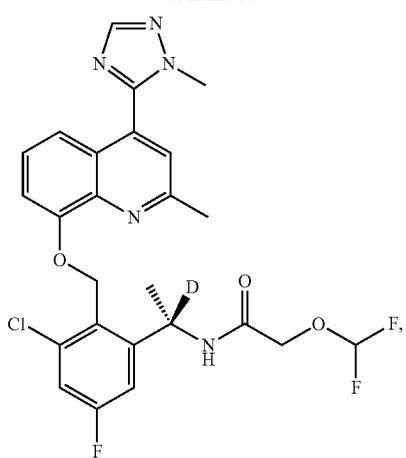
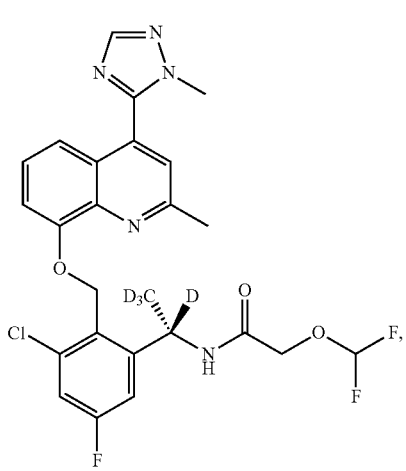
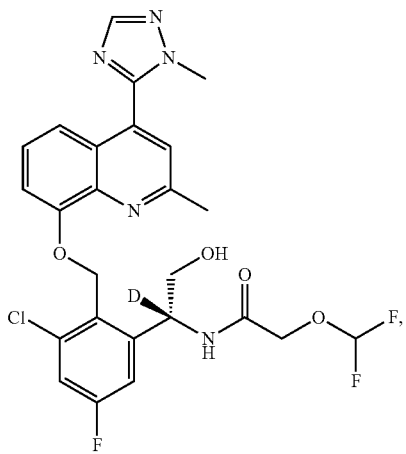
138
-continued
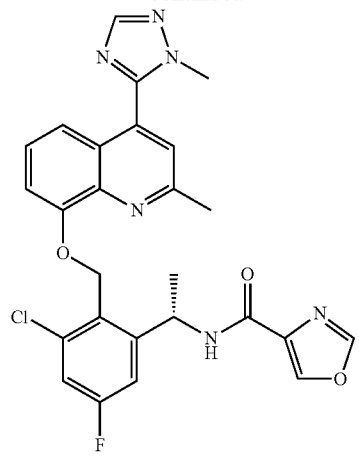
,
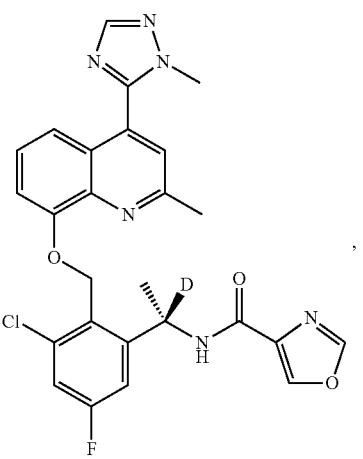 [SMILES: [2H]C([2H])([2H])[C@]([2H])(NC(=O)c1cocn1)c1cc(F)cc(Cl)c1COc1cccc2c(-c3ncnn3C)cc(C)nc12]
, or
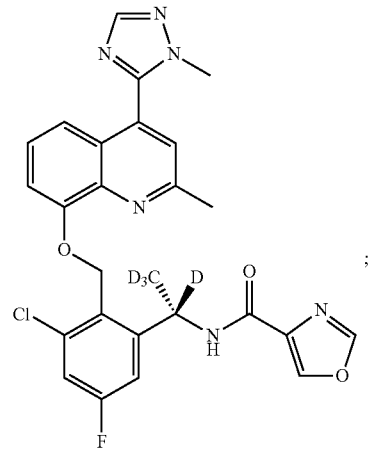
;
or a pharmaceutically acceptable salt thereof.

13. A pharmaceutical composition that comprises a compound, or a pharmaceutically acceptable salt thereof, according to claim 12 and at least one carrier substance, excipient or adjuvant.

14. The pharmaceutical composition according to claim 13, wherein the pharmaceutical composition is formulated as an aerosol, a cream, a gel, a pill, a capsule, a syrup, a solution, a transdermal patch or a pharmaceutical delivery device.

15. A method of treating angioedema in a subject comprising administering to the subject with angioedema a compound, or a pharmaceutically acceptable salt thereof, according to claim 12.

\* \* \* \* \*